United States Patent
Beigelman et al.

(12) 
(10) Patent No.: US 6,482,932 B1
(45) Date of Patent: *Nov. 19, 2002

(54) NUCLEOSIDE TRIPHOSPHATES AND THEIR INCORPORATION INTO OLIGONUCLEOTIDES

(75) Inventors: Leonid Beigelman, Longmont, CO (US); Alex Burgin, Chula Vista, CA (US); Amber Beaudry, Broomfield, CO (US); Alexander Karpeisky, Lafayette, CO (US); Jasenka Matulic-Adamic, Boulder, CO (US); David Sweedler, Louisville, CO (US); Shawn Zinnen, Denver, CO (US)

(73) Assignee: Ribozyme Pharmaceuticals, Incorporated, Boulder, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 09/301,511

(22) Filed: Apr. 28, 1999

Related U.S. Application Data

(63) Continuation-in-part of application No. 09/186,675, filed on Nov. 4, 1998, now Pat. No. 6,127,535.
(60) Provisional application No. 60/083,727, filed on Apr. 29, 1998, and provisional application No. 60/064,866, filed on Nov. 5, 1997.

(51) Int. Cl.$^7$ .................. C07H 21/02; C07H 21/04; A61K 31/70
(52) U.S. Cl. ............. 536/23.1; 536/23.2; 536/25.1; 536/25.34; 514/44; 435/9.1
(58) Field of Search ................ 536/23.1, 23.2, 536/25.1, 25.34; 514/44; 435/9.1

(56) References Cited

U.S. PATENT DOCUMENTS

| | | | |
|---|---|---|---|
| 4,987,071 A | | 1/1991 | Cech et al. |
| 5,334,711 A | | 8/1994 | Sproat et al. |
| 5,525,468 A | | 6/1996 | McSwiggen et al. |
| 5,589,332 A | | 12/1996 | Shih et al. |
| 5,646,042 A | | 7/1997 | Stinchcomb et al. |
| 5,672,695 A | * | 9/1997 | Eckstein et al. |
| 5,741,679 A | | 4/1998 | George et al. |
| 5,834,186 A | | 11/1998 | George et al. |
| 5,871,914 A | | 2/1999 | Nathan et al. |
| 6,127,535 A | * | 10/2000 | Beigelman et al. ...... 536/26.26 |

FOREIGN PATENT DOCUMENTS

| | | | |
|---|---|---|---|
| WO | 91/03162 | | 3/1991 |
| WO | 93/23057 | | 11/1993 |
| WO | 95/04818 | | 2/1995 |
| WO | 95/13380 | | 5/1995 |
| WO | 96/10390 | | 4/1996 |
| WO | W O 97/26270 A2 | * | 7/1997 |
| WO | 98/13526 | | 4/1998 |
| WO | 98/27104 | | 6/1998 |
| WO | W O 98/28317 A2 | * | 7/1998 |
| WO | 99/04819 | | 2/1999 |
| WO | 99/05094 | | 2/1999 |
| WO | 99/29842 | | 6/1999 |
| WO | W O 99/58665 A2 | * | 11/1999 |
| WO | W O 00/20621 A1 | * | 4/2000 |
| WO | 00/24931 | | 5/2000 |
| WO | 00/26226 | | 5/2000 |
| WO | W O 00/58473 A2 | * | 10/2000 |
| WO | W O 01/16312 A2 | * | 3/2001 |
| WO | W O 01/57058 A2 | * | 8/2001 |
| WO | W O 01/64876 A2 | * | 9/2001 |
| WO | W O 01/64877 A2 | * | 9/2001 |

OTHER PUBLICATIONS

Beaucage et al., "The Functionalization of Oligonucleotides Via Phosphoramidite Derivatives," *Tetrahedron*, 49(10), 1925–1963 (Mar. 5, 1993).*

Sioud et al., "A Nuclease–Resistant Protein Kinase Cα Ribozyme Blocks Glioma Cell Growth," *Nature Biotechnology*, 16, 557–562 (Jun., 1996).*

Yamamoto et al., "Abrogation of Lung Metastatis of Human Fibrosarcoma Cells by Ribozyme–Mediated Suppression of Integrin α6 Subunit Expression," *International Journal of Cancer*, 65, 519–524 (1996).*

Christoffersen et al., "Application of Computational Technologies to Ribozyme Biotechnology Products," *Journal of Molecular Structure (Theochem)*, 311, 273–284 (1994).*

Akhtar and Juliano, "Cellular uptake and intracellular fate antisense oligonucleotides," *Trends in Cell Biology* 2:139–144 (1992).

Asakura and Robins, "Cerium (IV)–Mediated Halogenation at C–5 of Uracil Derivatives," *J. Org. Chem.* 55: 4928–4933 (1990).

Baselga et al., "Recombinant Humanized Anti–HER2 Antibody (Herceptin™) Enhances the Antitumor Activity of Paclitaxel and Doxorubicin against HER2/neu Overexpressing Human Breast Cancer Xenografts," *Cancer Research* 58:2825–2831 (1998) (Jul. 1, 1998).

Beaudry and Joyce, "Minimum Secondary Structure Requirements for Catalytic Activity of a Self–Splicing Group I Intron," *Biochemistry* 29:6534–6539 (1990) (Iss No. 27).

Been et al., "Secondary Structure of the Self–Cleaving RNA of Hepatitis Delta Virus: Applications to Catalytic RNA Design," *Biochemistry* 31:11843–11852 (1992).

(List continued on next page.)

Primary Examiner—Johann Richter
Assistant Examiner—Lawrence E Crane
(74) Attorney, Agent, or Firm—McDonnell Boehnen Hulbert & Berghoff

(57) ABSTRACT

Novel nucleotide triphosphates, methods of synthesis and process of incorporating these nucleotide triphosphates into oligonucleotides, and isolation of novel nucleic acid catalysts (e.g., ribozymes) are disclosed.

20 Claims, 9 Drawing Sheets

OTHER PUBLICATIONS

Beigelman et al., "Synthesis of 1–Deoxy–D–Ribofuranose Phosphoramidite and the Incorporation of Abasic Nucleotides in Stem–Loop II of a Hammerhead Ribozyme," *Bioorganic & Medicinal Chemistry Letters* 4(14):1715–1720 (1994).

Bellon et al., "Amino–Linked Ribozymes: Post–Synthetic Conjugation of Half–Ribozymes," *Nucleosides & Nucleotides* 16:951–954 (1997).

Bellon et al., "Post–synthetically Ligated Ribozymes: An Alternative Approach to Iterative Solid Phase Synthesis," *Bioconjugate Chem.* 8:204–212 (1997) (Iss. No. 2).

Benseler et al., "Hammerhead–like Molecules Containing Non–Nucleoside Linkers are Active RNA Catalysts," *J. Am. Chem. Soc.* 115:8483–8484 (1993).

Berchuk et al., "Overexpression of HER–2/neu Is Associated with Poor Survival in Advanced Epithelial Ovarian Cancer," *Cancer Research* 50:4087–4091 (1990) (Jul. 1, 1990).

Bertram et al., "Reduction of erbB2 gene product in mamma carcinoma call lines by erbB2 mRNA–specific and tyrosine kinase consensus phosphorothioate antisense oligonucleotides," *Biochemical and Biophysical Research Communications* 2000:661–667 (1994) (Apr. 15, 1994).

Beveridge, "Review of clinical studies of CA 27.29 in breast cancer management," *The International Journal of Biological Markers* 14(1):36–39 (1999).

Bonner et al., "Characterization of a set of T7 RNA polymerase active site mutants," *J. Biol. Chem.* 269:25120–25128 (1994) (Issue No. 40, Oct. 7, 1994).

Burlina et al., "Chemial Engineering of Rnase Resistant and Catalytically Active Hammerhead Ribozymes," *Bioorganic & Medicinal Chemistry* 5:1999–2010 (1997).

Caruthers et al., "Chemical Synthesis of Deoxyoligonucleotides and Deoxyoligonucleotide Analogs," *Methods in Enzymology* 211:3–19 (1992).

Cech, "Ribozyme engineering," *Current Opinion in Structural Biology* 2:605–609 (1992).

Cech, "Ribozymes and Their Medical Implications," *JAMA* 260:3030–3034 (1988) (Nov. 25, 1988).

Christoffersen and Marr, "Ribozymes as Human Therapeutic Agents," *Journal of Medicinal Chemistry* 38(12):2023–2037 (1995).

Colomer et al., "erbB–2 antisense oligonucleotides inhibit the proliferation of breast carcinoma cells with erbB–2 oncogene amplification," *Br.J. Cancer* 70:819–825 (1994).

Czubayko et al., "Adenovirus–mediated transduction of ribozymes abrogates HER–2/neu and pleiotrophin expression and inhibits tumor cell proliferation," *Gene Therapy* 4:943–949 (1997).

Dewey et al., "New Uridine Derivatives for Systematic Evolution of RNA Ligands by Exponential Enrichment," *J. Am. Chem. Soc.* 117: 8474–8475 (1995).

Dreyfus, "Restriction Ribozymes?" *The Einstein Quarterly Journal of Biology and Medicine* 6(2):92–93 (1988) (Issue No. 2).

Earnshaw et al., "Modified Oligoribonucleotides as Site–Specific Probes of RNA Structure and Function," *Biopolymers* 48:39–55 (1998).

Eaton et al., "Ribonucleosides and RNA," *Annu. Rev. Biochem.* 64:837–863 (1995).

Freier et al., "Improved free–energy parameters for predictions of RNA duplex stability," *Proc. Natl. Acad. Sci. USA* 83:9373–9377 (1986) (Dec., 1986).

Gion et al., "Comparison of the Diagnostic Accuracy of CA27.29 and CA15.3 in Primary Breast Cancer," *Clinical Chemistry* 45(5):630–637 (1999) (Issue No. 5).

Guo and Collins, "Efficient trans–cleavage of a stem–loop RNA substrate by a ribozyme derived from Neurospora VS RNA," *The EMBO Journal* 14(2):368–376 (1995) (Issue No. 2).

Haselhoff and Gerlach, "Simple RNA enzymes with new and highly specific endoribonuclease activites," *Nature* 334:585–591 (1988) (Aug. 18, 1988).

Hendry et al., "Using linkers to investigate the spatial separation of the conserved nucleotides $A_9$ and $G_{12}$ in the hammerhead ribozyme," *Biochimica et Biophysica Acta* 1219:405–412 (1994).

Hertel et al., "Numbering System for the Hammerhead," *Nucleic Acids Research* 20:3252 (1992) (Issue No. 12).

Hobbs, "Palladium–Catalyzed Synthesis of Alkynylamino Nucleosides. A Universal Linker for Nucleic Acids," *J. Org. Chem.* 54: 3420–3422 (1989).

Huang et al., "Determinants of Ribose Specificity in RNA Polymerization: Effects of $Mn^{2+}$ and Deoxynucleoside Monophosphate Incorporation into Transcripts," Biochemistry 36: 13718–13728 (1997).

Hung et al., "HER–2/neu–targeting gene therapy—a review," *Gene* 159:65–71 (1995).

Jaeger et al., "Improved predictions of secondary structures for RNA," *Proc. Natl. Acad. Sci. USA* 86:7706–7710 (1989) (Oct., 1989).

Jaeger et al., "[17] Predicting Optimal and Suboptimal Secondary Structure for RNA," *Methods in Enzymology* 183:281–306 (1990).

Jeffries and Symons, "A catalytic 13–mer ribozyme," *Nucleic Acids Research* 17:1371–1377 (1989) (Issue No. 4).

Karpeisky et al, "Highly Efficient Synthesis of 2'–O–Amino Nucleosides And Their Incorporation in Hammerhead Ribozymes," *Tetrahedron Letters* 39:1131–1134 (1998).

Kim and Cech, "Three–dimensional model of the active site of the self–splicing rRNA precursor of Tetrahymena," *Proc. Natl. Acad. Sci. USA* 84:8788–8792 (1987) (Dec. 1987).

Kovacs and Otvos, "Simple Synthesis of 5–Vinyl– and 5–Ethynyl–2'–Deoxyuridine–5'–Triphosphates," *Tetrahedron Letters* 29:4525–4528 (1988) (Issue No. 36).

Long and Uhlenbeck, "Kinetic characterization of intramolecular and intermolecular hammerhead RNAs with stem II deletions," *Proc. Natl. Acad. Sci. USA* 91:6977–6981 (1994) (Jul. 1994).

Lu and Wimmer, "Poliovirus chimeras replicating under the translational control of genetic elements of hepatitis C virus reveal unusual properties of the internal ribosomal entry site of hepatitis C virus," *Proc. Natl. Acad. Sci. USA* 93:1412–1417 (1996) (Feb., 1996).

Lüftner et al., "c–erbB–2 in serum of patients receiving fractionated paclitaxel chemotherapy," *The International Journal of Biological Markers* 14(2):55–59 (1999).

Maguire et al., "The neu (c–erbB–2) Oncogene," *Seminars in Oncology* 16(2):148–155 (1989) (Apr., 1989).

Matulic–Adamic et al., "Functionalized Nucleoside 5'–triphosphates for In Vitro Selection of New Catalytic Ribonucleic Acids," *Bioorganic & Medicinal Chemistry Letters* 10: 1299–1302 (2000).

McCall et al., "Minimal sequence requirements for ribozyme activity," *Proc. Natl. Acad. Sci. USA* 89:5710–5714 (1992) (Jul. 1992).

Michels and Pyle, "Conversion of a Group II Intron into a New Multiple–Turnover Ribozyme that Selectively Cleaves Oligonucleotides: Elucidation of Reaction Mechanism and Structure/Function Relationships," *Biochemistry* 34:2965–2977 (1995) (Issue No. 9).

Mitra et al., "A mammalian 2–5A system functions as an antiviral pathway in transgenic plants," *Proc. Natl. Acad. Sci. USA* 93:6780–6785 (1996) (Jun., 1996).

Moore and Sharp, "Site–Specific Modification of Pre–mRNA: The 2'–Hydroxyl Groups at the Splice Sites," *Science* 256:992–996 (1992)(May 15, 1992).

Mukhopadhyay and Roth, "Antisense Regulation of Oncogenes in Human Cancer," *Critical Reviews in Oncogenesis* 7:151–190 (1996).

Nathans et al., "Restriction Endonucleases in the Analysis and Restructuring of DNA Molecules," *Annual Review of Biochemistry* 44:273–293 (1975).

Nyilas, "Synthesis of pppA2'p5'A2'p5'A y–amidates by one pot procedure form A2'p5'A2'p5'A," *Tetrahedron Letters.* vol. 38, No. 14, 2517–2518 (1997) (Iss. No. 14).

Padilla and Sousa, "Efficient synthesis of nucleic acids heavily modified with non–canonical ribose 2'–groups using a mutant T7 RNA polymerase (RNAP)," *Nucleic Acids Research* vol. 27, No. 6 1561–1563 (1999).

Pan et al., "Properties of an In Vitro Selected $Pb^{2+}$ Cleavage Motif," *Biochemistry* 33:9561–9565 (1994) (Issue No. 32).

Pegram et al, "Phase II Study of Receptor–Enhanced Chemosensitivity Using Recombinant Humanized Anti–p185$^{HER2/neu}$ Monoclonal Antibody Plus Cisplatin in Patients With HER2/nue–Overexpresing Metastatic Breast Cancer Refractory to Chemotherapy Treatment," *Journal of Clinical Oncology* 16(8):2659–2671 (1998) (Aug. 1998).

Perrault et al., "Mixed deoxyribo– and ribo– oligonucleotides with catalytic activity," *Letters to Nature* 344:565–567 (1990) (Apr. 5, 1990).

Pieken et al., "Kinetic Characterization of Ribonuclease–Resistant 2'–Modified Hammerhead Ribozymes," *Science* 253:314–317 (1991) (Jul. 19, 1991).

Player and Torrence, "The 2–5A System: Modulation of Viral and Cellular Processes Through Acceleration of RNA Degradation," *Pharmacol Ther.* J78:55–113 (1998).

Rodriguez de Paterna et al., "Study of serum tumor markers CEA, CA 15.3 and CA 27.29 as diagnostic parameters in patients with breast carcinoma," *The International Journal of Biological Markers* 10(1):24–29 (1995).

Ross et al., "The HER–2/neu Oncogene in Breast Cancer: Prognostic Factor, Predictive Factor, and Target for Therapy," *The Oncologist* 3:237–252 (1998).

Ruffner et al., "Sequence of Requirements of the Hammerhead RNA Self–Cleavage Reaction," *Biochemistry* 29:10695–10702 (1990) (Issue No. 47).

Sakthivel and Barbas, "Expanding the Potential of DNA for Binding and Catalysis: Highly Functionalized dUTP Derivatives That Are Substrates for Thermostable DNA Polymerases," *Angew. Chem. Int. Ed.* 37, No. 20, 2872–2875 (1998).

Sambrook et al., "Molecular Cloning: A Laboratory Manual," *Cold Spring Harbor Laboratory Press.* (Only Table of Contents for Book 1 supplied). Print/Contexts only.

Santoro et al., "A general purpose RNA–cleaving DNA enzyme," *Proc. Natl. Acad. Sci. USA* 94:4262–4266 (1997) (Apr., 1997).

Scaringe et al., "Chemical synthesis of biologically active oligoribonucleotides using β–cyanoethyl protected ribonucleoside phosphoramidites," *Nucleic Acids Research* 18:5433–5441 (1990) (Issue No. 18).

Shabarova et al., "Chemical ligation of DNA: The first non–enzymatic assembly of a biologically active gene," *Nucleic Acids Research* 19:4247–4251 (1991) (Iss. No. 15).

Silverman et al., "Selective RNA Cleavage by Isolated Rnase L Activated with 2–5A Antisense Chimeric Oligonucleotides," *Methods in Enzymology* 313:522–533 (1999).

Slamon et al., "Human Breast Cancer: Correlation of Relapse and Survival with Amplification of the HER–2/neu Oncogene," *Science* 235:177–182 (1987) (Jan. 9, 1987).

Sparano, "Doxorubicin/Taxane Combinations: Cardiac Toxicity and Pharmacokinetics," *Seminars in Oncology* 26(3):14–19 (1999) (Jun., 1999).

Sugiyama et al., "Catalytic activities of hammerhead ribozymes with a triterpenoid linker instead of stem/loop II," *FEBS Letters* 392:215–219 (1996).

Surveillance, Epidemiology and End Results Program (SEER) Cancer Statistics Review: http://www.seer.ims.nci.nih.gov/Publications/CSR1973–1996/ (Apr. 12, 2001).

Thomson et al., "In vitro selection of hammerhead ribozymes containing a bulged nucleotide in stem II," *Nucleic Acids Research* 24(22):4401–4406 (1996).

Turner et al., "Free Energy Increments for Hydrogen Bonds in Nucleic Acid Base Pairs," *J. Am. Chem. Soc.* 109:3783–3785 (1987) (Issue No. 12).

Turner et al., "Improved Parameters for Prediction of RNA Structure," *Cold Spring Harbor Symposium on Quantitative Biology* LII:123–133 (1987).

Uhlenbeck, "A small catalytic oligribonucleotide," *Nature* 328:596–600 (1987) (Aug. 13, 1987).

Usman and Cedergren, "Exploiting the chemical synthesis of RNA," *TIBS* 17:334–339 (1992) (Sep., 1992).

Usman and McSwiggen, "Chapter 30. Catalytic RNA (Ribozymes) as Drugs," *Annual Reports in Medicinal Chemistry* 30:285–294 (1995).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethionine tRNA," *Journal of the American Chemical Society* 109:7845–7854 (1987) (Issue No. 25).

Usman et al., "Chemical modification of hammerhead ribozymes: activity and nuclease resistance," *Nucleic Acids Symposium Series* 31:163–164 (1994).

Vartanian et al., "Hypermutagenic PCR involving all four transitions and a sizeable proportion of transversions," *Nucleic Acids Research* 24:2627–2631 (1996) (Iss No. 14).

Vaughn et al., "Antisense DNA Downregulation of the ERBB2 Oncogene Measured by a Flow Cytometric Assay," *Proc. Natl. Acad. Sci USA* 92:8338–8342 (1995) (Aug. 1995).

Verma and Eckstein, "Modified Oligonucleotides: Synthesis and Strategy for Users," *Annu. Rev. Biochem.* 67:99–134 (1998).

Wang et al., "Translation of Human Hepatitis C Virus RNA in Cultured Cells is Mediated by an Internal Ribosome–Binding Mechanism," *Journal of Virology* 67:3338–3344 (1993) (Jun., 1993).

Wiechen et al., "Selection of a high activity c–erbB–2 ribozyme using a fusion gene of c–erbB–2 and the enhanced green fluorescent protein," *Cancer Gene Therapy* 5(1):45–51 (1998).

Wincott et al., "Synthesis, deprotection, analysis and purification of RNA and ribozymes," *Nucleic Acids Research* 23:2677–2684 (1995).

Wincott et al., "A Practical Method for the Production of RNA and Ribozymes," *Methods in Molecular Biology* 74:59–69 (1997).

Wright et al., "An intracellular anti–erbB–2 single–chain antibody is specifically cytotoxic to human breast carcinoma cells overexpressing erbB–2," *Gene Therapy* 4:317–322 (1997).

Wu–Pong, "Oligonucleotides: Opportunities for Drug Therapy and Research," *Biopharm* 20–33 (1994) (Nov., 1994).

Yoshikawa et al., "Studies of Phosphorylation. III. Selective Phosphorylation of Unprotected Nucleosides," *Bulletin of the Chemical Society of Japan* 42:3505–3508 (1969) (Dec., 1969).

Zaug et al., "The Tetrahymena ribozyme acts like an RNA restriction endonuclease," *Nature* 324:429–433 (1986) (Dec. 4, 1986).

Zuker, "A comparison of optimal and suboptimal RNA secondary structures predicted by free energy minimization with structures determined by phylogenetic comparison," Nucleic Acids Research, 19: 2707–2714 (1991) (Issue No. 10).

Zuker, "On Finding all Suboptimal Foldings of an RNA Molecule," *Science* 244:48–52 (1989) (Apr. 7, 1989).

Tarasow and Eaton, "Dressed for Success: Realizing the Catalytic Potential of RNA," *Biopolymers* 48: 29–37 (1998).

* cited by examiner

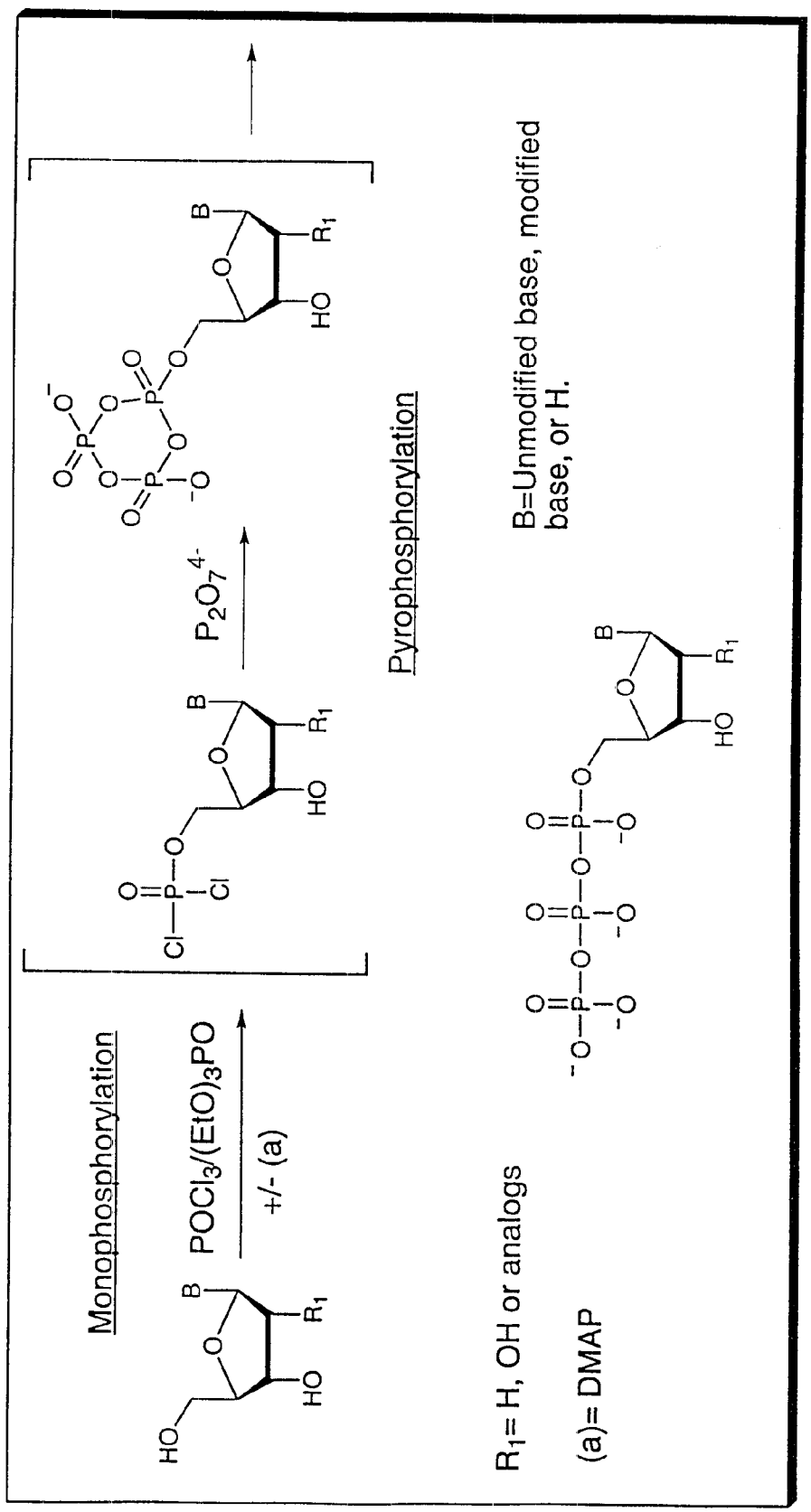
Fig. 1 One-Pot Formation of Nucleosides-5'-Triphosphates

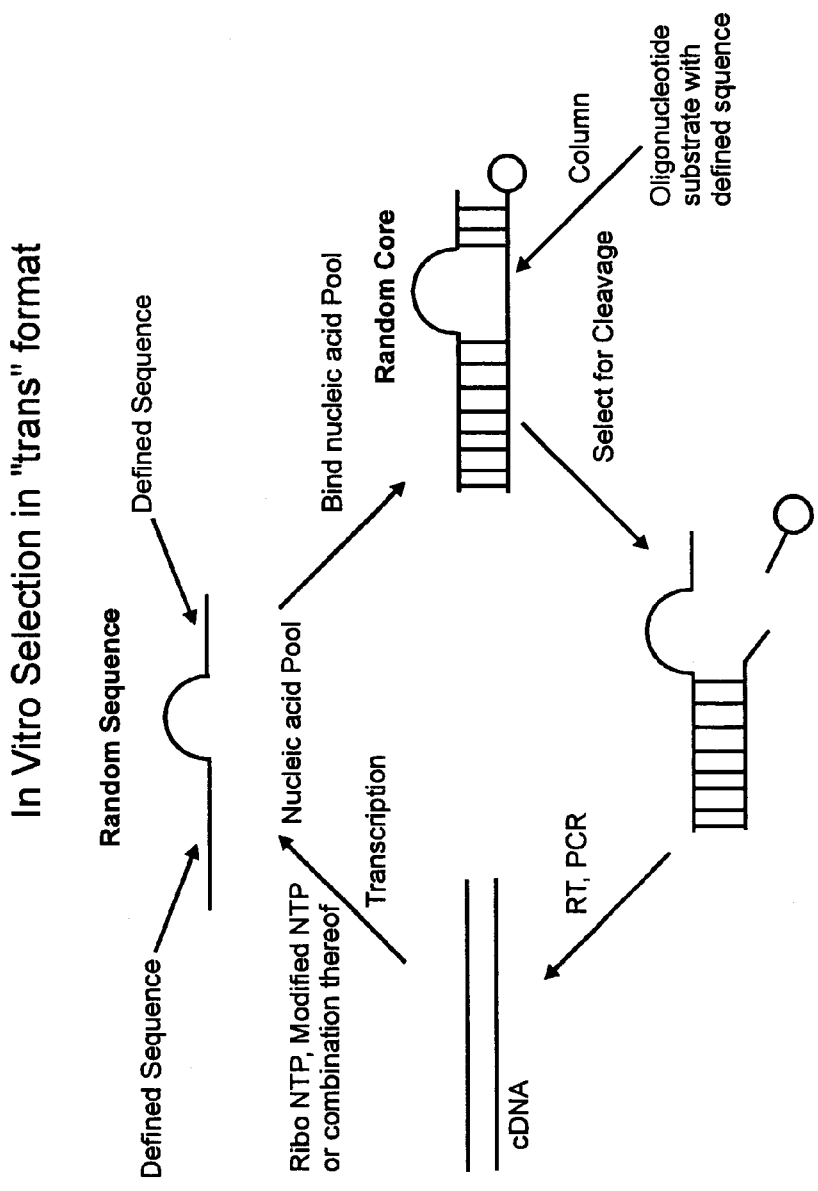
Figure 2: *In Vitro Selection of Trans Acting Nucleic Acid Catalysts*

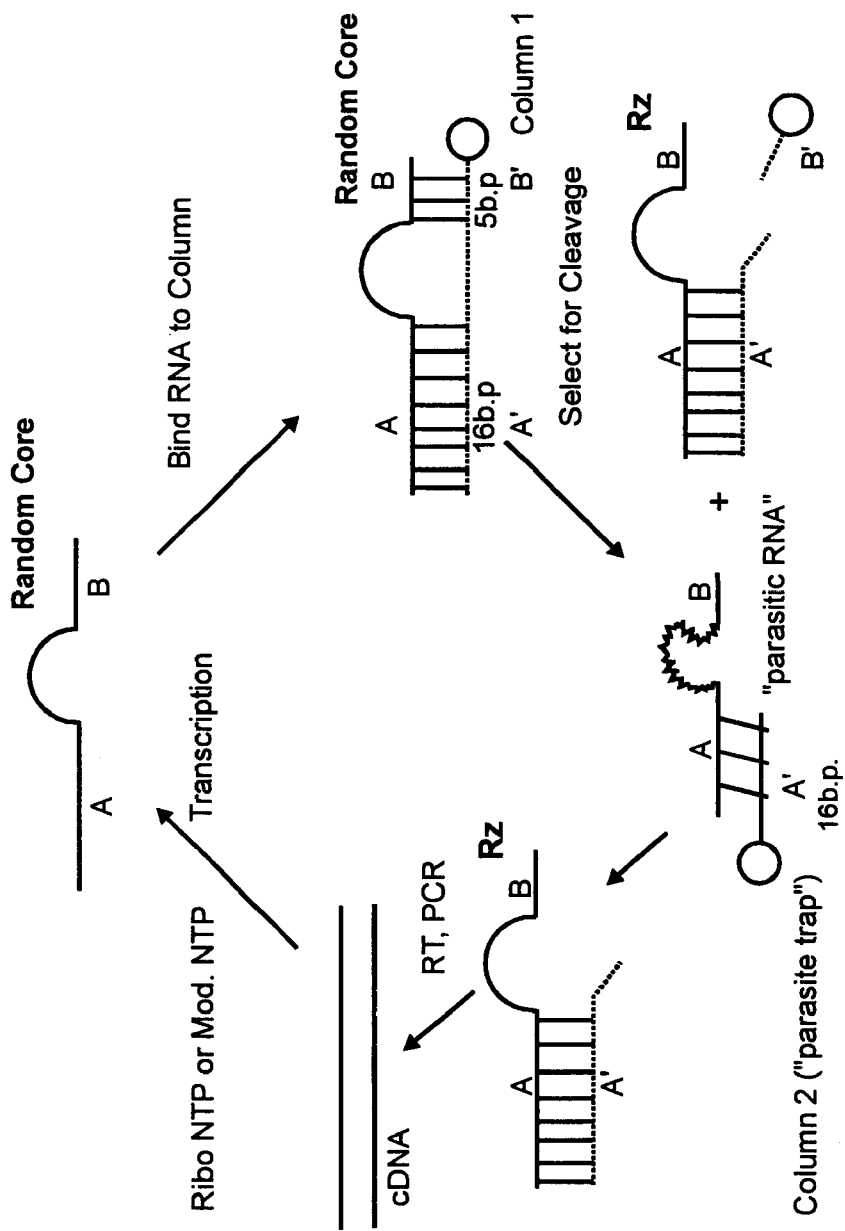
*Figure 3:* Removal of "parasitic RNA" using a Second Selection column

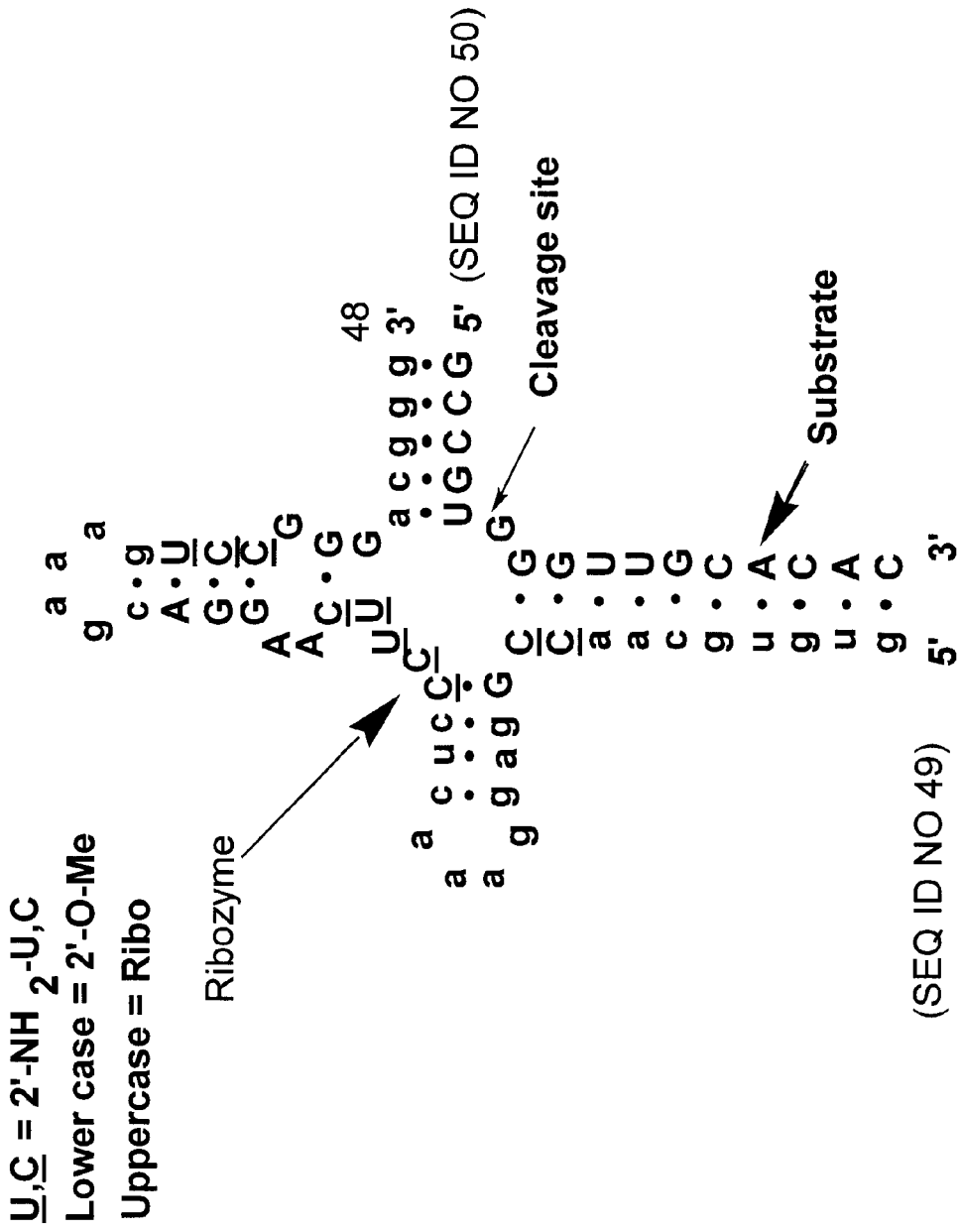
*Figure 4: 2'-O-Me substituted Amberzyme Enzymatic Nucleic Acid Motif*

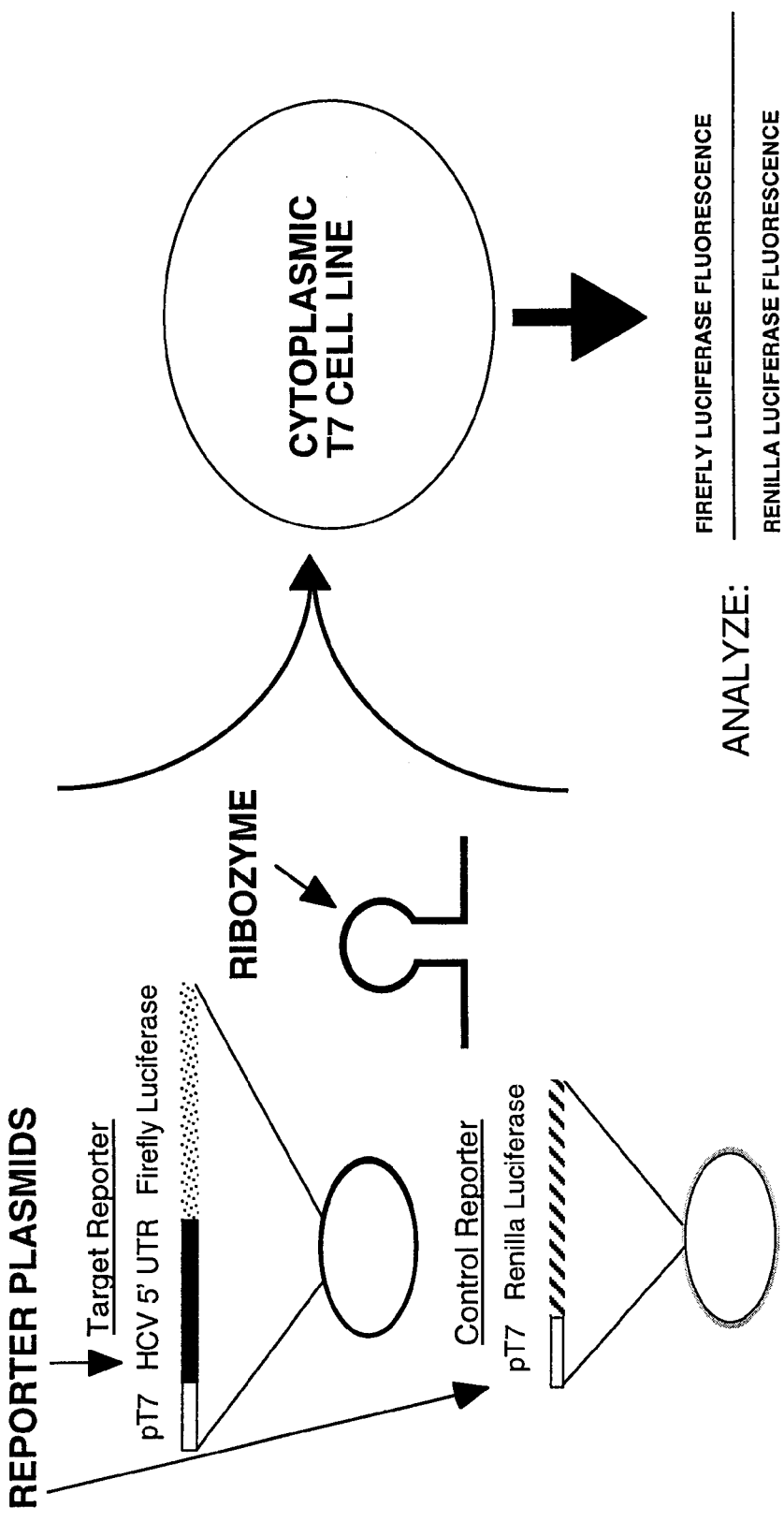
FIGURE 5. Dual Reporter System for Cytoplasmic HCV Target

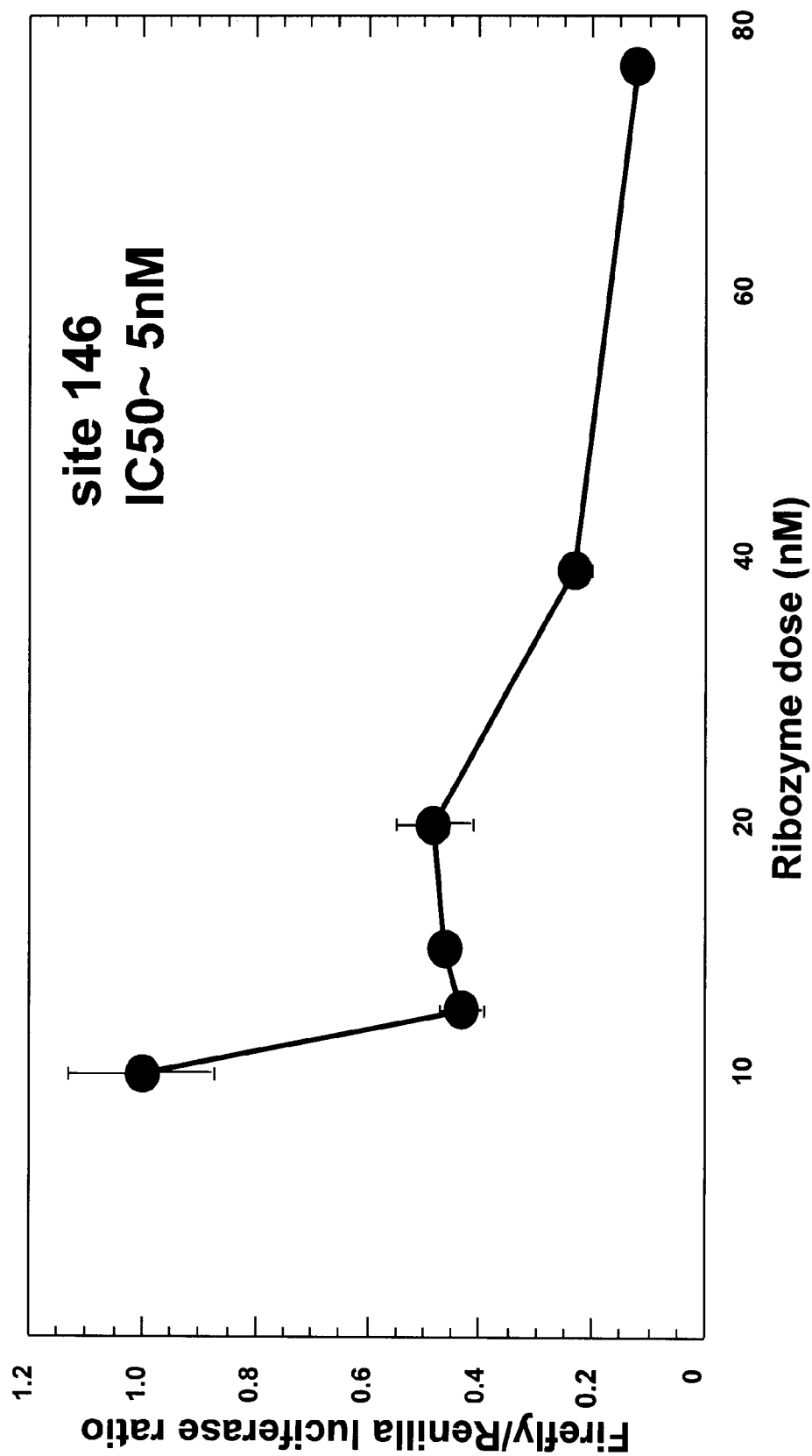

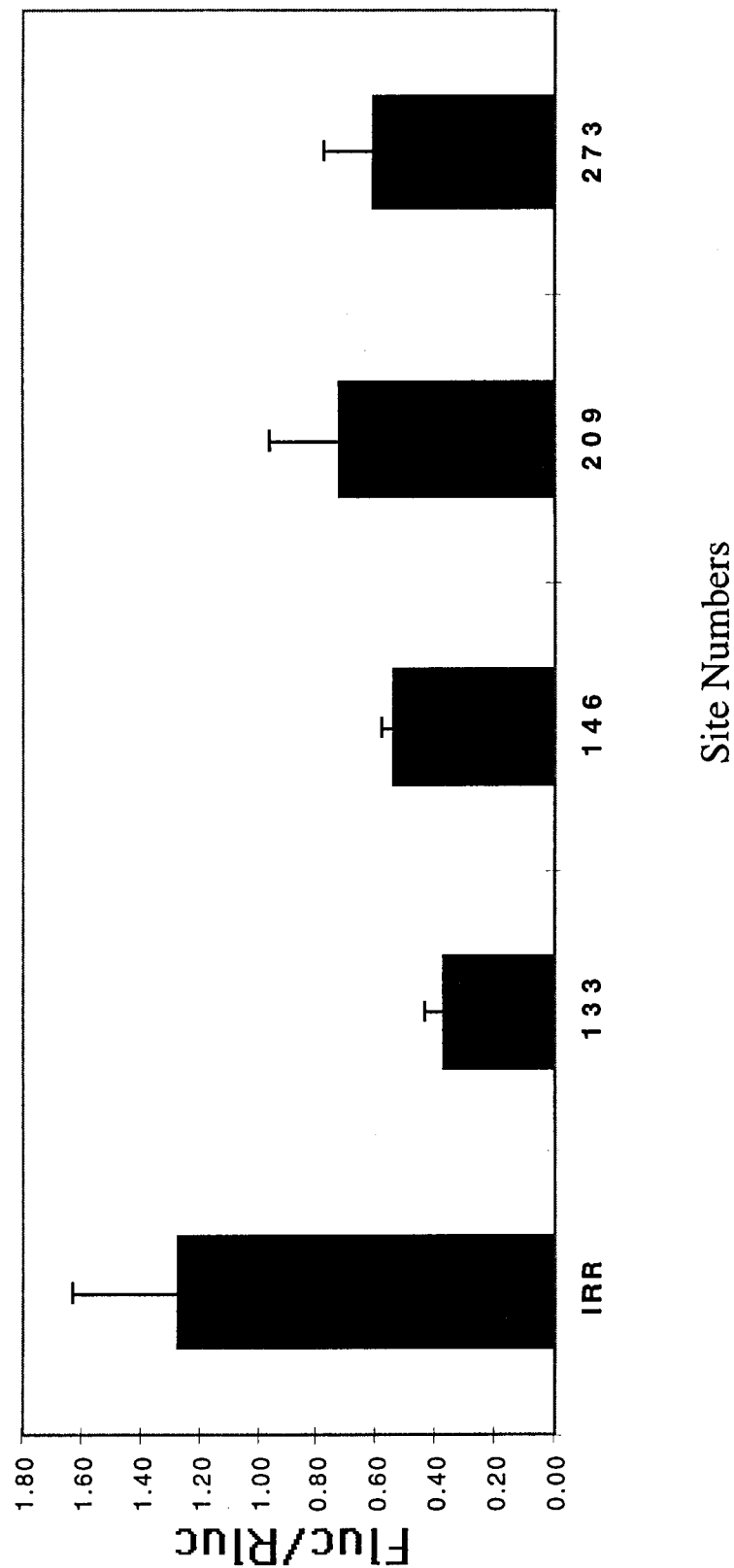
Figure 7. Efficacious Ribozymes Targeting 5'UTR HCV RNA
Sequence and chemical compositions for site numbers are given in table XII

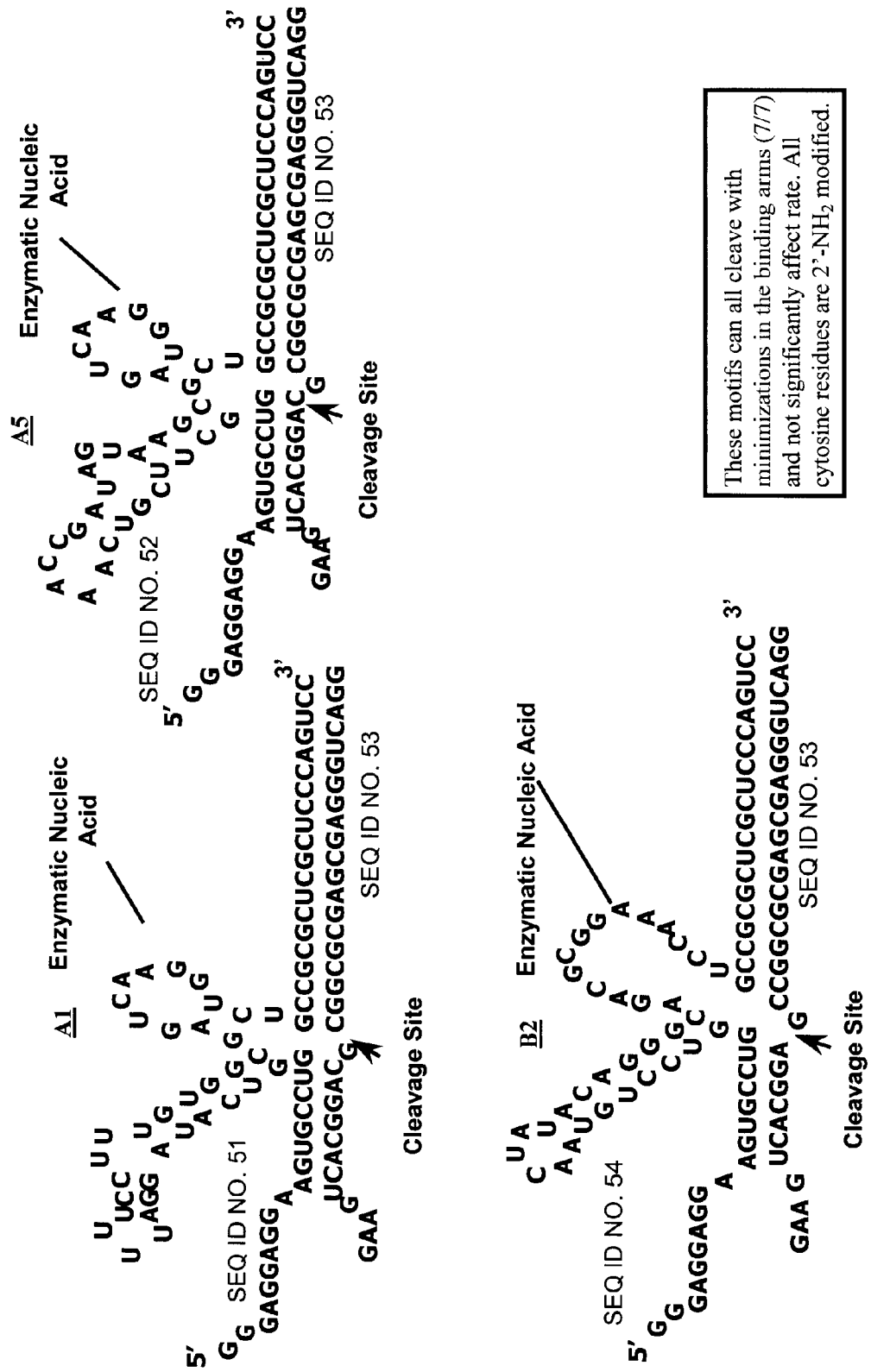
Fig. 8a Class II Enzymatic Nucleic Acid Motifs

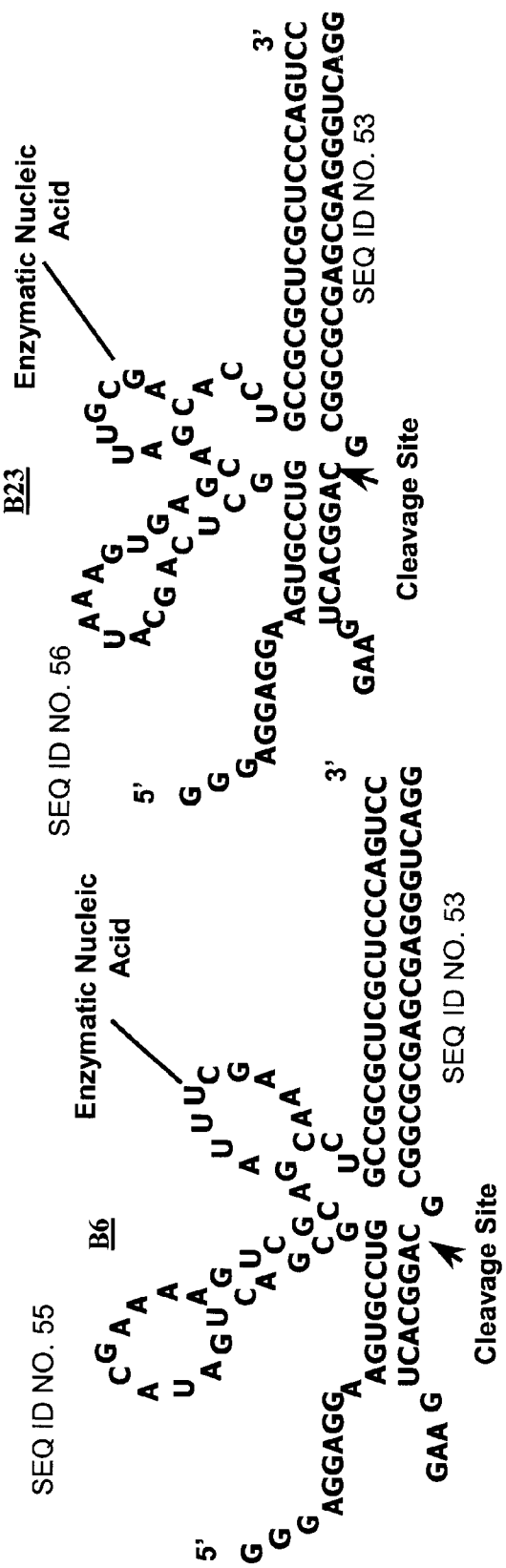
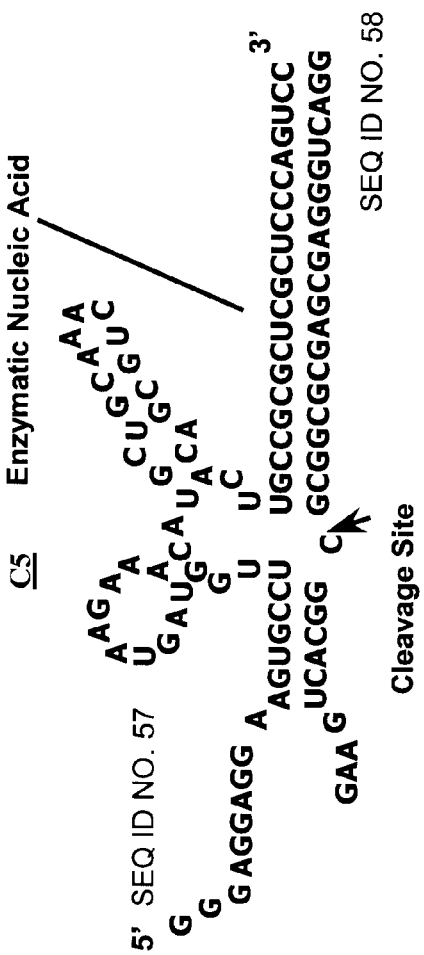
Fig. 8b Class II Enzymatic Nucleic Acid Motifs

NUCLEOSIDE TRIPHOSPHATES AND THEIR INCORPORATION INTO OLIGONUCLEOTIDES

RELATED APPLICATIONS

This patent application is a continuation-in-part of Beigelman et al., U.S. Ser. No., 09/186,675 filed Nov. 4, 1998, now U.S. Pat. No. 6,127,535, and claims the benefit of Beigelman et al., U.S. Ser. No. 60/083,727, filed Apr. 29, 1998, and Beigelman et al., U.S. Ser. No. 60/064,866 filed Nov. 5, 1997, all of these earlier applications are entitled "NUCLEOTIDE TRIPHOSPHATE AND THEIR INCORPORATION INTO OLIGONUCLEOTIDES". Each U.S. Patent is hereby incorporated by reference herein in its entirety including the drawings.

BACKGROUND OF THE INVENTION

This invention relates to novel nucleotide triphosphates (NTPs); methods for synthesizing nucleotide triphosphates; and methods for incorporation of novel nucleotide triphosphates into oligonucleotides. The invention further relates to incorporation of these nucleotide triphosphates into nucleic acid molecules using polymerases under several novel reaction conditions.

The following is a brief description of nucleotide triphosphates. This summary is not meant to be complete, but is provided only to assist understanding of the invention that follows. This summary is not an admission that all of the work described below is prior art to the claimed invention.

The synthesis of nucleotide triphosphates and their incorporation into nucleic acids using polymerase enzymes has greatly assisted in the advancement of nucleic acid research. The polymerase enzyme utilizes nucleotide triphosphates as precursor molecules to assemble oligonucleotides. Each nucleotide is attached by a phosphodiester bond formed through nucleophilic attack by the 3' hydroxyl group of the oligonucleotide's last nucleotide onto the 5' triphosphate of the next nucleotide. Nucleotides are incorporated one at a time into the oligonucleotide in a 5' to 3' direction. This process allows RNA to be produced and amplified from virtually any DNA or RNA templates.

Most natural polymerase enzymes incorporate standard nucleotide triphosphates into nucleic acid. For example, a DNA polymerase incorporates dATP, dTTP, dCTP, and dGTP into DNA and an RNA polymerase generally incorporates ATP, CTP, UTP, and GTP into RNA. There are however, certain polymerases that are capable of incorporating non-standard nucleotide triphosphates into nucleic acids (Joyce, 1997, *PNAS* 94, 1619–1622, Huang et al., *Biochemistry* 36, 8231–8242).

Before nucleosides can be incorporated into RNA transcripts using polymerase enzymes they must first be converted into nucleotide triphosphates which can be recognized by these enzymes. Phosphorylation of unblocked nucleosides by treatment with POCl₃ and trialkyl phosphates was shown to yield nucleoside 5'-phosphorodichloridates (Yoshikawa et al., 1969, *Bull. Chem. Soc.*(Japan) 42, 3505). Adenosine or 2'-deoxyadenosine 5'-triphosphate was synthesized by adding an additional step consisting of treatment with excess tri-n-butylammonium pyrophosphate in DMF followed by hydrolysis (Ludwig, 1981, *Acta Biochim. et Biophys. Acad. Sci. Hung.* 16, 131–133).

Non-standard nucleotide triphosphates are not readily incorporated into RNA transcripts by traditional RNA polymerases. Mutations have been introduced into RNA polymerase to facilitate incorporation of deoxyribonucleotides into RNA (Sousa & Padilla, 1995, *EMBO J.* 14,4609–4621, Bonner et al., 1992, *EMBO J.* 11, 3767–3775, Bonner et al., 1994, *J. Biol. Chem.* 42, 25120–25128, Aurup et al., 1992, *Biochemistry* 31, 9636–9641).

McGee et al., International PCT Publication No. WO 95/35102, describes the incorporation of 2'-NH₂-NTP's, 2'-F-NTP's, and 2'-deoxy-2'-benzyloxyamino UTP into RNA using bacteriophage T7 polymerase.

Wieczorek et al., 1994, *Bioorganic & Medicinal Chemistry Letters* 4, 987–994, describes the incorporation of 7-deaza-adenosine triphosphate into an RNA transcript using bacteriophage T7 RNA polymerase.

Lin et al., 1994, *Nucleic Acids Research* 22, 5229–5234, reports the incorporation of 2'-NH₂-CTP and 2'-NH₂-UTP into RNA using bacteriophage T7 RNA polymerase and polyethylene glycol containing buffer. The article describes the use of the polymerase synthesized RNA for in vitro selection of aptamers to human neutrophil elastase (HNE).

SUMMARY OF THE INVENTION

This invention relates to novel nucleotide triphosphate (NTP) molecules, and their incorporation into nucleic acid molecules, including nucleic acid catalysts. The NTPs of the instant invention are distinct from other NTPs known in the art. The invention further relates to incorporation of these nucleotide triphosphates into oligonucleotides using an RNA polymerase; the invention further relates to novel transcription conditions for the incorporation of modified (non-standard) and unmodified NTP's into nucleic acid molecules. Further, the invention relates to methods for synthesis of novel NTP's In a first aspect, the invention features NTP's having the formula triphosphate-OR, for example the following formula I:

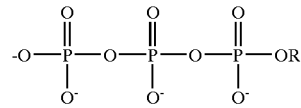

where R is any nucleoside; specifically the nucleosides 2'-O-methyl-2,6-diaminopurine riboside; 2'-deoxy-2'amino-2,6-diaminopurine riboside; 2'-(N-alanyl)amino-2'-deoxy-uridine; 2'-(N-phenylalanyl)amino-2'-deoxy-uridine; 2'-deoxy-2'-(N-β-alanyl)amino; 2'-deoxy-2'-(lysiyl)amino uridine; 2'-C-allyl uridine; 2'-O-amino-uridine; 2'-O-methylthiomethyl adenosine; 2'-O-methylthiomethyl cytidine; 2'-O-methylthiomethyl guanosine; 2'-O-methylthiomethyl-uridine; 2'-Deoxy-2'-(N-histidyl)amino uridine; 2'-deoxy-2'-amino-5-methyl cytidine; 2'-(N-β-carboxamidine-β-alanyl)amino-2'-deoxy-uridine; 2'-deoxy-2'-(N-β-alanyl)-guanosine; 2'-O-amino-adenosine; 2'-(N-lysyl)amino-2'-deoxy-cytidine; 2'-Deoxy-2'-(L-histidine) amino Cytidine; and 5-Imidazoleacetic acid 2'-deoxy-5'-triphosphate uridine. In a second aspect, the invention features a process for the synthesis of pyrimidine nucleotide triphosphate (such as UTP, 2'-O-MTM-UTP, dUTP and the like) including the steps of monophosphorylation where the pyrimidine nucleoside is contacted with a mixture having a phosphorylating agent (such as phosphorus oxychloride, phospho-tris-triazolides, phospho-tris-triimidazolides and the like), trialkyl phosphate (such as triethylphosphate or trimethylphosphate or the like) and dimethylaminopyridine (DMAP) under conditions suitable for the formation of pyrimidine monophosphate; and pyrophosphorylation where the pyrimidine monophosphate is contacted with a pyrophosphorylating reagent (such as tributylammonium pyrophosphate) under conditions suitable for the formation of pyrimidine triphosphates.

The term "nucleotide" as used herein is as recognized in the art to include natural bases (standard), and modified bases well known in the art. Such bases are generally located at the 1' position of a sugar moiety. Nucleotides generally include a base, a sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; all hereby incorporated by reference herein). There are several examples of modified nucleic acid bases known in the art as recently summarized by Limbach et al., 1994, *Nucleic Acids Res.* 22, 2183. Some of the non-limiting examples of base modifications that can be introduced into nucleic acids without significantly effecting their catalytic activity include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine) and others (Burgin et al., 1996, *Biochemistry*, 35, 14090). By "modified bases" in this aspect is meant nucleotide bases other than adenine, guanine, cytosine and uracil at 1' position or their equivalents; such bases may be used within the catalytic core of an enzymatic nucleic acid molecule and/or in the substrate-binding regions of such a molecule. Such modified nucleotides include dideoxynucleotides which have pharmaceutical utility well known in the art, as well as utility in basic molecular biology methods such as sequencing.

By "unmodified nucleoside" or "unmodified nucleotide" is meant one of the bases adenine, cytosine, guanine, uracil joined to the 1' carbon of β-D-ribo-furanose.

By "modified nucleoside" or "modified nucleotide" is meant any nucleotide base which contains a modification in the chemical structure of an unmodified nucleotide base, sugar and/or phosphate.

By "pyrimidines" is meant nucleotides comprising modified or unmodified derivatives of a six membered pyrimidine ring. An example of a pyrimidine is modified or unmodified uridine.

By "nucleotide triphosphate" or "NTP" is meant a nucleoside bound to three inorganic phosphate groups at the 5' hydroxyl group of the modified or unmodified ribose or deoxyribose sugar where the 1' position of the sugar may comprise a nucleic acid base or hydrogen. The triphosphate portion may be modified to include chemical moieties which do not destroy the functionality of the group (i.e., allow incorporation into an RNA molecule).

In another preferred embodiment, nucleotide triphosphates (NTPs) of the instant invention are incorporated into an oligonucleotide using an RNA polymerase enzyme. RNA polymerases include but are not limited to mutated and wild type versions of bacteriophage T7, SP6, or T3 RNA polymerases. Applicant has also found that the NTPs of the present invention can be incorporated into oligonucleotides using certain DNA polymerases, such as Taq polymerase.

In yet another preferred embodiment, the invention features a process for incorporating modified NTP's into an oligonucleotide including the step of incubating a mixture having a DNA template, RNA polymerase, NTP, and an enhancer of modified NTP incorporation under conditions suitable for the incorporation of the modified NTP into the oligonucleotide.

By "enhancer of modified NTP incorporation" is meant a reagent which facilitates the incorporation of modified nucleotides into a nucleic acid transcript by an RNA polymerase. Such reagents include but are not limited to methanol; LiCl; polyethylene glycol (PEG); diethyl ether; propanol; methyl amine; ethanol and the like.

In another preferred embodiment, the modified nucleotide triphosphates can be incorporated by transcription into a nucleic acid molecules including enzymatic nucleic acid, antisense, 2-5A antisense chimera, oligonucleotides, triplex forming oligonucleotide (TFO), aptamers and the like (Stull et al., 1995 *Pharmaceutical Res.* 12, 465).

By "antisense" it is meant a non-enzymatic nucleic acid molecule that binds to target RNA by means of RNA—RNA or RNA-DNA or RNA-PNA (protein nucleic acid; Egholm et al., 1993 *Nature* 365, 566) interactions and alters the activity of the target RNA (for a review see Stein and Cheng, 1993 *Science* 261, 1004; Agrawal et al., U.S. Pat. No. 5,591,721; Agrawal, U.S. Pat. No. 5,652,356). Typically, antisense molecules will be complementary to a target sequence along a single contiguous sequence of the antisense molecule. However, in certain embodiments, an antisense molecule may bind to substrate such that the substrate molecule forms a loop, and/or an antisense molecule may bind such that the antisense molecule forms a loop. Thus, the antisense molecule may be complementary to two (or even more) non-contiguous substrate sequences or two (or even more) non-contiguous sequence portions of an antisense molecule may be complementary to a target sequence or both.

By "2-5A antisense chimera" it is meant, an antisense oligonucleotide containing a 5' phosphorylated 2'-5'-linked adenylate residues. These chimeras bind to target RNA in a sequence-specific manner and activate a cellular 2-5A-dependent ribonuclease which, in turn, cleaves the target RNA (Torrence et al., 1993 *Proc. Natl. Acad. Sci. USA* 90, 1300).

By "triplex forming oligonucleotides (TFO)" it is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504).

By "oligonucleotide" as used herein is meant a molecule having two or more nucleotides. The polynucleotide can be single, double or multiple stranded and may have modified or unmodified nucleotides or non-nucleotides or various mixtures and combinations thereof.

By "nucleic acid catalyst" is meant a nucleic acid molecule capable of catalyzing (altering the velocity and/or rate of) a variety of reactions including the ability to repeatedly cleave other separate nucleic acid molecules (endonuclease activity) in a nucleotide base sequence-specific manner. Such a molecule with endonuclease activity may have complementarity in a substrate binding region to a specified gene target, and also has an enzymatic activity that specifically cleaves RNA or DNA in that target. That is, the nucleic acid molecule with endonuclease activity is able to intramolecularly or intermolecularly cleave RNA or DNA and thereby inactivate a target RNA or DNA molecule. This complementarity functions to allow sufficient hybridization of the enzymatic RNA molecule to the target RNA or DNA to allow the cleavage to occur. 100% complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, catalytic oligonucleotides, nucleozyme, DNAzyme, RNA enzyme, endoribonuclease, endonuclease, minizyme, leadzyme, oligozyme, finderon or DNA enzyme. All of these terminologies describe nucleic acid molecules with enzymatic activity. The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving activity to the molecule (Cech et al., U.S. Pat. No. 4,987,071; Cech et al., 1988, 260 *JAMA* 3030).

By "enzymatic portion" or "catalytic domain" is meant that portion/region of the enzymatic nucleic acid molecule essential for cleavage of a nucleic acid substrate.

By "substrate binding arm" or "substrate binding domain" is meant that portion/region of a enzymatic nucleic acid molecule which is complementary to (i.e., able to base-pair with) a portion of its substrate. Generally, such complementarity is 100%, but can be less if desired. For example, as few as 10 bases out of 14 may be base-paired. That is, these arms contain sequences within a enzymatic nucleic acid molecule which are intended to bring enzymatic nucleic acid molecule and target together through complementary base-pairing interactions. The enzymatic nucleic acid molecule of the invention may have binding arms that are contiguous or non-contiguous and may be varying lengths. The length of the binding arm(s) are preferably greater than or equal to four nucleotides; specifically 12–100 nucleotides; more specifically 14–24 nucleotides long. If two binding arms are chosen, the design is such that the length of the binding arms are symmetrical (i.e., each of the binding arms is of the same length; e.g., five and five nucleotides, six and six nucleotides or seven and seven nucleotides long) or asymmetrical (i.e., the binding arms are of different length; e.g., six and three nucleotides; three and six nucleotides long; four and five nucleotides long; four and six nucleotides long; four and seven nucleotides long; and the like).

By "nucleic acid molecule" as used herein is meant a molecule having nucleotides. The nucleic acid can be single, double or multiple stranded and may comprise modified or unmodified nucleotides or non-nucleotides or various mixtures and combinations thereof. An example of a nucleic acid molecule according to the invention is a gene which encodes for macromolecule such as a protein.

In preferred embodiments of the present invention, a nucleic acid molecule, e.g., an antisense molecule, a triplex DNA, or an enzymatic nucleic acid molecule, is 13 to 100 nucleotides in length, e.g., in specific embodiments 35, 36, 37, or 38 nucleotides in length (e.g., for particular ribozymes). In particular embodiments, the nucleic acid molecule is 15–100, 17–100, 20–100, 21–100, 23–100, 25–100, 27–100, 30–100, 32–100, 35–100, 40–100, 50–100, 60–100, 70–100, or 80–100 nucleotides in length. Instead of 100 nucleotides being the upper limit on the length ranges specified above, the upper limit of the length range can be, for example, 30, 40, 50, 60, 70, or 80 nucleotides. Thus, for any of the length ranges, the length range for particular embodiments has lower limit as specified, with an upper limit as specified which is greater than the lower limit. For example, in a particular embodiment, the length range can be 35–50 nucleotides in length. All such ranges are expressly included. Also in particular embodiments, a nucleic acid molecule can have a length which is any of the lengths specified above, for example, 21 nucleotides in length.

By "complementarity" is meant that a nucleic acid can form hydrogen bond(s) with another RNA sequence by either traditional Watson-Crick or other non-traditional types. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, antisense or triple helix inhibition. Determination of binding free energies for nucleic acid molecules is well-known in the art (see, e.g., Turner et al., 1987, CSH Symp. Quant. Biol. LII pp.123–133; Frier et al., 1986, Proc. Nat. Acad. Sci. USA 83:9373–9377; Turner et al., 1987, J. Am. Chem. Soc. 109:3783–3785. A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

In yet another preferred embodiment, the modified nucleotide triphosphates of the instant invention can be used for combinatorial chemistry or in vitro selection of nucleic acid molecules with novel function. Modified oligonucleotides can be enzymatically synthesized to generate libraries for screening.

In another preferred embodiment, the invention features nucleic acid based techniques (e.g., enzymatic nucleic acid molecules), antisense nucleic acids, 2-5A antisense chimeras, triplex DNA, antisense nucleic acids containing RNA cleaving chemical groups) isolated using the methods described in this invention and methods for their use to diagnose, down regulate or inhibit gene expression.

By "inhibit" it is meant that the activity of target genes or level of mRNAs or equivalent RNAs encoding target genes is reduced below that observed in the absence of the nucleic acid molecules of the instant invention (e.g., enzymatic nucleic acid molecules), antisense nucleic acids, 2-5A antisense chimeras, triplex DNA, antisense nucleic acids containing RNA cleaving chemical groups). In one embodiment, inhibition with enzymatic nucleic acid molecule preferably is below that level observed in the presence of an enzymatically attenuated nucleic acid molecule that is able to bind to the same site on the mRNA, but is unable to cleave that RNA. In another embodiment, inhibition with nucleic acid molecules, including enzymatic nucleic acid and antisense molecules, is preferably greater than that observed in the presence of for example, an oligonucleotide with scrambled sequence or with mismatches. In another embodiment, inhibition of target genes with the nucleic acid molecule of the instant invention is greater than in the presence of the nucleic acid molecule than in its absence.

In yet another preferred embodiment, the invention features a process for the incorporating a plurality of compounds of formula I.

In yet another embodiment, the invention features a nucleic acid molecule with catalytic activity having formula II:

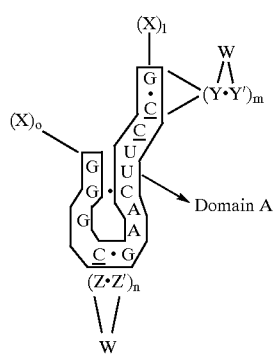

In the formula shown above X, Y, and Z represent independently a nucleotide or a non-nucleotide linker, which may be same or different; • indicates hydrogen bond formation between two adjacent nucleotides; Y' is a nucleotide complementary to Y; Z' is a nucleotide complementary to Z; l is an integer greater than or equal to 3 and preferably less than 20, more specifically 4, 5, 6, 7, 8, 9, 10, 11, 12, or 15; m is an integer greater than 1 and preferably less than 10, more specifically 2, 3, 4, 5, 6, or 7; n is an integer greater than 1 and preferably less than 10, more specifically 3, 4, 5, 6, or 7; o is an integer greater than or equal to 3 and preferably less than 20, more specifically 3, 4, 5, 6, 7, 8, 9, 10, 11, 12, or 15; l and o may be the same length (l=o) or different lengths (l≠o); each X(l) and X(o) are oligonucleotides which are of sufficient length to stably interact independently with a target nucleic acid sequence (the target can be an RNA, DNA or RNA/DNA mixed polymers); W is a linker or ≧2 nucleotides in length or may be a non-nucleotide linker; A, U, C, and G represent the nucleotides; G is a nucleotide, preferably 2'-O-methyl; C represents a nucleotide, preferably 2'-amino (e.g., 2'-NH$_2$ or 2'-O—NH$_2$, and represents a chemical linkage (e.g. a phosphate ester linkage, amide linkage, phosphorothioate, phosphorodithioate or others known in the art).

The enzymatic nucleic acid molecule of Formula II may independently comprise a cap structure which may independently be present or absent.

By "sufficient length" is meant an oligonucleotide of greater than or equal to 3 nucleotides.

By "stably interact" is meant, interaction of the oligonucleotides with target nucleic acid (e.g., by forming hydrogen bonds with complementary nucleotides in the target under physiological conditions).

By "chimeric nucleic acid molecule" or "chimeric oligonucleotide" is meant that, the molecule may be comprised of both modified or unmodified DNA or RNA.

By "cap structure" is meant chemical modifications, which have been incorporated at the terminus of the oligonucleotide. These terminal modifications protect the nucleic acid molecule from exonuclease degradation, and may help in delivery and/or localization within a cell. The cap may be present at the 5'-terminus (5'-cap) or at the 3'-terminus (3'-cap) or may be present on both termini. In non-limiting examples: the 5'-cap is selected form the group comprising inverted abasic residue (moiety); 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3' inverted nucleotide moiety; 3'-3'-inverted abasic moiety; 3',2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Beigelman et al., International PCT publication No. WO 97/26270). In yet another preferred embodiment the 3'-cap is selected from a group comprising, 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non-bridging methylphosphonate and 5'-mercapto moieties (for more details see Beaucage and Iyer, 1993, tetrahedron 49, 1925). By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine. The terms "abasic" or "abasic nucleotide" as used herein encompass sugar moieties lacking a base or having other chemical groups in place of base at the 1' position.

In connection with 2'-modified nucleotides as described for the present invention, by "amino" is meant 2'-NH$_2$ or 2'-O—NH$_2$, which may be modified or unmodified. Such modified groups are described, for example, in Eckstein et al., U.S. Pat. No. 5,672,695 and Matulic-Adamic et al., WO 98/28317, respectively, which are both incorporated by reference in their entireties.

DESCRIPTION OF THE PREFERRED EMBODIMENTS

The drawings will first briefly be described.
Drawings:

FIG. 1 displays a schematic representation of NTP synthesis using nucleoside substrates.

FIG. 2 shows a scheme for an in vitro selection method. A pool of nucleic acid molecules is generated with a random core region and one or more region(s) with a defined sequence. These nucleic acid molecules are bound to a column containing immobilized oligonucleotide with a defined sequence, where the defined sequence is complementary to region(s) of defined sequence of nucleic acid molecules in the pool. Those nucleic acid molecules capable of cleaving the immobilized oligonucleotide (target) in the column are isolated and converted to complementary DNA (cDNA), followed by transcription using NTPs to form a new nucleic acid pool.

FIG. 3 shows a scheme for a two column in vitro selection method. A pool of nucleic acid molecules is generated with a random core and two flanking regions (region A and region B) with defined sequences. The pool is passed through a column which has immobilized oligonucleotides with regions A' and B' that are complementary to regions A and B of the nucleic acid molecules in the pool, respectively. The column is subjected to conditions sufficient to facilitate cleavage of the immobilized oligonucleotide target. The molecules in the pool that cleave the target (active molecules) have A' region of the target bound to their A region, whereas the B region is free. The column is washed to isolate the active molecules with the bound A' region of the target. This pool may of active molecules may also contain some molecules that are not active to cleave the target (inactive molecules) but have dissociated from the column. To separate the contaminating inactive molecules from the active molecules, the pool is passed through a second column (column 2) which contains immobilized oligonucleotides with the A' sequence but not the B' sequence. The inactive molecules will bind to column 2 but the active molecules will not bind to column 2 because their A region is occupied by the A' region of the target oligonucleotide from column 1. The column 2 is washed to isolate the active molecules for further processing as described under FIG. 2 scheme.

FIG. 4 is a diagram of a novel 48 nucleotide enzymatic nucleic acid motif which was identified using in vitro methods described in the instant invention. The molecule shown is only exemplary. The 5' and 3' terminal nucleotides (referring to the nucleotides of the substrate binding arms rather than merely the single terminal nucleotide on the 5' and 3' ends) can be varied so long as those portions can base-pair with target substrate sequence. In addition, the guanosine (G) shown at the cleavage site of the substrate can be changed to other nucleotides so long as the change does not eliminate the ability of enzymatic nucleic acid molecules to cleave the target sequence. Substitutions in the nucleic acid molecule and/or in the substrate sequence can be readily tested, for example, as described herein.

FIG. 5 is a schematic diagram of Hepatitis C Virus (HCV) luciferase assay used to demonstrate efficacy of class I enzymatic nucleic acid molecule motif.

FIG. 6 is a graph indicating the dose curve of an enzymatic nucleic acid molecule targeting site 146 on HCV RNA.

FIG. 7 is a bar graph showing enzymatic nucleic acid molecules targeting 4 sites within the HCV RNA are able to reduce RNA levels in cells.

FIGS. 8a and 8b show secondary structures for characterized Class II enzymatic nucleic acid motifs. Cleavage rates (min$^{-1}$) for FIG. 8a: Molecule A1=0.05, Molecule A5=0.03, Molecule B2=0.11; FIG. 8b: Molecule B6=0.10, Molecule B23=0.05, Molecule C5=0.01. The NTP used in these assays was 2'-NH$_2$-CTP.

NUCLEOTIDE SYNTHESIS

Addition of dimethylaminopyridine (DMAP) to the phosphorylation protocols known in the art can greatly increase the yield of nucleotide monophosphates while decreasing the reaction time (FIG. 1). Synthesis of the nucleosides of the invention have been described in several publications and Applicants previous applications (Beigelman et al., International PCT publication No. WO 96/18736; Dudzcy et al., Int. PCT Pub. No. WO 95/11910; Usman et al., Int. PCT Pub. No. WO 95/13378; Matulic-Adamic et al., 1997, Tetrahedron Lett. 38, 203; Matulic-Adamic et al., 1997, Tetrahedron Lett. 38, 1669; all of which are incorporated herein by reference). These nucleosides are dissolved in triethyl phosphate and chilled in an ice bath. Phosphorus oxychloride (POCl$_3$) is then added followed by the introduction of DMAP. The reaction is then warmed to room temperature and allowed to proceed for 5 hours. This reaction allows the formation of nucleotide monophosphates which can then be used in the formation of nucleotide triphosphates. Tributylamine is added followed by the addition of anhydrous acetonitrile and tributylammonium pyrophosphate. The reaction is then quenched with TEAB and stirred overnight at room temperature (about 20° C.). The triphosphate is purified using column purification and HPLC and the chemical structure is confirmed using NMR analysis. Those skilled in the art will recognize that the reagents, temperatures of the reaction, and purification methods can easily be alternated with substitutes and equivalents and still obtain the desired product.

Nucleotide Triphosphates

The invention provides nucleotide triphosphates which can be used for a number of different functions. The nucleotide triphosphates formed from nucleosides found in table I are unique and distinct from other nucleotide triphosphates known in the art. Incorporation of modified nucleotides into DNA or RNA oligonucleotides can alter the properties of the molecule. For example, modified nucleotides can hinder binding of nucleases, thus increasing the chemical half-life of the molecule. This is especially important if the molecule is to be used for cell culture or in vivo. It is known in the art that the introduction of modified nucleotides into these molecules can greatly increase the stability and thereby the effectiveness of the molecules (Burgin et al., 1996, *Biochemistry* 35, 14090–14097; Usman et al., 1996, *Curr. Opin. Struct. Biol.* 6, 527–533).

Modified nucleotides are incorporated using either wild type and mutant polymerases. For example, mutant T7 polymerase is used in the presence of modified nucleotide triphosphate(s), DNA template and suitable buffers. Those skilled in the art will recognize that other polymerases and their respective mutant versions can also be utilized for the incorporation of NTP's of the invention. Nucleic acid transcripts were detected by incorporating radiolabelled nucleotides ($\alpha$-$^{32}$P NTP). The radiolabeled NTP contained the same base as the modified triphosphate being tested. The effects of methanol, PEG and LiCl were tested by adding these compounds independently or in combination. Detection and quantitation of the nucleic acid transcripts was performed using a Molecular Dynamics PhosphorImager. Efficiency of transcription was assessed by comparing modified nucleotide triphosphate incorporation with all-ribonucleotide incorporation control. Wild type polymerase was used to incorporate NTP's using the manufacturer's buffers and instructions (Boehringer Mannheim).

Transcription Conditions

Incorporation rates of modified nucleotide triphosphates into oligonucleotides can be increased by adding to traditional buffer conditions, several different enhancers of modified NTP incorporation. Applicant has utilized methanol and LiCl in an attempt to increase incorporation rates of dNTP using RNA polymerase. These enhancers of modified NTP incorporation can be used in different combinations and ratios to optimize transcription. Optimal reaction conditions differ between nucleotide triphosphates and can readily be determined by standard experimentation. Overall however, inclusion of enhancers of modified NTP incorporation such as methanol or inorganic compound such as lithium chloride, have been shown by the applicant to increase the mean transcription rates.

Mechanism of Action of Nucleic Acid Molecules of the Invention

Antisense: Antisense molecules may be modified or unmodified RNA, DNA, or mixed polymer oligonucleotides and primarily function by specifically binding to matching sequences resulting in inhibition of peptide synthesis (Wu-Pong, November 1994, *BioPharm*, 20–33). The antisense oligonucleotide binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm (Mukhopadhyay & Roth, 1996, *Crit. Rev. in Oncogenesis* 7, 151–190).

In addition, binding of single stranded DNA to RNA may result in nuclease degradation of the heteroduplex (Wu-Pong, supra; Crooke, supra). To date, the only backbone modified DNA chemistry which will act as substrates for RNase H are phosphorothioates and phosphorodithioates. Recently it has been reported that 2'-arabino and 2'-fluoro arabino-containing oligos can also activate RNase H activity.

A number of antisense molecules have been described that utilize novel configurations of chemically modified nucleotides, secondary structure, and/or RNase H substrate domains (Woolf et al., International PCT Publication No. WO 98/13526; Thompson et al., U.S. Ser. No. 60/082,404 which was filed on Apr. 20, 1998; Hartmann et al., U.S. Ser. No. 60/101,174 which was filed on Sep. 21, 1998) all of these are incorporated by reference herein in their entirety.

Triplex Forming Oligonucleotides (TFO): Single stranded DNA may be designed to bind to genomic DNA in a sequence specific manner. TFOs are comprised of pyrimidine-rich oligonucleotides which bind DNA helices through Hoogsteen Base-pairing (Wu-Pong, supra). The resulting triple helix composed of the DNA sense, DNA antisense, and TFO disrupts RNA synthesis by RNA polymerase. The TFO mechanism may result in gene expression or cell death since binding may be irreversible (Mukhopadhyay & Roth, supra)

2-5A Antisense Chimera: The 2-5A system is an interferon-mediated mechanism for RNA degradation found in higher vertebrates (Mitra et al., 1996, *Proc Nat Acad Sci USA* 93, 6780–6785). Two types of enzymes, 2-5A synthetase and RNase L, are required for RNA cleavage. The 2-5A synthetases require double stranded RNA to form 2'-5' oligoadenylates (2-5A). 2-5A then acts as an allosteric effector for utilizing RNase L which has the ability to cleave single stranded RNA. The ability to form 2-5A structures with double stranded RNA makes this system particularly useful for inhibition of viral replication. (2'-5') oligoadenylate structures may be covalently linked to antisense molecules to form chimeric oligonucleotides capable of RNA cleavage (Torrence, supra). These molecules putatively bind and activate a 2-5A dependent RNase, the oligonucleotide/enzyme complex then binds to a target RNA molecule which can then be cleaved by the RNase enzyme.

Enzymatic Nucleic Acid: In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of an enzymatic nucleic acid has significant advantages, such as the concentration of enzymatic nucleic acid molecules necessary to affect a therapeutic treatment is lower. This advantage reflects the ability of the enzymatic nucleic acid molecules to act enzymatically. Thus, a single enzymatic nucleic acid molecule is able to cleave many molecules of target RNA. In addition, the enzymatic nucleic acid molecule is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to completely eliminate catalytic activity of enzymatic nucleic acid molecules.

Nucleic acid molecules having an endonuclease enzymatic activity are able to repeatedly cleave other separate RNA molecules in a nucleotide base sequence-specific manner. Such enzymatic nucleic acid molecules can be targeted to virtually any RNA transcript, and efficient cleavage achieved in vitro (Zaug et al., 324, *Nature* 429 1986; Uhlenbeck, 1987 *Nature* 328, 596; Kim et al., 84 *Proc. Natl. Acad. Sci. USA* 8788, 1987; Dreyfus, 1988, *Einstein Quart. J. Bio. Med.*, 6, 92; Haseloff and Gerlach, 334 *Nature* 585, 1988; Cech, 260 *JAMA* 3030, 1988; and Jefferies et al., 17 *Nucleic Acids Research* 1371, 1989; Santoro et al., 1997 supra).

Because of their sequence-specificity, trans-cleaving enzymatic nucleic acid molecules show promise as therapeutic agents for human disease (Usman & McSwiggen, 1995 *Ann. Rep. Med. Chem.* 30, 285–294; Christoffersen and Marr, 1995 *J. Med. Chem.* 38, 2023–2037). Enzymatic nucleic acid molecules can be designed to cleave specific RNA targets within the background of cellular RNA. Such a cleavage event renders the RNA non-functional and abrogates protein expression from that RNA. In this manner, synthesis of a protein associated with a disease state can be selectively inhibited.

Optimizing Nucleic Acid Catalyst Activity

Catalytic activity of the enzymatic nucleic acid molecules described and identified using the methods of the instant invention, can be optimized as described by Draper et al., supra and using the methods well known in the art. The details will not be repeated here, but include altering the length of the enzymatic nucleic acid molecules' binding arms, or chemically synthesizing enzymatic nucleic acid molecules with modifications (base, sugar and/or phosphate) that prevent their degradation by serum ribonucleases and/or enhance their enzymatic activity (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; Rossi et al., International Publication No. WO 91/03162; Sproat, U.S. Pat. No. 5,334,711; and Burgin et al., supra, all of these describe various chemical modifications that can be made to the base, phosphate and/or sugar moieties of enzymatic nucleic acid molecules). Modifications which enhance their efficacy in cells, and removal of bases from stem loop structures to shorten synthesis times and reduce chemical requirements are desired. (All these publications are hereby incorporated by reference herein).

There are several examples in the art describing sugar, base and phosphate modifications that can be introduced into nucleic acid molecules (e.g., enzymatic nucleic acid molecules) without significantly effecting catalysis and with significant enhancement in their nuclease stability and efficacy. Enzymatic nucleic acid molecules are modified to enhance stability and/or enhance catalytic activity by modification with nuclease resistant groups, for example, 2'-amino, 2'-C-allyl, 2'-fluoro, 2'-O-methyl, 2'-H, nucleotide base modifications (for a review see Usman and Cedergren, 1992 *TIBS* 17, 34; Usman et al., 1994 *Nucleic Acids Symp. Ser.* 31, 163; Burgin et al., 1996 *Biochemistry* 35, 14090). Sugar modification of enzymatic nucleic acid molecules have been extensively described in the art (see Eckstein et al., International Publication PCT No. WO 92/07065; Perrault et al. *Nature* 1990, 344, 565–568; Pieken et al. *Science* 1991, 253, 314–317; Usman and Cedergren, *Trends in Biochem. Sci.* 1992, 17, 334–339; Usman et al. International Publication PCT No. WO 93/15187; Sproat, U.S. Pat. No. 5,334,711 and Beigelman et al., 1995 *J. Biol. Chem.* 270, 25702; all of the references are hereby incorporated in their totality by reference herein). Such publications describe general methods and strategies to determine the location of incorporation of sugar, base and/or phosphate modifications and the like into s without inhibiting catalysis, and are incorporated by reference herein. In view of such teachings, similar modifications can be used as described herein to modify the nucleic acid catalysts of the instant invention.

Nucleic acid catalysts having chemical modifications which maintain or enhance enzymatic activity are provided. Such nucleic acid molecules are generally more resistant to nucleases than unmodified nucleic acid. Thus, in a cell and/or in vivo the activity may not be significantly lowered. As exemplified herein such enzymatic nucleic acid molecules are useful in a cell and/or in vivo even if activity over all is reduced 10 fold (Burgin et al., 1996, *Biochemistry*, 35, 14090). Such enzymatic nucleic acid molecules herein are said to "maintain" the enzymatic activity.

Therapeutic nucleic acid molecules (e.g., enzymatic nucleic acid molecules and antisense nucleic acid molecules) delivered exogenously must optimally be stable within cells until translation of the target RNA has been inhibited long enough to reduce the levels of the undesirable protein. This period of time varies between hours to days depending upon the disease state. Clearly, these nucleic acid molecules must be resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

By "enhanced enzymatic activity" is meant to include activity measured in cells and/or in vivo where the activity is a reflection of both catalytic activity and enzymatic nucleic acid molecules stability. In this invention, the product of these properties is increased or not significantly (less that 10 fold) decreased in vivo compared to an unmodified enzymatic nucleic acid molecules.

In yet another preferred embodiment, nucleic acid catalysts having chemical modifications which maintain or enhance enzymatic activity is provided. Such nucleic acid is also generally more resistant to nucleases than unmodified nucleic acid. Thus, in a cell and/or in vivo the activity may not be significantly lowered. As exemplified herein such enzymatic nucleic acid molecules are useful in a cell and/or in vivo even if activity over all is reduced 10 fold (Burgin et al., 1996, *Biochemistry*, 35, 14090). Such enzymatic nucleic acid molecules herein are said to "maintain" the enzymatic activity on all RNA enzymatic nucleic acid molecule.

Use of these molecules will lead to better treatment of the disease progression by affording the possibility of combination therapies (e.g., multiple enzymatic nucleic acid molecules targeted to different genes, enzymatic nucleic acid molecules coupled with known small molecule inhibitors, or intermittent treatment with combinations of enzymatic nucleic acid molecules (including different enzymatic nucleic acid molecules motifs) and/or other chemical or biological molecules). The treatment of patients with nucleic acid molecules may also include combinations of different types of nucleic acid molecules. Therapies may be devised which include a mixture of enzymatic nucleic acid molecules (including different enzymatic nucleic acid molecules motifs), antisense and/or 2-5A chimera molecules to one or more targets to alleviate symptoms of a disease.

Administration of Nucleotide Mono, Di or Triphosphates and Nucleic Acid Molecules The nucleotide monophosphates, diphosphates, or triphosphates or the nucleic acid molecules of the instant invention, can be used as a therapeutic agent either independently or in combination with other pharmaceutical components. These molecules of the inventions can be administered to patients using the methods of Sullivan et al., PCT WO 94/02595 Akhtar et al., 1992, *Trends Cell Bio.*, 2, 139; and *Delivery Strategies for Antisense Oligonucleotide Therapeutics*, ed. Akhtar, 1995 which are both incorporated herein by reference. Molecules of the invention may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, enzymatic nucleic acid molecules may be directly delivered ex vivo to cells or tissues with or without the aforementioned vehicles. Alternatively, the modified nucleotide triphosphate, diphosphate or monophosphate/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of delivery and administration are provided in Sullivan et al., supra and Draper et al., PCT WO93/23569 which have been incorporated by reference herein.

The molecules of the instant invention can be used as pharmaceutical agents. Pharmaceutical agents prevent, inhibit the occurrence, or treat (alleviate a symptom to some extent, preferably all of the symptoms) of a disease state in a patient.

The negatively charged nucleotide mono, di or triphosphates of the invention can be administered and introduced into a patient by any standard means, with or without stabilizers, buffers, and the like, to form a pharmaceutical composition. When it is desired to use a liposome delivery mechanism, standard protocols for formation of liposomes can be followed. The compositions of the present invention may also be formulated and used as tablets, capsules or elixirs for oral administration; suppositories for rectal administration; sterile solutions; suspensions for injectable administration; and the like.

The present invention also includes pharmaceutically acceptable formulations of the compounds described. These formulations include salts of the above compounds, e.g., ammonium, sodium, calcium, magnesium, lithium, and potassium salts.

A pharmacological composition or formulation refers to a composition or formulation in a form suitable for administration, e.g., systemic administration, into a cell or patient, preferably a human. Suitable forms, in part, depend upon the use or the route of entry, for example oral, transdermal, or by injection. Such forms should not prevent the composition or formulation to reach a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

By "systemic administration" is meant in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary and intramuscular. Each of these administration routes expose the desired negatively charged polymers, e.g., NTP's, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful. This approach may provide enhanced delivery of the drug to target cells by taking advantage of the specificity of macrophage and lymphocyte immune recognition of abnormal cells, such as the cancer cells.

The invention also features the use of the a composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601–2627; Ishiwata et al., *Chem. Pharm. Bull.* 1995, 43, 1005–1011). Such liposomes have been shown to accumulate selectively in tumors, presumably by extravasation and capture in the neovascularized target tissues (Lasic et al., *Science* 1995, 267, 1275–1276; Oku et al., 1995, *Biochim. Biophys. Acta*, 1238, 86–90). The long-circulating liposomes enhance the pharmacokinetics and pharmacodynamics of drugs, particularly compared to conventional cationic liposomes which are known to accumulate in tissues of the MPS (Liu et al., *J. Biol. Chem.* 1995, 42, 24864–24870; Choi et al., International PCT Publication No. WO 96/10391; Ansell et al., International PCT Publication No. WO 96/10390; Holland et al., International PCT Publication No. WO 96/10392; all of these are incorporated by reference herein). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985) hereby incorporated by reference herein. For example, preservatives, stabilizers, dyes and flavoring agents may be provided. Id. at 1449. These include sodium benzoate, sorbic acid and esters of p-hydroxybenzoic acid. In addition, antioxidants and suspending agents may be used.

By "patient" is meant an organism which is a donor or recipient of explanted cells or the cells themselves. "Patient" also refers to an organism to which the compounds of the invention can be administered. Preferably, a patient is a mammal, e.g., a human, primate or a rodent.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer. In a one aspect, the invention provides enzymatic nucleic acid molecules that can be delivered exogenously to specific cells as required.

The nucleic acid molecules of the present invention may also be administered to a patient in combination with other therapeutic compounds to increase the overall therapeutic effect. The use of multiple compounds to treat an indication may increase the beneficial effects while reducing the presence of side effects.

EXAMPLES

The following are non-limiting examples showing the synthesis, incorporation and analysis of nucleotide triphosphates and activity of enzymatic nucleic acids of the instant invention.

Applicant synthesized pyrimidine nucleotide triphosphates using DMAP in the reaction. For purines, applicant utilized standard protocols previously described in the art (Yoshikawa et al supra; Ludwig, supra). Described below is one example of a pyrimdine nucleotide triphosphate and one purine nucleotide triphosphate synthesis.

Example 1

Synthesis of Purine Nucleotide Triphosphates: 2'-O-Methyl-guanosine-5'-triphosphate 2'-O-methyl guanosine nucleoside (0.25 grams, 0.84 mmol) was dissolved in triethyl phosphate (5.0) ml by heating to 100° C. for 5 minutes. The resulting clear, colorless solution was cooled to 0° C. using an ice bath under an argon atmosphere. Phosphorous oxychloride (1.8 eq., 0.141 ml) was then added to the reaction mixture with vigorous stirring. The reaction was monitored by HPLC, using a sodium perchlorate gradient. After 5 hours at 0° C., tributylamine (0.65 ml) was added followed by the addition of anhydrous acetonitrile (10.0 ml), and after 5 minutes (reequilibration to 0° C.) tributylammonium pyrophosphate (4.0 eq., 1.53 g) was added. The reaction mixture was quenched with 20 ml of 2M TEAB after 15 minutes at 0° C. (HPLC analysis with above conditions showed consumption of monophosphate at 10 minutes) then stirred overnight at room temperature, the mixture was evaporated in vacuo with methanol co-evaporation (4x) then diluted in 50 ml 0.05M TEAB. DEAE sephadex purification was used with a gradient of 0.05 to 0.6 M TEAB to obtain pure triphosphate (0.52 g, 66.0% yield) (elutes around 0.3M TEAB); the purity was confirmed by HPLC and NMR analysis.

Example 2

Synthesis of Pyrimidine Nucleotide Triphosphates: 2'-O-Methylthiomethyl-uridine-5'-triphosphate 2'-O-methylthiomethyl uridine nucleoside (0.27 grams, 1.0 mmol) was dissolved in triethyl phosphate (5.0 ml). The resulting clear, colorless solution was cooled to 0° C. with an ice bath under an argon atmosphere. Phosphorus oxychloride (2.0 eq., 0.190 ml) was then added to the reaction mixture with vigorous stirring. Dimethylaminopyridine (DMAP, 0.2 eq., 25 mg) was added, the solution warmed to room temperature and the reaction was monitored by HPLC, using a sodium perchlorate gradient. After 5 hours at 20° C., tributylamine (1.0 ml) was added followed by anhydrous acetonitrile (10.0 ml), and after 5 minutes tributylammonium pyrophosphate (4.0 eq., 1.8 g) was added. The reaction mixture was quenched with 20 ml of 2M TEAB after 15 minutes at 20° C. (HPLC analysis with above conditions showed consumption of monophosphate at 10 minutes) then stirred overnight at room temperature. The mixture was evaporated in vacuo with methanol co-evaporation (4x) then diluted in 50 ml 0.05M TEAB. DEAE fast flow Sepharose purification with a gradient of 0.05 to 1.0 M TEAB was used to obtain pure triphosphate (0.40 g, 44% yield) (elutes around 0.3M TEAB) as determined by HPLC and NMR analysis.

Example 3

Utilization of Deoxymethylaminopyridine (DMAP) in Uridine 5'-Triphosphate Synthesis The reactions were performed on 20 mg aliquots of nucleoside dissolved in 1 ml of triethyl phosphate and 10 ul of phosphorus oxychloride. The reactions were monitored at 40 minute intervals automatically by HPLC to generate yield-of-product curves at times up to 18 hours. A reverse phase column and ammonium acetate/sodium acetate buffer system (50 mM & 100 mM, respectively, at pH 4.2) was used to separate the 5', 3', 2' monophosphates (the monophosphates elute in that order) from the 5'-triphosphate and the starting nucleoside. The data is shown in table 2. These conditions doubled the product yield and resulted in a 10-fold improvement in the reaction time to maximum yield (1200 minutes down to 120 minutes for a 90% yield). Selectivity for 5'-monophophorylation was observed for all reactions. Subsequent triphosphorylation occurred in nearly quantitative yield.

Materials Used in Bacteriophage T7 RNA Polymerase Reactions

Buffer 1: Reagents are mixed together to form a 10x stock solution of buffer 1 (400 mM Tris-Cl (pH 8.1), 200 mM $MgCl_2$, 100 mM DTT, 50 mM spermidine, and 0.1% triton X-100. Prior to initiation of the polymerase reaction methanol, LiCl is added and the buffer is diluted such that the final reaction conditions for condition 1 consisted of: 40 mM tris pH (8.1), 20 mM $MgCl_2$, 10 mM DTT, 5 mM spermidine, 0.01% triton X-100, 10% methanol, and 1 mM LiCl.

BUFFER 2: Reagents are mixed together to form a 10x stock solution of buffer 2(400 mM Tris-Cl (pH 8.1), 200 mM $MgCl_2$, 100 mM DTT, 50 mM spermidine, and 0.1% triton X-100. Prior to initiation of the polymerase reaction PEG, LiCl is added and the buffer is diluted such that the final reaction conditions for buffer 2 consisted of: 40 mM tris pH (8.1), 20 mM $MgCl_2$, 10 mM DTT, 5 mM spermidine, 0.01% triton X-100, 4% PEG, and 1 mM LiCl.

BUFFER 3: Reagents are mixed together to form a 10x stock solution of buffer 3 (400 mM Tris-Cl (pH 8.0), 120 mM $MgCl_2$, 50 mM DTT, 10 mM spermidine and 0.02% triton X-100. Prior to initiation of the polymerase reaction PEG is added and the buffer is diluted such that the final reaction conditions for buffer 3 consisted of: 40 mM tris pH (8.0), 12 mM $MgCl_2$, 5 mM DTT, 1 mM spermidine, 0.002% triton X-100, and 4% PEG.

BUFFER 4: Reagents are mixed together to form a 10x stock solution of buffer 4 (400 mM Tris-Cl (pH 8.0), 120 mM $MgCl_2$, 50 mM DTT, 10 mM spermidine and 0.02% triton X-100. Prior to initiation of the polymerase reaction PEG, methanol is added and the buffer is diluted such that the final reaction conditions for buffer 4 consisted of: 40 mM tris pH (8.0), 12 mM $MgCl_2$, 5 mM DTT, 1 mM spermidine, 0.002% triton X-100, 10% methanol, and 4% PEG.

BUFFER 5: Reagents are mixed together to form a 10x stock solution of buffer 5 (400 mM Tris-Cl (pH 8.0), 120 mM $MgCl_2$, 50 mM DTT, 10 mM spermidine and 0.02% triton X-100. Prior to initiation of the polymerase reaction PEG, LiCl is added and the buffer is diluted such that the final reaction conditions for buffer 5 consisted of: 40 mM tris pH (8.0), 12 mM $MgCl_2$, 5 mM DTT, 1 mM spermidine, 0.002% triton X-100, 1 mM LiCl and 4% PEG.

BUFFER 6: Reagents are mixed together to form a 10x stock solution of buffer 6 (400 mM Tris-Cl (pH 8.0), 120 mM $MgCl_2$, 50 mM DTT, 10 mM spermidine and 0.02% triton X-100. Prior to initiation of the polymerase reaction PEG, methanol is added and the buffer is diluted such that the final reaction conditions for buffer 6 consisted of: 40 mM tris pH (8.0), 12 mM $MgCl_2$, 5 mM DTT, 1 mM spermidine, 0.002% triton X-100, 10% methanol, and 4% PEG.

BUFFER 7: Reagents are mixed together to form a 10x stock solution of buffer 6 (400 mM Tris-Cl (pH 8.0), 120 mM $MgCl_2$, 50 mM DTT, 10 mM spermidine and 0.02% triton X-100. Prior to initiation of the polymerase reaction PEG, methanol and LiCl is added and the buffer is diluted such that the final reaction conditions for buffer 6 consisted of: 40 mM tris pH (8.0), 12 mM $MgCl_2$, 5 mM DTT, 1 mM spermidine, 0.002% triton X-100, 10% methanol, 4% PEG, and 1 mM LiCl.

Example 4

Screening of Modified Nucleotide Triphosphates with Mutant T7 RNA Polymerase

Each modified nucleotide triphosphate was individully tested in buffers 1 through 6 at two different temperatures (25 and 37° C.). Buffers 1–6 tested at 25° C. were designated conditions 1–6 and buffers 1–6 test at 37° C. were designated conditions 7–12 (table 3). In each condition, Y639F mutant T7 polymerase (Sousa and Padilla, Supra) (0.3–2 mg/20 ml reaction), NTP's (2 mM each), DNA template (10 pmol), inorganic pyrophosphatase (5U/ml) and $\alpha$-$^{32}$P NTP (0.8 mCi/pmol template) were combined and heated at the designated temperatures for 1–2 hours. The radiolabeled NTP used was different from the modified triphosphate being testing. The samples were resolved by polyacrylamide gel electrophoresis. Using a PhosphorImager (Molecular Dynamics, Sunnyvale, Calif.), the amount of full-length transcript was quantified and compared with an all-RNA control reaction. The data is presented in Table 4; results in each reaction is expressed as a percent compared to the all-ribonucleotide triphosphate (rNTP) control. The control was run with the mutant T7 polymerase using commercially available polymerase buffer (Boehringer Mannheim, Indianapolis, Ind.).

Example 5

Incorporation of Modified NTP's Using Wild-type T7 RNA Polymerase

Bacteriophage T7 RNA polymerase was purchased from Boehringer Mannheim at 0.4 U/μL concentration. Applicant used the commercial buffer supplied with the enzyme and 0.2 μCi alpha-$^{32}$P NTP in a 50 μL reaction with nucleotides triphosphates at 2 mM each. The template was double-stranded PCR fragment, which was used in previous screens. Reactions were carried out at 37° C. for 1 hour. 10 μL of the sample was run on a 7.5% analytical PAGE and bands were quantitated using a PhosphorImager. Results are calculated as a comparison to an "all ribo" control (non-modified nucleotide triphosphates) and the results are in Table 5.

Example 6

Incorporation of Multiple Modified Nucleotide Triphosphates Into Oligonucleotides Combinations of modified nucleotide triphosphates were tested with the transcription protocol described in example 4, to determine the rates of incorporation of two or more of these triphosphates. Incorporation 2'-Deoxy-2'-(L-histidine) amino uridine (2'-his-NH$_2$-UTP) was tested with unmodified cytidine nucleotide triphosphates, rATP and rGTP in reaction condition number 9. The data is presented as a percentage of incorporation of modified NTP's compared to the all rNTP control and is shown in Table 6a.

Two modified cytidines (2'-NH$_2$-CTP or 2'dCTP) were incorporated along with 2'-his-NH$_2$-UTP with identical efficiencies. 2'-his-NH$_2$-UTP and 2'-NH$_2$-CTP were then tested with various unmodified and modified adenosine triphosphates in the same buffer (Table 6b). The best modified adenosine triphosphate for incorporation with both 2'-his-NH$_2$-UTP and 2'-NH$_2$-CTP was 2'-deoxy-2'amino-2,6-diamino adenosine triphosphate: (2'-NH$_2$-DAPTP).

Example 7

Optimization of Reaction Conditions for Incorporation of Modified Nucleotide Triphosphate The combination of 2'-his-NH$_2$-UTP, 2'-NH$_2$-CTP, 2'-NH$_2$-DAP, and rGTP was tested in several reaction conditions (Table 7) using the incorporation protocol described in example 9. The results demonstrate that of the buffer conditions tested, incorporation of these modified nucleotide triphosphates occur in the presence of both methanol and LiCl.

Example 8

Selection of Novel Enzymatic Nucleic Acid Molecule Motifs Using 2'-Deoxy-2'amino Modified GTP and CTP For selection of new enzymatic nucleic acid molecule motifs, pools of enzymatic nucleic acid molecule were designed to have two substrate binding arms (5 and 16 nucleotides long) and a random region in the middle. The substrate has a biotin on the 5' end, 5 nucleotides complementary to the short binding arm of the pool, an unpaired G (the desired cleavage site), and 16 nucleotides complementary to the long binding arm of the pool. The substrate was bound to column resin through an avidin-biotin complex. The general process for selection is shown in FIG. 2. The protocols described below represent one possible method which may be utilized for selection of enzymatic nucleic acid molecules and are given as a non-limiting example of enzymatic nucleic acid molecule selection with combinatorial libraries.

Construction of Libraries: The oligonucleotides listed below were synthesized by Operon Technologies (Alameda, Calif.). Templates were gel purified and then run through a Sep-Pak cartridge (Waters, Millford, Mass.) using the manufacturers protocol. Primers (MST3, MST7c, MST3del) were used without purification.

Primers

MST3 (30 mer): 5'-CAC TTA GCA TTA ACC CTC ACT AAA GGC CGT-3' (SEQ ID NO. 59)

MST7c (33 mer): 5'-TAA TAC GAC TCA CTA TAG GAA AGG TGT GCA ACC-3' (SEQ ID NO. 60)

MST3del (18 mer): 5'-ACC CTC ACT AAA GGC CGT-3' (SEQ ID NO. 61)

Templates

MSN60c (93 mer): 5'-ACC CTC ACT AAA GGC CGT (N)$_{60}$ GGT TGC ACA CCT TTG-3' (SEQ ID NO. 62)

MSN40c (73 mer): 5'-ACC CTC ACT AAA GGC CGT (N)$_{40}$ GGT TGC ACA CCT TTG-3' (SEQ ID NO. 63)

MSN20c (53 mer): 5'-ACC CTC ACT AAA GGC CGT (N)$_{20}$ GGT TGC ACA CCT TTG-3' (SEQ ID NO. 64)

N60 library was constructed using MSN60c as a template and MST3/MST7c as primers. N40 and N20 libraries were constructed using MSN40c (or MSN20c) as template and MST3del/MST7c as primers.

Single stranded templates were converted into double-stranded DNA by the following protocol: 5 nmol template, 10 nmol each primer, in 10 ml reaction volume using standard PCR buffer, dNTP's, and taq DNA polymerase (all reagents from Boehringer Mannheim). Synthesis cycle conditions were 94° C., 4 minutes; (94° C., 1 minute; 42° C., 1 minute; 72° C., 2 minutes)×4; 72° C., 10 minutes. Products were checked on agarose gel to confirm the length of each fragment (N60=123 bp, N40=91 bp, N20=71 bp) and then were phenol/chloroform extracted and ethanol precipitated. Concentration of the double-stranded product was 25 μM.

Transcription of the initial pools was performed in a 1 ml volume comprising: 500 pmol double-stranded template (3×10$^{14}$ molecules), 40 mM tris-HCl (pH 8.0), 12 mM MgCl$_2$, 1 mM spermidine, 5 mM DTT, 0.002% triton X-100, 1 mM LiCl, 4% PEG 8000, 10% methanol, 2 mM ATP (Pharmacia), 2 mM GTP (Pharmacia), 2 mM 2'-deoxy-2'-amino-CTP (USB), 2 mM 2'-deoxy-2'-amino-UTP (USB), 5 U/ml inorganic pyrophosphatase (Sigma), 5 U/μl T7 RNA polymerase (USB; Y639F mutant was used in some cases at 0.1 mg/ml (Sousa and Padilla, Supra)), 37° C., 2 hours. Transcribed libraries were purified by denaturing PAGE (N60=106 ntds, N40=74, N20=54) and the resulting product was desalted using Sep-Pak columns and then ethanol precipitated.

Initial column-Selection: The following biotinylated substrate was synthesized using standard protocols (Usman et al., 1987 *J. Am. Chem. Soc.*, 109, 7845; Scaringe et al., 1990 *Nucleic Acids Res.*, 18, 5433; and Wincott et al., 1995 *Nucleic Acids Res.*, 23, 2677–2684):

5'-biotin-C18 spacer-GCC GUG GGU UGC ACA CCU UUC C-C18 spacer-thiol modifier C6 S-S-inverted abasic-3' (SEQ ID NO. 65)

Substrate was purified by denaturing PAGE and ethanol precipitated. 10 nmol of substrate was linked to a NeutrAvidin column using the following protocol: 400 μl UltraLink Immobilized NeutrAvidin slurry (200 μl beads, Pierce, Rockford, Ill.) were loaded into a polystyrene column (Pierce). The column was washed twice with 1 ml of binding buffer (20 mM NaPO$_4$ (pH 7.5), 150 mM NaCl) and then capped off (i.e., a cap was put on the bottom of the column to stop the flow). 200 μl of the substrate suspended in binding buffer was applied and allowed to incubate at room temperature for 30 minutes with occasional vortexing to ensure even linking and distribution of the solution to the resin. After the incubation, the cap was removed and the column was washed with 1 ml binding buffer followed by 1 ml column buffer (50 mM tris-HCL (pH 8.5), 100 mM NaCl, 50 mM KCl). The column was then ready for use and capped off. 1 nmol of the initial pool RNA was loaded on the column in a volume of 200 μl column buffer. It was allowed to bind the substrate by incubating for 30 minutes at room temperature with occasional vortexing. After the incubation, the cap was removed and the column was washed twice with 1 ml column buffer and capped off. 200 μl of elution buffer (50 mM tris-HCl (pH 8.5), 100 mM NaCl, 50 mM KCl, 25 mM MgCl$_2$) was applied to the column followed by 30 minute incubation at room temperature with occasional vortexing. The cap was removed and four 200 μl fractions were collected using elution buffer.

Second Column (Counter Selection): A diagram for events in the second column is generally shown in FIG. 3 and substrate oligonucleotide used is shown below:

5'-GGU UGC ACA CCU UUC C-C 18 spacer-biotin-inverted abasic-3' (SEQ ID NO. 66)

This column substrate was linked to UltraLink NeutrAvidin resin as previously described (40 pmol) which was washed twice with elution buffer. The eluent from the first column purification was then run on the second column. The use of this column allowed for binding of RNA that non-specifically diluted from the first column, while RNA that performed a catalytic event and had product bound to it, flowed through the second column. The fractions were ethanol precipitated using glycogen as carrier and rehydrated in sterile water for amplification.

Amplification: RNA and primer MST3 (10–100 pmol) were denatured at 90° C. for 3 minutes in water and then snap-cooled on ice for one minute. The following reagents were added to the tube (final concentrations given): 1×PCR buffer (Boerhinger Mannheim), 1 mM dNTP's (for PCR, Boerhinger Mannheim), 2 U/μl RNase-Inhibitor (Boerhinger Mannheim), 10 U/μl Superscript II Reverse Transcriptase (BRL). The reaction was incubated for 1 hour at 42° C., then at 95° C. for 5 minutes in order to destroy the Superscript. The following reagents were then added to the tube to increase the volume five-fold for the PCR step (final concentrations/amounts given): MST7c primer (10–100 pmol, same amount as in RT step), 1×PCR buffer, taq DNA polymerase (0.025–0.05 U/μl, Boerhinger Mannheim). The reaction was cycled as follows: 94° C., 4 minutes; (94° C., 30s; 42–54° C., 30s; 72° C., 1 minute)×4–30 cycles; 72° C., 5 minutes; 30° C., 30 minutes. Cycle number and annealing temperature were decided on a round by round basis. In cases where heteroduplex was observed, the reaction was diluted five-fold with fresh reagents and allowed to progress through 2 more amplification cycles. Resulting products were analyzed for size on an agarose gel (N60=123 bp, N40=103 bp, N20=83 bp) and then ethanol precipitated.

Transcriptions: Transcription of amplified products was done using the conditions described above with the following modifications: 10–20% of the amplification reaction was used as template, reaction volume was 100–500 μl, and the products sizes varied slightly (N60=106 ntds, N40=86, N20=66). A small amount of $^{32}$P-GTP was added to reactions for quantitation purposes.

Subsequent Rounds: Subsequent rounds of selection used 20 pmols of input RNA and 40 pmol of the 22 nucleotide substrate on the column.

Activity of Pools: Pools were assayed for activity under single turnover conditions every three to four rounds. Activity assay conditions were as follows: 50 mM tris-HCl (pH 8.5), 25 mM MgCl$_2$, 100 mM NaCl, 50 mM KCl, trace $^{32}$P labeled substrate, 10 nM RNA pool. 2× pool in buffer and, separately, 2× substrate in buffer were incubated at 90° C. for 3 minutes, then at 37° C. for 3 minutes. Equal volume 2× substrate was then added the 2× pool tube (t=0). Initial assay time points were taken at 4 and 24 hours: 5 μl was removed and quenched in 8 μl cold Stop buffer (96% formamide, 20 mM EDTA, 0.05% bromphenyl blue/xylene cyanol). Samples were heated 90° C., 3 minutes, and loaded on a 20% sequencing gel. Quantitation was performed using a Molecular Dynamics PhosphorImager and ImageQuaNT software. The data is shown in table 8.

Samples from the pools of oligonucleotide were cloned into vectors and sequenced using standard protocols (Sambrook et al., *Molecular Cloning: A Laboratory Manual*, Cold Spring Harbor Laboratory Press). The enzymatic nucleic acid molecules were transcribed from a representative number of these claones using methods described in this application. Individuals from each pool were tested for RNA cleavage from N60 and N40 by incubating the enzymatic nucleic acid molecules from the clones with 5/16 substrate in 2 mM MgCl2, pH 7.5, 10 mM KCl at 37° C. The data in table 10 shows that the enzymatic nucleic acid molecules isolated from the pool are individually active.

Kinetic Activity: Kinetic activity of the enzymatic nucleic acid molecule shown in table 10, was determined by incubating enzymatic nucleic acid molecule (10 nM) with substrate in a cleavage buffer (pH 8.5, 25 mM MgCl$_2$, 100 mM NaCl, 50 mM KCl) at 37° C.

Magnesium Dependence: Magnesium dependence of round 15 of N20 was tested by varying MgCl$_2$ while other conditions were held constant (50 mM tris pH 8.0, 100 mM NaCl, 50 mM KCl, single turnover, 10 nM pool). The data is shown in table 11, which demonstrates increased activity with increased magnesium concentrations.

Example 9

Selection of Novel Enzymatic Nucleic Acid Molecule Motifs Using 2'-Deoxy-2'-(N-histidyl) amino UTP, 2'-Fluoro-ATP, and 2'-Deoxy-2'-amino CTP and GTP The method described in example 8 was repeated using 2'-Deoxy-2'-(N-histidyl)amino UTP, 2'-Fluoro-ATP, and 2'-deoxy-2'-amino CTP and GTP. However, rather than causing cleavage on the initial column with MgCl$_2$, the initial random modified-RNA pool was loaded onto substrate-resin in the following buffer; 5 mM NaoAc pH 5.2, 1 M NaCl at 4° C. After ample washing the resin was moved to 22° C. and the buffer switch 20 mM HEPES pH 7.4, 140 mM KCl, 10 mM NaCl, 1 mM CaCl$_2$, 1 mM MgCl$_2$. In one selection of N60 oligonucleotides, no divalent cations (MgCl$_2$, CaCl$_2$) was used. The resin was incubated for 10 minutes to allow reaction and the eluant collected.

The enzymatic nucleic acid molecule pools were capable of cleaving 1–3% of the present substrate even in the absense of divalent cations, the background (in the absence of modified pools) was 0.2–0.4%.

Example 10

Synthesis of 5-Imidazoleacetic Acid 2'-Deoxy-5'-triphosphate Uridine 5-dinitrophenylimidazoleacetic acid 2'-dexoy uridine nucleoside (80 mg) was dissolved in 5 ml of triethylphosphate while stirring under argon, and the reaction mixture was cooled to 0° C. Phosphorous oxychloride (1.8 eq, 22 ml) was added to the reaction mixture at 0° C., three more aliquots were added over the course of 48 hours at room temperature. The reaction mixture was then diluted with anhydrous MeCN (5 ml) and cooled to 0° C., followed by the addition of tributylamine (0.65 ml) and tributylammonium pyrophosphate (4.0 eq, 0.24 g). After 45 minutes, the reaction was quenched with 10 ml aq. methyl amine for four hours. After co-evaporation with MeOH (3×), purified material on DEAE Sephadex, followed by RP chromatography to afford 15 mg of triphosphate.

Example 11

Synthesis of 2'-(N-Lysyl)amino-2'-deoxy-cytidine Triphosphate

2'-(N-lysyl)amino 2'-deoxy cytidine (0.180 g, 0.22 mmol) was dissolved in triethyl phosphate (2.00 ml) under Ar. The solution was cooled to 0° C. in an ice bath. Phosphorus oxychloride (99.999%, 3 eq., 0.0672 mL) was added to the solution and the reaction was stirred for two hours at 0° C. Tributylammonium pyrophosphate (4 eq., 0.400 g) was dissolved in 3.42 mL of acetonitrile and tribuytylamine (0.165 mL). Acetonitrile (1 mL) was added to the monophosphate solution followed by the pyrophosphate solution which was added dropwise. The solution was clear. The reaction was allowed to warm up to room temperature. After stirring for 45 minutes, methyl amine (5 mL) was added and the reaction and stirred at room temperature for 2 hours. A two phase mixture appeared (little beads at the bottom of the flask). TLC (7:1:2 iPrOH:NH$_4$OH:H$_2$O) showed the appearance of a triphosphate material. The solution was concentrated, dissolved in water and loaded on a newly prepared DEAE Sephadex A-25 column. The column was washed with a gradiant up to 0.6 M TEAB buffer and the product eluted off in fractions 90–95. The fractions were analyzed by ion exchange HPLC. Each fraction showed one triphosphate peak that eluted at ~4.000 minutes. The fractions were combined and pumped down from methanol to remove buffer salt to yield 15.7 mgs of product.

Example 12

Synthesis of 2'-Deoxy-2'-(L-histidine)amino Cytidine Triphosphate

2'-[N-Fmoc, N$^{imid}$-dinitrophenyl-histidyl]amino-2'-cytidine (0.310 g, 4.04 mmol) was dissolved in triethyl phosphate (3 ml) under Ar. The solution was cooled to 0° C. Phosphorus oxychloride (1.8 eq., 0.068 mL) was added to the solution and stored overnight in the freezer. The next morning TLC (10% MeOH in CH$_2$Cl$_2$) showed a lot of starting material, so one more equivalent of POCl$_3$ was added. After two hours the TLC still showed starting material. Tributylamine (0.303 mL) and Tributylammonium pyrophosphate (4 eq., 0.734 g) dissolved in 6.3 mL of acetonitrile (added dropwise) were added to the monophosphate solution. The reaction was allowed to warm up to room temperature. After stirring for 15 min methyl amine (10 mL) was added at room temperature and stirring continued for 2 hours. TLC (7:1:2 iPrOH:NH$_4$OH:H$_2$O) showed the appearance of a triphosphate material. The solution was concentrated, dissolved in water and loaded on a DEAE Sephadex A-25 column. The column was washed with a gradiant up to 0.6 M TEAB buffer and the product eluted off in fractions 170–179. The fractions were analyzed by ion exchange HPLC. Each fraction showed one triphosphate peak that eluted at ~6.77 minutes. The fractions were combined and pumped down from methanol to remove buffer salt to aford 17 mgs of product.

Example 13

Screening for Novel Enzymatic Nucleic Acid Molecule Motifs Using Modified NTPs (Class I Motif)

Our initial pool contained 3×10$^{14}$ individual sequences of 2'-amino-dCTP/2'-amino-dUTP RNA. We optimized transcription conditions in order to increase the amount of RNA product by inclusion of methanol and lithium chloride. 2'-amino deoxynucleotides do not interfere with the reverse transcription and amplification steps of selection and confer nuclease resistance. We designed the pool to have two binding arms complementary to the substrate, separated by the random 40 nucleotide region. The 16-mer substrate had two domains, 5 and 10 nucleotides long, that bind the pool, separated by an unpaired guanosine. On the 5' end of the substrate was a biotin attached by a C18 linker. This enabled us to link the substrate to a NeutrAvidin resin in a column format. The desired reaction would be cleavage at the unpaired G upon addition of magnesium cofactor followed by dissociation from the column due to instability of the 5 base pair helix. A detailed protocol follows:

Enzymatic nucleic acid molecule Pool Prep: The initial pool DNA was prepared by converting the following template oligonucleotides into double-stranded DNA by filling in with taq polymerase. (template=5'-ACC CTC ACT AAA GGC CGT (N)$_{40}$ GGT TGC ACA CCT TTC-3' (SEQ ID NO. 63); primer 1=5'-CAC TTA GCA TTA ACC CTC ACT AAA GGC CGT-3' (SEQ ID NO. 59); primer 2=5'-TAA TAC GAC TCA CTA TAG GAA AGG TGT GCA ACC-3' (SEQ ID NO. 60)). All DNA oligonucleotides were synthesized by Operon technologies. Template oligos were purified by denaturing PAGE and Sep-pak chromatography columns (Waters). RNA substrate oligos were using standard solid phase chemistry and purified by denaturing PAGE followed by ethanol precipitation. Substrates for in vitro cleavage assays were 5'-end labeled with gamma-$^{32}$P-ATP and T4 polynucleotide kinase followed by denaturing PAGE purification and ethanol precipitation.

5 nmole of template, 10 nmole of each primer and 250 U taq polymerase were incubated in a 10 ml volume with 1×PCR buffer (10 mM tris-HCl (pH 8.3), 1.5 mM MgCl$_2$, 50 mM KCl) and 0.2 mM each dNTP as follows: 94° C., 4 minutes; (94° C., 1 min; 42° C., 1 min; 72° C., 2 min) through four cycles; and then 72° C., for 10 minutes. The product was analyzed on 2% Separide agarose gel for size and then was extracted twice with buffered phenol, then chloroform-isoamyl alcohol, and ethanol precipitated. The initial RNA pool was made by transcription of 500 pmole ($3\times10^{14}$ molecules) of this DNA as follows. Template DNA was added to 40 mM tris-HCl (pH 8.0), 12 mM $MgCl_2$, 5 mM dithiothreitol (DTT), 1 mM spermidine, 0.002% triton X-100, 1 mM LiCl, 4% PEG-8000, 10% methanol, 2 mM ATP, 2 mM GTP, 2 mM 2'-amino-dCTP, 2 mM 2'-amino-dUTP, 5 U/ml inorganic pyrophosphatase, and 5 U/µl T7 RNA polymerase at room temperature for a total volume of 1 ml. A separate reaction contained a trace amount of alpha-$^{32}$P-GTP for detection. Transcriptions were incubated at 37° C. for 2 hours followed by addition of equal volume STOP buffer (94% formamide, 20 mM EDTA, 0.05% bromophenol blue). The resulting RNA was purified by 6% denaturing PAGE gel, Sep-pak chromatography, and ethanol precipitated.

INITIAL SELECTION: 2 nmole of 16 mer 5'-biotinylated substrate (Biotin-C18 linker-5'-GCC GUG GGU UGC ACA C-3' (SEQ ID NO: 69) was linked to 200 µl UltraLink Immobilized NeutrAvidin™ resin (400 µl slurry, Pierce) in binding buffer (20 mM $NaPO_4$ (pH 7.5), 150 mM NaCl) for 30 minutes at room temperature. The resulting substrate column was washed with 2 ml binding buffer followed by 2 ml column buffer (50 mM tris-HCl (pH 8.5), 100 mM NaCl, 50 mM KCl). The flow was capped off and 1000 pmole of initial pool RNA in 200 µl column buffer was added to the column and incubated 30 minutes at room temperature. The column was uncapped and washed with 2 ml column buffer, then capped off. 200 µl elution buffer (=column buffer+25 mM $MgCl_2$) was added to the column and allowed to incubate 30 minutes at room temperature. The column was uncapped and eluent collected followed by three 200 µl elution buffer washes. The eluent/washes were ethanol precipitated using glycogen as carrier and rehydrated in 50 µl sterile $H_2O$. The eluted RNA was amplified by standard reverse transcription/PCR amplification techniques. 5–31 µl RNA was incubated with 20 pmol of primer 1 in 14 µl volume 90° for 3 min then placed on ice for 1 minute. The following reagent were added (final concentrations noted): 1×PCR buffer, 1 mM each dNTP, 2 U/µl RNase Inhibitor, 10 U/µl SuperScript™ II reverse transcriptase. The reaction was incubated 42° for 1 hour followed by 95° for 5 min in order to inactivate the reverse transcriptase. The volume was then increased to 100 µl by adding water and reagents for PCR: 1×PCR buffer, 20 pmol primer 2, and 2.5 U taq DNA polymerase. The reaction was cycled in a Hybaid thermocycler: 94°, 4 min; (94° C., 30 sec; 54° C., 30 sec; 72° C., 1 min) ×25; 72° C., 5 min. Products were analyzed on agarose gel for size and ethanol precipitated. One-third to one-fifth of the PCR DNA was used to transcribe the next generation, in 100 µl volume, as described above. Subsequent rounds used 20 pmol RNA for the column with 40 pmol substrate.

TWO COLUMN SELECTION: At generation 8 (G8), the column selection was changed to the two column format. 200 pmoles of 22 mer 5'-biotinylated substrate (Biotin-C18 linker-5'-GCC GUG GGU UGC ACA CCU UUC C-3' (SEQ ID NO: 65)-C18 linker-thiol modifier C6 S-S-inverted abasic') was used in the selection column as described above. Elution was in 200 µl elution buffer followed by a 1 ml elution buffer wash. The 1200 µl eluent was passed through a product trap column by gravity. The product trap column was prepared as follows: 200 pmol 16 mer 5'-biotinylated "product" (5'-GGU UGC ACA CCU UUC C-3' (SEQ ID NO: 66)-C18 linker-biotin') was linked to the column as described above and the column was equilibrated in elution buffer. Eluent from the product column was precipitated as previously described. The products were amplified as above only with 2.5-fold more volume and 100 pmol each primer. 100 µl of the PCR reaction was used to do a cycle course; the remaining fraction was amplified the minimal number of cycles needed for product. After 3 rounds (G11), there was visible activity in a single turnover cleavage assay. By generation 13, 45% of the substrate was cleaved at 4 hours; $k_{obs}$ of the pool was 0.037 min$^{-1}$ in 25 mM $MgCl_2$. We subcloned and sequenced generation 13; the pool was still very diverse. Since our goal was a enzymatic nucleic acid molecule that would work in a physiological environment, we decided to change selection pressure rather than exhaustively catalog G13.

Reselection of the N40 pool was started from G12 DNA. Part of the G12 DNA was subjected to hypermutagenic PCR (Vartanian et al., 1996, *Nucleic Acids Research* 24, 2627–2631) to introduce a 10% per position mutation frequency and was designated N40H. At round 19, part of the DNA was hypermutagenized again, giving N40M and N40HM (a total of 4 parallel pools). The column substrates remained the same; buffers were changed and temperature of binding and elution was raised to 37° C. Column buffer was replaced by physiological buffer (50 mM tris-HCl (pH 7.5), 140 mM KCl, 10 mM NaCl) and elution buffer was replaced by 1 mM Mg buffer (physiological buffer+1 mM $MgCl_2$). Amount of time allowed for the pool to bind the column was eventually reduced to 10 min and elution time was gradually reduced from 30 min to 20 sec. Between rounds 18 and 23, $k_{obs}$, for the N40 pool stayed relatively constant at 0.035–0.04 min$^{-1}$. Generation 22 from each of the 4 pools was cloned and sequenced.

CLONING AND SEQUENCING: Generations 13 and 22 were cloned using Novagen's Perfectly Blunt Cloning kit (pT7Blue-3 vector) following the kit protocol. Clones were screened for insert by PCR amplification using vector-specific primers. Positive clones were sequenced using ABI Prism 7700 sequence detection system and vector-specific primer. Sequences were aligned using MacVector software; two-dimensional folding was done using Mulfold software (Zuker, 1989, *Science* 244, 48–52; Jaeger et al., 1989, *Biochemistry* 86, 7706–7710; Jaeger et al., 1989, R. F. Doolittle ed., *Methods in Enzymology*, 183, 281–306). Individual clone transcription units were constructed by PCR amplification with 50 pmol each primer 1 and primer 2 in 1×PCR buffer, 0.2 mM each dNTP, and 2.5 U of taq polymerase in 100 µl volume cycled as follows: 94° C., 4 min; (94° C., 30 sec; 54° C., 30 sec; 72° C., 1 min) ×20; 72° C., 5 min. Transcription units were ethanol precipitated, rehydrated in 30 µl H2O, and 10 µl was transcribed in 100 µl volume and purified as previously described.

Thirty-six clones from each pool were sequenced and were found to be variations of the same consensus motif. Unique clones were assayed for activity in 1 mM $MgCl_2$ and physiological conditions; nine clones represented the consensus sequence and was used in subsequent experiments. There were no mutations that significantly increased activity; most of the mutations were in regions believed to be duplex, based on the proposed secondary structure. In order to make the motif shorter, we deleted the 3'-terminal 25 nucleotides necessary to bind the primer for amplification. The measured rates of the full length and truncated molecules were both 0.04 min$^{-1}$; thus we were able reduce the size of the motif from 86 to 61 nucleotides. The molecule was shortened even further by truncating base pairs in the stem loop structures as well as the substrate recognition arms to yield a 48 nucleotide molecule. In addition many of the ribonucleotides were replaced with 2-O-methyl modified nucleotides to stabilize the molecule. An example of the new motif is given in FIG. 4. Those of ordinary skill in the art will recognize that the molecule is not limited to the chemical modifications shown in the figure and that it represents only one possible chemically modified molecule.

Kinetic Analysis

Single turnover kinetics were performed with trace amounts of 5'-$^{32}$P-labeled substrate and 10–1000 nM pool of enzymatic nucleic acid molecule. 2× substrate in 1× buffer and 2× pool/enzymatic nucleic acid molecule in 1× buffer were incubated separately 90° for 3 min followed by equilibration to 37° for 3 min. Equal volume of 2× substrate was added to pool/enzymatic nucleic acid molecule at to and the reaction was incubated at 37° C. Time points were quenched in 1.2 vol STOP buffer on ice. Samples were heated to 90° C. for 3 min prior to separation on 15% sequencing gels. Gels were imaged using a PhosphorImager and quantitated using ImageQuant software (Molecular Dynamics). Curves were fit to double-exponential decay in most cases, although some of the curves required linear fits.

STABILITY: Serum stability assays were performed as previously described (Beigelman et al., 1995, J. Biol. Chem. 270, 25702–25708). 1 μg of 5'-32P-labeled synthetic enzymatic nucleic acid molecule was added to 13 μl cold and assayed for decay in human serum. Gels and quantitation were as described in kinetics section.

Example 14

Inhibition of Hepatitis C Virus (HCV) Using New Motif

During HCV infection, viral RNA is present as a potential target for enzymatic nucleic acid molecule cleavage at several processes: uncoating, translation, RNA replication and packaging. Target RNA may be more or less accessible to enzymatic nucleic acid molecule cleavage at any one of these steps. Although the association between the HCV initial ribosome entry site (IRES) and the translation apparatus is mimicked in the HCV 5'UTR/luciferase reporter system (example 9), these other viral processes are not represented in the OST7 system. The resulting RNA/protein complexes associated with the target viral RNA are also absent. Moreover, these processes may be coupled in an HCV-infected cell which could further impact target RNA accessibility. Therefore, we tested whether enzymatic nucleic acid molecules designed to cleave the HCV 5'UTR could effect a replicating viral system.

Recently, Lu and Wimmer characterized an HCV-poliovirus chimera in which the poliovirus IRES was replaced by the IRES from HCV (Lu & Wimmer, 1996, Proc. Natl. Acad. Sci. USA. 93, 1412–1417). Poliovirus (PV) is a positive strand RNA virus like HCV, but unlike HCV is non-enveloped and replicates efficiently in cell culture. The HCV-PV chimera expresses a stable, small plaque phenotype relative to wild type PV.

The capability of the new enzymatic nucleic acid molecule motif to inhibit HCV RNA intracellularly was tested using a dual reporter system that utilizes both firefly and Renilla luciferase (FIG. 5). A number of enzymatic nucleic acid molecules having the new class I motif were designed and tested (Table XII). The new enzymatic nucleic acid molecule motif targeted to the 5' HCV UTR region, which when cleaved, would prevent the translation of the transcript into luciferase. OST-7 cells were plated at 12,500 cells per well in black walled 96 well plates (Packard) in medium DMEM containing 10% fetal bovine serum, 1% pen/strep, and 1% L-glutamine and incubated at 37° C. overnight. A plasmid containing T7 promoter expressing 5' HCV UTR and firefly luciferase (T7C1-341 (Wang et al., 1993, J. of Virol. 67, 3338–3344)) was mixed with a pRLSV40 Renilla control plasmid (Promega Corporation) followed by enzymatic nucleic acid molecule, and cationic lipid to make a 5× concentration of the reagents (T7C1-341 (4 μg/ml), pRLSV40 renilla luciferase control (6 μg/ml), enzymatic nucleic acid molecule (250 nM), transfection reagent (28.5 μg/ml).

The complex mixture was incubated at 37° C. for 20 minutes. The media was removed from the cells and 120 μl of Opti-mem media was added to the well followed by 30 μl of the 5× complex mixture. 150 μl of Opti-mem was added to the wells holding the untreated cells. The complex mixture was incubated on OST-7 cells for 4 hours, lysed with passive lysis buffer (Promega Corporation) and luminescent signals were quantified using the Dual Luciferase Assay Kit using the manufacturer's protocol (Promega Corporation). The data shown in FIG. 6 is a dose curve of enzymatic nucleic acid molecule targeting site 146 of the HCV RNA and is presented as a ratio between the firefly and Renilla luciferase fluorescence. The enzymatic nucleic acid molecule was able to reduce the quantity of HCV RNA at all enzymatic nucleic acid molecule concentrations yielding an IC 50 of approximately 5 nM. Other sites were also efficacious (FIG. 7), in particular enzymatic nucleic acid molecules targeting 133, 209, and 273 were also able to reduce HCV RNA compared to the irrelevant (IRR) controls.

Example 15

Cleavage of Substrates Using Completely Modified Oligonucleotides

The ability of an enzymatic nucleic acid which is modified at every 2' position to cleave a target RNA was tested to determine if any ribonucleotide positions are necessary. A ribozyme was constructed with 2'-O-methyl, and 2'-amino (NH$_2$) modified nucleotides (table 12; gene name: no ribo) and kinetic analysis was performed as described in example 13. 100 nM enzymatic nucleic acid was mixed with trace amounts of substrate in the presence of 1 mM MgCl$_2$ at physiological conditions (37° C.). The no ribo nucleotide have a K$_{rel}$ of 0.13 compared to the enzymatic nucleic acid shown in table 12 (ribo) which contained ribonucleotides.

Example 16

Screening for Novel Enzymatic Nucleic Acid Molecule Motifs (Class II Motifs)

The selections were initiated with pools of >10$^{14}$ modified RNA's of the following sequence: 5'-GGGAGGAGGAAGUGCCU-3'-(N)$_{35}$-5'-UGCCGCGCUCGCUCCCAGUCC-3' (SEQ ID NO: 67). The RNA was enzymatically generated using the mutant T7 Y639F RNA polymerase prepared by Rui Souza. The following modified NTP's were incorporated: 2'-deoxy-2'-fluoro-adenine triphosphate, 2'-deoxy-2'-fluoro-uridine triphosphate or 2'-deoxy-2'-fluoro-5-[(N-imidazole-4acetyl) propyl amine] uridine triphosphate, and 2'-deoxy-2'-amino-cytidine triphosphate; natural guanidine triphosphate was used in all selections so that alpha-$^{32}$P-GTP could be used to label pool RNA's. RNA pools were purified by denaturing gel electrophoresis 8% polyacrylamide 7 M Urea.

RNA pools were added to 100 ul of 5 uM Resin A in the buffer A (20 mM HEPES pH 7.4, 140 mM KCL, 10 mM NaCl) and incubated at 22° C. for 5 minutes. The temperature was then raised to 37° C. for 10 minutes. The resin was washed with 5 ml buffer A. Reaction was triggered by the addition of buffer B(20 mM HEPES pH 7.4, 140 mM KCL, 10 mM NaCl, 1 mM MgCl$_2$, 1 mM CaCl$_2$). Incubation proceeded for 20 minutes in the first generation and was reduced progressively to 1 minute in the final generations; with 13 total generations. The reaction eluant was collected in 5 M NaCl to give a final concentration of 2 M NaCl. To this was added 100 μl of 50% slurry Ultralink NeutraAvidin (Pierce), Binding of cleaved biotin product to the avidin resin was allowed by 20 minute incubation at 22° C. The resin was subsequently washed with 5 ml of 20 mM HEPES pH 7.4, 2 M NaCl. Desired RNA's were removed by a 1.2 ml denaturing wash 1M NaCl, 10 M Urea at 94° C. over 10 minutes. RNA's were double precipitated in 0.3 M sodium acetate to remove Cl$^-$ ions inhibitory to reverse transcription. Standard protocols of reverse transcription and PCR amplification were performed. RNA's were again transcribed with the modified NTP's described above. After 13 generations cloning and sequencing provided 14 sequences which were able to cleave the target substrate. Six sequences were characterized to determine secondary structure and kinetic cleavage rates. The structures and kinetic data is given in FIG. 8. The sequences of eight other enzymatic nucleic acid molecule sequences are given in table XIII. Size, sequence, and chemical compositions of these molecules can be modified as described under example 13 and as well known in the art.

Nucleic Acid Catalyst Engineering

Sequence, chemical and structural variants of Class I and Class II enzymatic nucleic acid molecule can be engineered and re-engineered using the techniques shown in this application and known in the art. For example, the size of class I and class II enzymatic nucleic acid molecules can, be reduced or increased using the techniques known in the art (Zaug et al., 1986, *Nature*, 324, 429; Ruffner et al., 1990, *Biochem.*, 29, 10695; Beaudry et al., 1990, *Biochem.*, 29, 6534; McCall et al., 1992, *Proc. Natl. Acad Sci., USA.*, 89, 5710; Long et al., 1994, Supra; Hendry et al., 1994, *BBA* 1219, 405; Benseler et al., 1993, *JACS*, 115, 8483; Thompson et al., 1996, *Nucl. Acids Res.*, 24, 4401; Michels et al., 1995, *Biochem.*, 34, 2965; Been et al., 1992, *Biochem.*, 31, 11843; Guo et al., 1995, *EMBO. J.*, 14, 368; Pan et al., 1994, *Biochem.*, 33, 9561; Cech, 1992, *Curr. Op. Struc. Bio.*, 2, 605; Sugiyama et al., 1996, *FEBS Lett.*, 392, 215; Beigelman et al., 1994, *Bioorg. Med. Chem.*, 4, 1715; Santoro et al., 1997, *PNAS* 94, 4262; all are incorporated in its totality by reference herein), to the extent that the overall catalytic activity of the ribozyme is not significantly decreased.

Further rounds of in vitro selection strategies described herein and variations thereof can be readily used by a person skilled in the art to evolve additional nucleic acid catalysts and such new catalysts are within the scope of the instant invention.

Applications

The use of NTP's described in this invention have several research and commercial applications. These modified nucleotide triphosphates can be used for in vitro selection (evolution) of oligonucleotides with novel functions. Examples of in vitro selection protocols are incorporated herein by reference (Joyce, 1989, *Gene*, 82, 83–87; Beaudry et al., 1992, *Science* 257, 635–641; Joyce, 1992, *Scientific American* 267, 90–97; Breaker et al., 1994, *TIBTECH* 12, 268; Bartel et al., 1993, *Science* 261:1411–1418; Szostak 1993, *TIBS* 17, 89–93; Kumar et al., 1995, *FASEB J.*, 9, 1183; Breaker, 1996, *Curr. Op. Biotech.*, 7, 442).

Additionally, these modified nucleotide triphosphates can be employed to generate modified oligonucleotide combinatorial chemistry libraries. Several references for this technology exist (Brenner et al., 1992, *PNAS* 89, 5381–5383, Eaton, 1997, *Curr. Opin. Chem. Biol.* 1, 10–16).

Diagnostic Uses

Enzymatic nucleic acid molecules of this invention may be used as diagnostic tools to examine genetic drift and mutations within diseased cells or to detect the presence of specific RNA in a cell. The close relationship between enzymatic nucleic acid molecule activity and the structure of the target RNA allows the detection of mutations in any region of the molecule which alters the base-pairing and three-dimensional structure of the target RNA. By using multiple enzymatic nucleic acid molecules described in this invention, one may map nucleotide changes which are important to RNA structure and function in vitro, as well as in cells and tissues. Cleavage of target RNAs with enzymatic nucleic acid molecules may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple enzymatic nucleic acid molecules targeted to different genes, enzymatic nucleic acid molecules coupled with known small molecule inhibitors, radiation or intermittent treatment with combinations of enzymatic nucleic acid molecules and/or other chemical or biological molecules). Other in vitro uses of enzymatic nucleic acid molecules of this invention are well known in the art, and include detection of the presence of mRNAs associated with related conditions. Such RNA is detected by determining the presence of a cleavage product after treatment with a enzymatic nucleic acid molecule using standard methodology.

In a specific example, enzymatic nucleic acid molecules which can cleave only wild-type or mutant forms of the target RNA are used for the assay. The first enzymatic nucleic acid molecule is used to identify wild-type RNA present in the sample and the second enzymatic nucleic acid molecule will be used to identify mutant RNA in the sample. As reaction controls, synthetic substrates of both wild-type and mutant RNA will be cleaved by both enzymatic nucleic acid molecules to demonstrate the relative enzymatic nucleic acid molecule efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two enzymatic nucleic acid molecules, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Additional Uses

Potential usefulness of sequence-specific enzymatic nucleic acid molecules of the instant invention might have many of the same applications for the study of RNA that DNA restriction endonucleases have for the study of DNA (Nathans et al., 1975 *Ann. Rev. Biochem.* 44:273). For example, the pattern of restriction fragments could be used to establish sequence relationships between two related RNAs, and large RNAs could be specifically cleaved to fragments of a size more useful for study. The ability to engineer sequence specificity of the enzymatic nucleic acid molecule is ideal for cleavage of RNAs of unknown sequence. Applicant describes the use of nucleic acid molecules to down-regulate gene expression of target genes in bacterial, microbial, fungal, viral, and eukaryotic systems including plant, or mammalian cells.

All patents and publications mentioned in the specification are indicative of the levels of skill of those skilled in the art to which the invention pertains.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

TABLE 1

NUCLEOSIDES USED FOR CHEMICAL SYNTHESIS OF MODIFIED NUCLEOTIDE TRIPHOSPHATES

| | NUCLEOSIDES | Abbreviation | CHEMICAL STRUCTURE |
|---|---|---|---|
| 1 | 2'-O-methyl-2,6-diaminopurine riboside | 2'-O—Me-DAP | 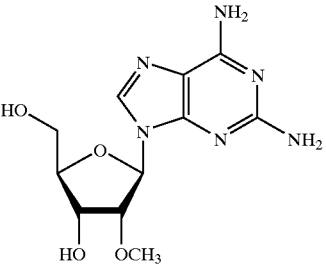 |
| 2 | 2'-deoxy-2'amino-2,6-diaminopurine riboside | 2'-NH$_2$-DAP | 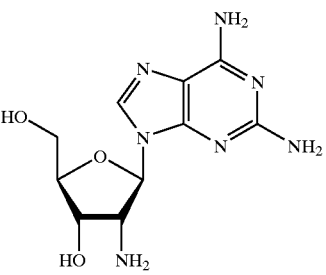 |

TABLE 1-continued

NUCLEOSIDES USED FOR CHEMICAL SYNTHESIS OF MODIFIED NUCLEOTIDE TRIPHOSPHATES

| NUCLEOSIDES | Abbreviation | CHEMICAL STRUCTURE |
|---|---|---|
| 3 2'-(N-alanyl)amino-2'-deoxy-uridine | ala-2'-NH$_2$ U | 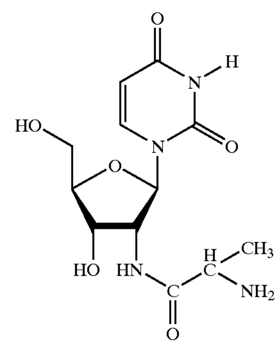 |
| 4 2'-(N-phenylalanyl)amino-2'-deoxy-uridine | phe-2'-NH$_2$—U | 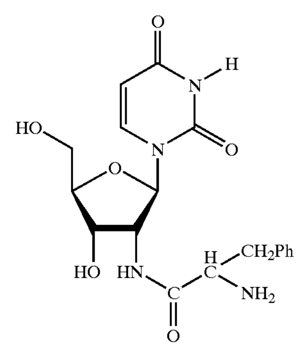 |
| 5 2'-(N-β-alanyl)amino-2'-deoxy uridine | 2'-β-Ala-NH$_2$—U | 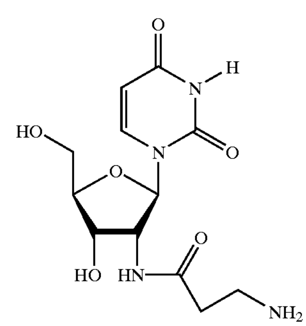 |
| 6 2'-Deoxy-2'-(lysiyl)amino uridine | 2'-L-lys-NH$_2$—U | 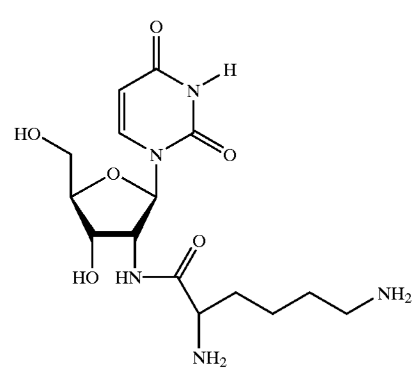 |

TABLE 1-continued

NUCLEOSIDES USED FOR CHEMICAL SYNTHESIS OF MODIFIED NUCLEOTIDE TRIPHOSPHATES

| | NUCLEOSIDES | Abbreviation | CHEMICAL STRUCTURE |
|---|---|---|---|
| 7 | 2'-C-allyl uridine | 2'-C-allyl-U | |
| 8 | 2'-O-amino-uridine | 2'-O—$NH_2$—U | |
| 9 | 2'-O-methylthiomethyl adenosine | 2'-O-MTM-A | |
| 10 | 2'-O-methylthiomethyl cytidine | 2'-O-MTM-C | |

TABLE 1-continued

NUCLEOSIDES USED FOR CHEMICAL SYNTHESIS OF MODIFIED NUCLEOTIDE TRIPHOSPHATES

| | NUCLEOSIDES | Abbreviation | CHEMICAL STRUCTURE |
|---|---|---|---|
| 11 | 2'-O-methylthiomethyl guanosine | 2'-O-MTM-G | |
| 12 | 2'-O-methylthiomethyl-uridine | 2'-O-MTM-U | |
| 13 | 2'-(N-histidyl)amino uridine | 2'-his-$NH_2$—U | |
| 14 | 2'-Deoxy-2'-amino-5-methyl cytidine | 5-Me-2'-$NH_2$—C | |

TABLE 1-continued

NUCLEOSIDES USED FOR CHEMICAL SYNTHESIS OF MODIFIED NUCLEOTIDE TRIPHOSPHATES

| NUCLEOSIDES | Abbreviation | CHEMICAL STRUCTURE |
| --- | --- | --- |
| 15 2'-(N-β-carboxamidine-β-alanyl)amino-2'-dexoy-uridine | β-ala-CA-NH2—U | 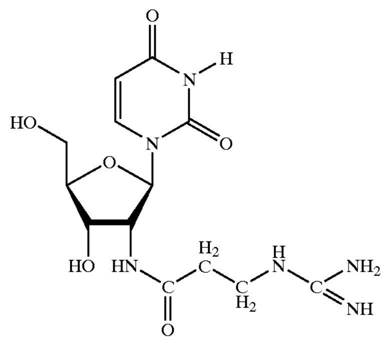 |
| 16 2'-(N-β-alanyl)guanosine | β-Ala-NH$_2$-G | 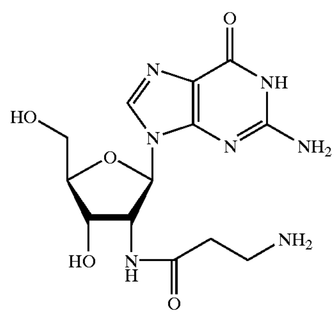 |
| 17 2'-O-Amino-Adenosine | 2'-O—NH$_2$-A | 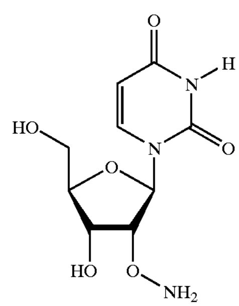 |
| 18 2'-(N-lysyl)amino-2'-deoxy-cytidine | 2'-NH$_2$-lys-C | 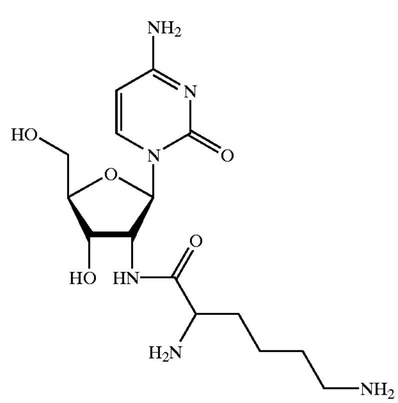 |

TABLE 1-continued

NUCLEOSIDES USED FOR CHEMICAL SYNTHESIS OF MODIFIED NUCLEOTIDE TRIPHOSPHATES

| NUCLEOSIDES | Abbreviation | CHEMICAL STRUCTURE |
| --- | --- | --- |
| 19 2'-Deoxy-2'-(L-histidine)amino Cytidine | 2'-$NH_2$-his-C | (structure) |
| 20 5-Imidazoleacetic acid 2'-deoxy-5'-triphosphate uridine | 5-IAA-U | (structure) |

TABLE 2

PHOSPHORYLATION OF URIDINE IN THE PRESENCE OF DMAP

| 0 equiv. DMAP | | 0.2 equiv. DMAP | | 0.5 equiv. DMAP | | 1.0 equiv. DMAP | |
| --- | --- | --- | --- | --- | --- | --- | --- |
| Time (min) | Product % | Time (min) | Product % | Time (min) | Product % | Time (min) | Product % |
| 0 | 1 | 0 | 0 | 0 | 0 | 0 | 0 |
| 40 | 7 | 10 | 8 | 20 | 27 | 30 | 74 |
| 80 | 10 | 50 | 24 | 60 | 46 | 70 | 77 |
| 120 | 12 | 90 | 33 | 100 | 57 | 110 | 84 |
| 160 | 14 | 130 | 39 | 140 | 63 | 150 | 83 |
| 200 | 17 | 170 | 43 | 180 | 63 | 190 | 84 |
| 240 | 19 | 210 | 47 | 220 | 64 | 230 | 77 |
| 320 | 20 | 250 | 48 | 260 | 68 | 270 | 79 |
| 1130 | 48 | 290 | 49 | 300 | 64 | 310 | 77 |
| 1200 | 46 | 1140 | 68 | 1150 | 76 | 1160 | 72 |
| | | 1210 | 69 | 1220 | 76 | 1230 | 74 |

TABLE 3

Detailed Description of the NTP Incorporation Reaction Conditions

| Condition No. | TRIS-HCL (mM) | $MgCl_2$ (mM) | DTT (mM) | Spermidine (mM) | Triton X-100 (%) | METHANOL (%) | LiCl (mM) | PEG (%) | Temp (° C.) |
| --- | --- | --- | --- | --- | --- | --- | --- | --- | --- |
| 1 | 40 (pH 8.0) | 20 | 10 | 5 | 0.01 | 10 | 1 | — | 25 |
| 2 | 40 (pH 8.0) | 20 | 10 | 5 | 0.01 | 10 | 1 | 4 | 25 |
| 3 | 40 (pH 8.1) | 12 | 5 | 1 | 0.002 | — | — | 4 | 25 |
| 4 | 40 (pH 8.1) | 12 | 5 | 1 | 0.002 | 10 | — | 4 | 25 |
| 5 | 40 (pH 8.1) | 12 | 5 | 1 | 0.002 | — | 1 | 4 | 25 |
| 6 | 40 (pH 8.1) | 12 | 5 | 1 | 0.002 | 10 | 1 | 4 | 25 |
| 7 | 40 (pH 8.0) | 20 | 10 | 5 | 0.01 | 10 | 1 | — | 37 |

TABLE 3-continued

Detailed Description of the NTP Incorporation Reaction Conditions

| Condition No. | TRIS-HCL (mM) | MgCl$_2$ (mM) | DTT (mM) | Spermidine (mM) | Triton X-100 (%) | METHANOL (%) | LiCl (mM) | PEG (%) | Temp (° C.) |
|---|---|---|---|---|---|---|---|---|---|
| 8 | 40 (pH 8.0) | 20 | 10 | 5 | 0.01 | 10 | 1 | 4 | 37 |
| 9 | 40 (pH 8.1) | 12 | 5 | 1 | 0.002 | — | — | 4 | 37 |
| 10 | 40 (pH 8.1) | 12 | 5 | 1 | 0.002 | 10 | — | 4 | 37 |
| 11 | 40 (pH 8.1) | 12 | 5 | 1 | 0.002 | — | 1 | 4 | 37 |
| 12 | 40 (pH 8.1) | 12 | 5 | 1 | 0.002 | 10 | 1 | 4 | 37 |

TABLE 4

INCORPORATION OF MODIFIED NUCLEOTIDE TRIPHOSPHATES

| Modification | COND #1 | COND #2 | COND #3 | COND #4 | COND #5 | COND #6 | COND #7 | COND #8 | COND #9 | COND #10 | COND #11 | COND #12 |
|---|---|---|---|---|---|---|---|---|---|---|---|---|
| 2'-NH$_2$-ATP | 1 | 2 | 3 | 5 | 2 | 4 | 1 | 2 | 10 | 11 | 5 | 9 |
| 2'-NH$_2$-CTP | 11 | 37 | 45 | 64 | 25 | 70 | 26 | 54 | 292 | 264 | 109 | 244 |
| 2'-NH$_2$-GTP | 4 | 7 | 6 | 14 | 5 | 17 | 3 | 16 | 10 | 21 | 9 | 16 |
| 2'-NH$_2$-UTP | 14 | 45 | 4 | 100 | 85 | 82 | 48 | 88 | 20 | 418 | 429 | 440 |
| 2'-dATP | 9 | 3 | 19 | 23 | 9 | 24 | 6 | 3 | 84 | 70 | 28 | 51 |
| 2'-dCTP | 1 | 10 | 43 | 46 | 35 | 47 | 27 | 127 | 204 | 212 | 230 | 235 |
| 2'-dGTP | 6 | 10 | 9 | 15 | 9 | 12 | 8 | 34 | 38 | 122 | 31 | 46 |
| 2'-dTTP | 9 | 9 | 14 | 18 | 13 | 18 | 8 | 15 | 116 | 114 | 59 | 130 |
| 2'-O-Me-ATP | 0 | 0 | 0 | 0 | 0 | 0 | 1 | 1 | 2 | 2 | 2 | 2 |
| 2'-O-Me-CTP | no data compared to ribo; incorporates at low level | | | | | | | | | | | |
| 2'-O-Me-GTP | 4 | 3 | 4 | 4 | 4 | 4 | 2 | 4 | 4 | 5 | 4 | 5 |
| 2'-O-Me-UTP | 55 | 52 | 39 | 38 | 41 | 48 | 55 | 71 | 93 | 103 | 81 | 77 |
| 2'-O-Me-DAP | 4 | 4 | 3 | 4 | 4 | 5 | 4 | 3 | 4 | 5 | 5 | 5 |
| 2'-NH$_2$-DAP | 0 | 0 | 1 | 1 | 1 | 1 | 1 | 0 | 0 | 0 | 0 | 0 |
| ala-2'-NH$_2$-UTP | 2 | 2 | 2 | 2 | 3 | 4 | 14 | 18 | 15 | 20 | 13 | 14 |
| phe-2'-NH$_2$-UTP | 8 | 12 | 7 | 7 | 8 | 8 | 4 | 10 | 6 | 6 | 10 | 6 |
| 2'-β NH$_2$-ala-UTP | 65 | 48 | 25 | 17 | 21 | 21 | 220 | 223 | 265 | 300 | 275 | 248 |
| 2'-F-ATP | 227 | 252 | 98 | 103 | 100 | 116 | 288 | 278 | 471 | 198 | 317 | 185 |
| 2'-F-GTP | 39 | 44 | 17 | 30 | 17 | 26 | 172 | 130 | 375 | 447 | 377 | 438 |
| 2'-C-allyl-UTP | 3 | 2 | 2 | 3 | 3 | 2 | 3 | 3 | 3 | 2 | 3 | 3 |
| 2'-O-NH$_2$-UTP | 6 | 8 | 5 | 5 | 4 | 5 | 16 | 23 | 24 | 24 | 19 | 24 |
| 2'-O-MTM-ATP | 0 | 1 | 0 | 0 | 0 | 0 | 1 | 0 | 0 | 0 | 0 | 0 |
| 2'-O-MTM-CTP | 2 | 2 | 1 | 1 | 1 | 1 | 3 | 4 | 5 | 4 | 5 | 3 |
| 2'-O-MTM-GTP | 6 | 1 | 1 | 3 | 1 | 2 | 0 | 1 | 1 | 3 | 1 | 4 |

TABLE 5

INCORPORATION OF MODIFIED NUCLEOTIDE TRIPHOSPHATES USING WILD TYPE BACTERIOPHAGE T7 POLYMERASE

| Modification | label | % ribo control |
|---|---|---|
| 2'-NH$_2$-GTP | ATP | 4% |
| 2'-dGTP | ATP | 3% |
| 2'-O-Me-GTP | ATP | 3% |
| 2'-F-GTP | ATP | 4% |
| 2'-O-MTM-GTP | ATP | 3% |
| 2'-NH$_2$-UTP | ATP | 39% |
| 2'-dTTP | ATP | 5% |
| 2'-O-Me-UTP | ATP | 3% |
| ala-2'-NH$_2$-UTP | ATP | 2% |
| phe-2'-NH$_2$-UTP | ATP | 1% |
| 2'-β-ala-NH$_2$-UTP | ATP | 3% |
| 2'-C-allyl-UTP | ATP | 2% |
| 2'-O-NH$_2$-UTP | ATP | 1% |
| 2'-O-MTM-UTP | ATP | 64% |
| 2'-NH$_2$-ATP | GTP | 1% |
| 2'-O-MTM-ATP | GTP | 1% |
| 2'-NH$_2$-CTP | GTP | 59% |
| 2'-dCTP | GTP | 40% |

TABLE 6a

Incorporation of 2'-his-UTP and Modified CTP's

| modification | 2'-his-UTP | rUTP |
|---|---|---|
| CTP | 16.1 | 100 |
| 2'-amino-CTP | 9.5* | 232.7 |
| 2'-deoxy-CTP | 9.6* | 130.1 |
| 2'-OMe-CTP | 1.9 | 6.2 |
| 2'-MTM-CTP | 5.9 | 5.1 |
| control | 1.2 | |

TABLE 6b

Incorporation of 2'-his-UTP, 2-amino CTP, and Modified ATP's

| modification | 2'-his-UTP and 2'-amino-CTP | rUTP and rCTP |
|---|---|---|
| ATP | 15.7 | 100 |
| 2'-amino-ATP | 2.4 | 28.9 |
| 2'-deoxy-ATP | 2.3 | 146.3 |
| 2'-OMe-ATP | 2.7 | 15 |
| 2'-F-ATP | 4 | 222.6 |
| 2'-MTM-ATP | 4.7 | 15.3 |

TABLE 6b-continued

Incorporation of 2'-his-UTP, 2-amino CTP, and Modified ATP's

| modification | 2'-his-UTP and 2'-amino-CTP | rUTP and rCTP |
|---|---|---|
| 2'-OMe-DAP | 1.9 | 5.7 |
| 2'-amino-DAP | 8.9* | 9.6 |

Numbers shown are a percentage of incorporation compared to the all-RNA control
*Bold number indicates best observed rate of modified nucleotide triphosphate incorporation

TABLE 7

INCORPORATION OF 2'-his-UTP, 2'-NH$_2$-CTP, 2'-NH$_2$-DAP, and rGTP USING VARIOUS REACTION CONDITIONS

| Conditions | compared to all rNTP |
|---|---|
| 7 | 8.7* |
| 8 | 7* |
| 9 | 2.3 |
| 10 | 2.7 |
| 11 | 1.6 |
| 12 | 2.5 |

Numbers shown are a percentage of incorporation compared to the all-RNA control
*Two highest levels of incorporation contained both methanol and LiCl

TABLE 8

Selection of Oligonucleotides with Ribozyme Activity

| pool | Generation | time | substrate remaining (%) | time | Substrate remaining (%) |
|---|---|---|---|---|---|
| N60 | 0 | 4 hr | 100.00 | 24 hr | 100.98 |
| N60 | 14 | 4 hr | 99.67 | 24 hr | 97.51 |
| N60 | 15 | 4 hr | 98.76 | 24 hr | 96.76 |
| N60 | 16 | 4 hr | 97.09 | 24 hr | 96.60 |
| N60 | 17 | 4 hr | 79.50 | 24 hr | 64.01 |
| N40 | 0 | 4 hr | 99.89 | 24 hr | 99.78 |
| N40 | 10 | 4 hr | 99.74 | 24 hr | 99.42 |
| N40 | 11 | 4 hr | 97.18 | 24 hr | 90.38 |
| N40 | 12 | 4 hr | 61.64 | 24 hr | 44.54 |
| N40 | 13 | 4 hr | 54.28 | 24 hr | 36.46 |
| N20 | 0 | 4 hr | 99.18 | 24 hr | 100.00 |
| N20 | 11 | 4 hr | 100.00 | 24 hr | 100.00 |
| N20 | 12 | 4 hr | 99.51 | 24 hr | 100.00 |
| N20 | 13 | 4 hr | 90.63 | 24 hr | 84.89 |
| N20 | 14 | 4 hr | 91.16 | 24 hr | 85.92 |
| N60B | 0 | 4 hr | 100.00 | 24 hr | 100.00 |
| N60B | 1 | 4 hr | 100.00 | 24 hr | 100.00 |
| N60B | 2 | 4 hr | 100.00 | 24 hr | 100.00 |
| N60B | 3 | 4 hr | 100.00 | 24 hr | 100.00 |
| N60B | 4 | 4 hr | 99.24 | 24 hr | 100.00 |
| N60B | 5 | 4 hr | 97.81 | 24 hr | 96.65 |
| N60B | 6 | 4 hr | 89.95 | 24 hr | 77.14 |

TABLE 9

Kinetic Activity of Combinatorial Libraries

| Pool | Generation | $k_{obs}$ (min$^{-1}$) |
|---|---|---|
| N60 | 17 | 0.0372 |
|  | 18 | 0.0953 |
|  | 19 | 0.0827 |
| N40 | 12 | 0.0474 |
|  | 13 | 0.037 |
|  | 14 | 0.065 |
|  | 15 | 0.0254 |
| N20 | 13 | 0.0359 |
|  | 14 | 0.0597 |
|  | 15 | 0.0549 |
|  | 16 | 0.0477 |
| N60B | 6 | 0.0209 |
|  | 7 | 0.0715 |
|  | 8 | 0.0379 |

TABLE 10

Kinetic Activity of Clones within N60 and N40 Combinatorial Libraries

| clone | library | activity (min$^{-1}$) | $k_{rel}$ |
|---|---|---|---|
| G18 | N60 | 0.00226 | 1.00 |
| 0-2 | N60 | 0.0389 | 17.21 |
| 0-3 | N60 | 0.000609 | 0.27 |
| 0-5 | N60 | 0.000673 | 0.30 |
| 0-7 | N60 | 0.00104 | 0.46 |
| 0-8 | N60 | 0.000739 | 0.33 |
| 0-11 | N60 | 0.0106 | 4.69 |
| 0-12 | N60 | 0.00224 | 0.99 |
| 0-13 | N60 | 0.0255 | 11.28 |
| 0-14 | N60 | 0.000878 | 0.39 |
| 0-15 | N60 | 0.0000686 | 0.03 |
| 0-21 | N60 | 0.0109 | 4.82 |
| 0-22 | N60 | 0.000835 | 0.37 |
| 0-24 | N60 | 0.000658 | 0.29 |
| 0-28 | N40 | 0.000741 | 0.33 |
| 0-35 | N40 | 0.00658 | 2.91 |
| 3-1 | N40 | 0.0264 | 11.68 |
| 3-3 | N40 | 0.000451 | 0.20 |
| 3-7 | N40 | 0.000854 | 0.38 |
| 3-15 | N40 | 0.000832 | 0.37 |

TABLE 11

Effect of Magnesium Concentration of the Cleavage Rate of N20

| [Mg++] | $k_{obs}$ (min$^{-1}$) |
|---|---|
| 25 | 0.0259 |
| 20 | 0.0223 |
| 15 | 0.0182 |
| 10 | 0.0208 |
| 5 | 0.0121 |
| 2 | 0.00319 |
| 2 | 0.00226 |

TABLE XII

Class I Enzymatic Nucleic Acid Motifs Targeting H

| Gene Name | Site | Chem Seq |
|---|---|---|
| HCV.R1A | 6 | ggagugucgc GgaggaaacucC CU UCAAGGACAUCGUCCGGG cccau B |
| HCV.R1A | 56 | acgcuuucug Ggaggaaacucc CU UCAAGGACAUCGUCCGGG gugaa B |
| HCV.R1A | 75 | auacuaacgc Ggaggaaacucc CU UCAAGGACAUCGUCCGGG auggc B |
| HCV.R1A | 76 | cauacuaacg Ggaggaaacucc CU UCAAGGACAUCGUCCGGG caugg B |
| HCV.R1A | 95 | cuggaggcug Ggaggaaacucc CU UCAAGGACAUCGUCCGGG acgac B |
| HCV.R1A | 138 | accgguuccg Ggaggaaacucc CU UCAAGGACAUCGUCCGGG agacc B |
| HCV.R1A | 146 | guguacucac Ggaggaaacucc CU UCAAGGACAUCGUCCGGG gguuc B |
| HCV.R1A | 158 | cuggcaauuc Ggaggaaacucc CU UCAAGGACAUCGUCCGGG ggugu B |
| HCV.R1A | 164 | gucguccggg Ggaggaaacucc CU UCAAGGACAUCGUCCGGG aauuc B |
| HCV.R1A | 176 | agaaaggccc Ggaggaaacucc CU UCAAGGACAUCGUCCGGG ggucg B |
| HCV.R1A | 177 | aagaaaggac Ggaggaaacucc CU UCAAGGACAUCGUCCGGG cgguc B |
| HCV.R1A | 209 | cccaaaucuc Ggaggaaacucc CU UCAAGGACAUCGUCCGGG aggca B |
| HCV.R1A | 237 | acucggcuag Ggaggaaacucc CU UCAAGGACAUCGUCCGGG agucu B |
| HCV.R1A | 254 | uuucgcgacc Ggaggaaacucc CU UCAAGGACAUCGUCCGGG aacac B |
| HCV.R1A | 255 | cuuucgcgac Ggnggaaacucc CU UCAAGGACAUCGUCCGGG caaca B |
| HCV.R1A | 259 | aggccuuucg Ggaggaaacucc CU UCAAGGACAUCGUCCGGG gaccc B |
| HCV.R1A | 266 | uaccacaagg Ggaggaaacucc CU UCAAGGACAUCGUCCGGG cuuuc B |
| HCV.R1A | 273 | caggcaguac Ggaggaaacucc CU UCAAGGACAUCGUCCGGG acaag B |
| HCV.R1A | 288 | ucgcaagcac Ggaggaaacucc CU UCAAGGACAUCGUCCGGG cuuuc B |
| HCV.R1A | 291 | cacucgcaag Ggaggaaacucc CU UCAAGGACAUCGUCCGGG acccu B |
| HCV.R1A | 7 | uggagugucg Ggaggaaacucc CU UCAAGGACAUCGUCCGGG cccca B |
| HCV.R1A | 119 | auggcucucc Ggaggaaacucc CU UCAAGGACAUCGUCCGGG gggag B |
| HCV.R1A | 120 | uauggcucuc Ggaggaaacucc CU UCAAGGACAUCGUCCGGG cggga B |
| HCV.R1A | 133 | uuccgcagac Ggaggaaacucc CU UCAAGGACAUCGUCCGGG acuau B |
| HCV.R1A | 140 | ucaccgguuc Ggaggaaacucc CU UCAAGGACAUCGUCCGGG gcaga B |
| HCV.R1A | 188 | cgggguuauc Ggaggaaacucc CU UCAAGGACAUCGUCCGGG aagaa B |
| HCV.R1A | 198 | aggcauugag Ggaggaaacucc CU UCAAGGACAUCGUCCGGG ggggu B |
| HCV.R1A | 205 | aaucucccgg Ggaggaaacucc CU UCAAGGACAUCGUCCGGG auuga B |
| HCV.R1A | 217 | ggggcacgcc Ggaggaaacucc CU UCAAGGACAUCGUCCGGG aaauc B |
| HCV.R1A | 218 | gggggcacgc Ggaggaaacucc CU UCAAGGACAUCGUCCGGG caaau B |
| HCV.R1A | 219 | cgggggcacg Ggaggaaacucc CU UCAAGGACAUCGUCCGGG ccaaa B |
| HCV.R1A | 223 | cuugcggggg Ggaggaaacucc CU UCAAGGACAUCGUCCGGG acgcc B |
| HCV.R1A | 229 | agcagucuug Ggaggaaacucc CU UCAAGGACAUCGUCCGGG ggggg B |
| HCV.R1A | 279 | cccuaucagg Ggaggaaacucc CU UCAAGGACAUCGUCCGGG aguac B |
| HCV.R1A | 295 | ggggcacucg Ggaggaaacucc CU UCAAGGACAUCGUCCGGG aagca B |
| HCV.R1A | 301 | ccucccgggg Ggaggaaacucc CU UCAAGGACAUCGUCCGGG acucg B |
| HCV.R1A | 306 | cgagcccccc Ggaggaaacucc CU UCAAGGACAUCGUCCGGG ggggc B |
| HCV.R1A | 307 | acgagaccuc Ggaggaaacucc CU UCAAGGACAUCGUCCGGG cgggg B |
| No Ribo | | GgaaaggugugcaaccggagucaucauaauggcuucCCUUCaaggaCaUCgCCg ggacggcB |
| Ribo | | GGAAAGGUGUGCAACCGGAGUCAUCAUAAUHHCUCCCUUCAAHHACAUCHUC CGGGACGGCB | lower case = 2'OMe
U, C = 2'-amino-U, 2'-amino-C
G,A = ribo G,A
B = inverted abasic

TABLE XIII

Additional Class II enzymatic nucleic acid Motifs

| Class II Motif ID | Sequence |
|---|---|
| A2 | GGGAGGAGGAAGUGCCUGGUCAGUCACACCGAGACUGGCAGACGCUGAAACC GCCGCGCUCGCUCCCAGUCC |
| A12 | GGGAGGAGGAAGUGCCUGGUAGUAAUAUAAUCGUUACUACGAGUGCAAGGUC GCCGCGCUCGCUCCCAGUCC |
| A11 | GGGAGGAGGAAGUGCCUGGUAGUUGCCCGAACUGUGACUACGAGUGAGGUC GCCGCGCUCGCUCCCAGUCC |
| B14 | GGGAGGAGGAAGUGCCUGGCGAUCAGAUGAGAUGAUGGCAGACGCAGAGACC GCCGCGCUCGCUCCCAGUCC |
| B10 | GGGAGGAGGAAGUGCCUGGCGACUGAUACGAAAAGUCGCAGUUUCGAAACC GCCGCGCUCGCUCCCAGUCC |
| B21 | GGGAGGAGGAAGUGCCUGGCGACUGAUACGAAAAGUCGCAGGUUUCGAAACC GCCGCGCUCGCUCCCAGUCC |
| B7 | GGGAGGAGGAAGUGCCUUGGCUCAGCAUAAGUGAGCAGAUUGCGACACC GCCGCGCUCGCUCCCAGUCC |
| C8 | GGGAGGAGGAAGUGCCUUGGUCAUUAGGUGACAAACGUAUACUGAACACU GCCGCGCUCGCUCCCAGUCC |

What is claimed is:

1. An enzymatic nucleic acid molecule having formula II:

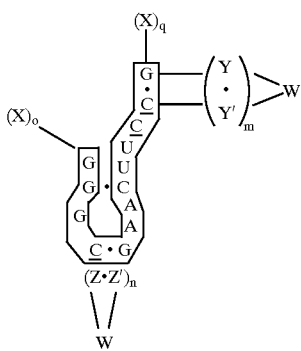

wherein each X, Y, and Z represents independently a nucleotide which may be the same or different; q is an integer ranging from 3 to 100; m is an integer ranging from 1 to 10; n is an integer ranging from 1 to 10; o is an integer ranging from 3 to 100; Z' is a nucleotide complementary to Z; Y' is a nucleotide complementary to Y; each X(q) and X(o) are oligonucleotides which are of sufficient length to stably interact independently with a target RNA sequence of Hepatitis C virus; W is a linker ranging from 2 to 70 nucleotides; A, U, G, and C represent nucleotides; C is 2'-deoxy-2'-amino cytidine, or 2'-O-amino cytidine; and represents a chemical bond or chemical linkage.

2. The nucleic acid of claim 1, wherein q is selected from the group consisting of 4, 5, 6, 7, 8, 9, 10, 11, 12, and 15.

3. The nucleic acid of claim 1, wherein m is selected from the group consisting of 2, 3, 4, 5, 6, and 7.

4. The nucleic acid of claim 1, wherein n is selected from the group consisting of 2, 3, 4, 5, 6, and 7.

5. The nucleic acid of claim 1, wherein o is selected from the group consisting of 3, 4, 5, 6, 7, 8, 9, 10, 11, 12, and 15.

6. The nucleic acid of claim 1, wherein q and o are of the same length.

7. The nucleic acid of claim 1, wherein q and o are of different length.

8. The nucleic acid of claim 1, wherein said chemical linkage is selected from the group consisting of phosphate ester linkage, amide linkage, phosphorothioate, and phosphorodithioate.

9. The enzymatic nucleic acid molecule of claim 1, wherein said enzymatic nucleic acid molecule comprises at least one ribonucleotide.

10. The enzymatic nucleic acid molecule of claim 1, wherein said enzymatic nucleic acid molecule comprises no ribonucleotide residues.

11. The enzymatic nucleic acid molecule of claim 1, wherein said enzymatic nucleic acid molecule comprises at least three 2'-deoxy-2'-amino or 2'-O-amino modified nucleotides.

12. The enzymatic nucleic acid molecule of claim 1, wherein said enzymatic nucleic acid molecule further comprises at least three phosphorothioate linkages.

13. The enzymatic nucleic acid molecule of claim 12, wherein said phosphorothioate linkages are at the 5'-end of said enzymatic nucleic acid molecule.

14. The enzymatic nucleic acid molecule of claim 1, wherein said enzymatic nucleic acid molecule further comprises a 5'-cap or a 3'-cap or both a 5'-cap and a 3'-cap.

15. The enzymatic nucleic acid molecule of claim 14, wherein said enzymatic nucleic acid comprises a 5'-cap having a phosphorothioate linkage between said 5'-cap and the 5'-end nucleotide of the enzymatic nucleic acid.

16. The enzymatic nucleic acid molecule of claim 14, wherein said enzymatic nucleic acid comprises a 3'-cap, wherein said 3'-cap is an inverted abasic moiety.

17. A method for inhibiting expression of a Hepatitis C virus gene in a cell, comprising the step of administering to said cell the enzymatic nucleic acid molecule of claim 1 under conditions suitable for said inhibition.

18. A method of cleaving a separate RNA encoded by Hepatitis C virus comprising, contracting the enzymatic nucleic acid molecule of claim 1 with said separate Hepatitis C virus RNA under conditions suitable for the cleavage of said separate Hepatitis C virus RNA.

19. The method of claim 18, wherein said cleavage is carried out in the presence of a divalent cation.

20. The method of claim 18, wherein said divalent cation is $Mg^{2+}$.

* * * * *

SEQUENCE LISTING

<160> NUMBER OF SEQ ID NOS: 69

<210> SEQ ID NO 1
<211> LENGTH: 48
<212> TYPE: RNA
<213> ORGANISM: Artificial Sequence
<220> FEATURE:
<223> OTHER INFORMATION: Description of Artificial Sequence:
      Enzymatic Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 1
ggagugucgc ggaggaaacu cccuucaagg acaucguccg ggcccaun                48

<210> SEQ ID NO 2
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 2
acgcuuucug ggaggaaacu cccuucaagg acaucguccg gggugaan                48

```
<210> SEQ ID NO 3
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 3
auacuaacgc ggaggaaacu cccuucaagg acaucguccg ggauggcn                    48

<210> SEQ ID NO 4
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 4
cauacuaacg ggaggaaacu cccuucaagg acaucguccg ggcauggn                    48

<210> SEQ ID NO 5
<211> LENGTH: 48
<212> TYPE: RNA
<213> ORGANISM: Artificial Sequence
<220> FEATURE:
```

```
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 5
cuggaggcug ggaggaaacu cccuucaagg acaucguccg ggacgacn                    48

<210> SEQ ID NO 6
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 6
accgguuccg ggaggaaacu cccuucaagg acaucguccg ggagaccn                    48

<210> SEQ ID NO 7
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
```

```
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 7
guguacucac ggaggaaacu cccuucaagg acaucguccg ggggguucn                48

<210> SEQ ID NO 8
<211> LENGTH: 48
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 8
cuggcaauuc ggaggaaacu cccuucaagg acaucguccg ggggugun                48

<210> SEQ ID NO 9
<211> LENGTH: 48
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
```

```
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 9
gucguccugg ggaggaaacu cccuucaagg acaucguccg ggaauucn                48

<210> SEQ ID NO 10
<211> LENGTH: 48
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 10
agaaaggacc ggaggaaacu cccuucaagg acaucguccg ggggucgn                48

<210> SEQ ID NO 11
<211> LENGTH: 48
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
```

```
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 11
aagaaaggac ggaggaaacu cccuucaagg acaucguccg ggcggucn                       48

<210> SEQ ID NO 12
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 12
cccaaaucuc ggaggaaacu cccuucaagg acaucguccg ggaggcan                       48

<210> SEQ ID NO 13
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
```

```
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 13
acucggcuag ggaggaaacu cccuucaagg acaucguccg ggagucun                      48

<210> SEQ ID NO 14
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 14
uuucgcgacc ggaggaaacu cccuucaagg acaucguccg ggaacacn                      48

<210> SEQ ID NO 15
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
```

```
<223> OTHER INFORMATION: n stands for inverted deoxyabasic derivative

<400> SEQUENCE: 15
cuuucgcgac ggaggaaacu cccuucaagg acaucguccg ggcaacan          48

<210> SEQ ID NO 16
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 16
aggccuuucg ggaggaaacu cccuucaagg acaucguccg gggacccn          48

<210> SEQ ID NO 17
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 17
uaccacaagg ggaggaaacu cccuucaagg acaucguccg ggcuuucn          48
```

```
<210> SEQ ID NO 18
<211> LENGTH: 48
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 18
caggcaguac ggaggaaacu cccuucaagg acaucguccg ggacaagn                48

<210> SEQ ID NO 19
<211> LENGTH: 48
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 19
ucgcaagcac ggaggaaacu cccuucaagg acaucguccg ggcuaucn                48

<210> SEQ ID NO 20
<211> LENGTH: 48
<212> TYPE: RNA
<213> ORGANISM: Artificial Sequence
<220> FEATURE:
```

```
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 20
cacucgcaag ggaggaaacu cccuucaagg acaucguccg ggacccun            48

<210> SEQ ID NO 21
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 21
uggagugucg ggaggaaacu cccuucaagg acaucguccg ggccccan            48

<210> SEQ ID NO 22
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
```

```
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 22
auggcucucc ggaggaaacu cccuucaagg acaucguccg gggggagn         48

<210> SEQ ID NO 23
<211> LENGTH: 48
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 23
uauggcucuc ggaggaaacu cccuucaagg acaucguccg ggcgggan         48

<210> SEQ ID NO 24
<211> LENGTH: 48
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
```

```
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 24
uuccgcagac ggaggaaacu cccuucaagg acaucguccg ggacuaun         48

<210> SEQ ID NO 25
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 25
ucaccgguuc ggaggaaacu cccuucaagg acaucguccg gggcagan         48

<210> SEQ ID NO 26
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
```

```
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 26
cggguuuauc ggaggaaacu cccuucaagg acaucguccg ggaagaan                    48

<210> SEQ ID NO 27
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 27
aggcauugag ggaggaaacu cccuucaagg acaucguccg gggggun                     48

<210> SEQ ID NO 28
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
```

```
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 28
aaucuccagg ggaggaaacu cccuucaagg acaucguccg ggauugan                 48

<210> SEQ ID NO 29
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 29
ggggcacgcc ggaggaaacu cccuucaagg acaucguccg ggaaaucn                 48

<210> SEQ ID NO 30
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
```

```
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 30
gggggcacgc ggaggaaacu cccuucaagg acaucguccg ggcaaaun            48

<210> SEQ ID NO 31
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 31
cgggggcacg ggaggaaacu cccuucaagg acaucguccg ggccaaan            48

<210> SEQ ID NO 32
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative
```

-continued

```
<400> SEQUENCE: 32
cuugcggggg ggaggaaacu cccuucaagg acaucguccg ggacgccn                48

<210> SEQ ID NO 33
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 33
agcagucuug ggaggaaacu cccuucaagg acaucguccg ggggggn                 48

<210> SEQ ID NO 34
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 34
cccuaucagg ggaggaaacu cccuucaagg acaucguccg ggaguacn                48
```

```
<210> SEQ ID NO 35
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 35
ggggcacucg ggaggaaacu cccuucaagg acaucguccg ggaagcan              48

<210> SEQ ID NO 36
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 36
ccucccgggg ggaggaaacu cccuucaagg acaucguccg ggacucgn              48

<210> SEQ ID NO 37
<211> LENGTH: 48
<212> TYPE: RNA
<213> ORGANISM: Artificial Sequence
<220> FEATURE:
```

```
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 37
cgagaccucc ggaggaaacu cccuucaagg acaucguccg gggggcn            48

<210> SEQ ID NO 38
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(10)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (43)..(47)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (48)..(48)
<223> OTHER INFORMATION: n stands for inverted deoxyabasic derivative

<400> SEQUENCE: 38
acgagaccuc ggaggaaacu cccuucaagg acaucguccg ggcggggn           48

<210> SEQ ID NO 39
<211> LENGTH: 62
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (2)..(36)
<223> OTHER INFORMATION: 2'-O-Methyl
```

```
<221> NAME/KEY: misc_feature
<222> LOCATION: (42)..(46)
<223> OTHER INFORMATION: 2'-O-Methyl
<221> NAME/KEY: misc_feature
<222> LOCATION: (48)..(48)
<223> OTHER INFORMATION: 2'-O-Methyl
<221> NAME/KEY: misc_feature
<222> LOCATION: (51)..(51)
<223> OTHER INFORMATION: 2'-O-Methyl
<221> NAME/KEY: misc_feature
<222> LOCATION: (54)..(61)
<223> OTHER INFORMATION: 2'-O-Methyl
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (32)..(32)
<223> OTHER INFORMATION: 2'-deoxy-2'-amino
<221> NAME/KEY: misc_feature
<222> LOCATION: (34)..(35)
<223> OTHER INFORMATION: 2'-deoxy-2'-amino
<221> NAME/KEY: misc_feature
<222> LOCATION: (37)..(39)
<223> OTHER INFORMATION: 2'-deoxy-2'-amino
<221> NAME/KEY: misc_feature
<222> LOCATION: (62)..(62)
<223> OTHER INFORMATION: n stands for inverted deoxyabasic derivative

<400> SEQUENCE: 39
ggaaaggugu gcaaccggag ucaucauaau ggcuucccuu caaggacauc gccgggacgg      60 cn                                                                    62

<210> SEQ ID NO 40
<211> LENGTH: 62
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (8)..(8)
<223> OTHER INFORMATION: 2'-deoxy-2'-amino
<221> NAME/KEY: misc_feature
<222> LOCATION: (10)..(10)
<223> OTHER INFORMATION: 2'-deoxy-2'-amino
<221> NAME/KEY: misc_feature
<222> LOCATION: (12)..(12)
<223> OTHER INFORMATION: 2'-deoxy-2'-amino
<221> NAME/KEY: misc_feature
<222> LOCATION: (15)..(16)
<223> OTHER INFORMATION: 2'-deoxy-2'-amino
<221> NAME/KEY: misc_feature
<222> LOCATION: (21)..(22)
<223> OTHER INFORMATION: 2'-deoxy-2'-amino
<221> NAME/KEY: misc_feature
<222> LOCATION: (24)..(25)
<223> OTHER INFORMATION: 2'-deoxy-2'-amino
<221> NAME/KEY: misc_feature
<222> LOCATION: (27)..(27)
<223> OTHER INFORMATION: 2'-deoxy-2'-amino
<221> NAME/KEY: misc_feature
<222> LOCATION: (30)..(30)
<223> OTHER INFORMATION: 2'-deoxy-2'-amino
<221> NAME/KEY: misc_feature
<222> LOCATION: (33)..(40)
<223> OTHER INFORMATION: 2'-deoxy-2'-amino
<221> NAME/KEY: misc_feature
<222> LOCATION: (46)..(46)
<223> OTHER INFORMATION: 2'-deoxy-2'-amino
<221> NAME/KEY: misc_feature
<222> LOCATION: (48)..(49)
<223> OTHER INFORMATION: 2'-deoxy-2'-amino
<221> NAME/KEY: misc_feature
<222> LOCATION: (51)..(53)
<223> OTHER INFORMATION: 2'-deoxy-2'-amino
<221> NAME/KEY: misc_feature
```

```
<222> LOCATION: (58)..(58)
<223> OTHER INFORMATION: 2'-deoxy-2'-amino
<221> NAME/KEY: misc_feature
<222> LOCATION: (61)..(61)
<223> OTHER INFORMATION: 2'-deoxy-2'-amino
<221> NAME/KEY: misc_feature
<222> LOCATION: (62)..(62)
<223> OTHER INFORMATION: n stands for inverted deoxyabasic derivative

<400> SEQUENCE: 40
ggaaaggugu gcaaccggag ucaucauaau ggcucccuuc aaggacaucg uccgggacgg    60 cn                                                                  62

<210> SEQ ID NO 41
<211> LENGTH: 72
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 41
gggaggagga agugccuggu cagucacacc gagacuggca gacgcugaaa ccgccgcgcu    60
cgcucccagu cc                                                       72

<210> SEQ ID NO 42
<211> LENGTH: 72
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 42
gggaggagga agugccuggu aguaauauaa ucguuacuac gagugcaagg ucgccgcgcu    60
cgcucccagu cc                                                       72

<210> SEQ ID NO 43
<211> LENGTH: 71
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 43
gggaggagga agugccuggu aguugcccga acugugacua cgagugaggu cgccgcgcuc    60
gcucccaguc c                                                        71

<210> SEQ ID NO 44
<211> LENGTH: 72
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 44
gggaggagga agugccuggc gaucagauga gaugauggca gacgcagaga ccgccgcgcu    60
cgcucccagu cc                                                       72

<210> SEQ ID NO 45
<211> LENGTH: 71
<212> TYPE: RNA
```

```
<213> ORGANISM: Artificial Sequence
<220> FEATURE:
<223> OTHER INFORMATION: Description of Artificial Sequence:  Enzymatic
      Nucleic Acid

<400> SEQUENCE: 45
gggaggagga agugccuggc gacugauacg aaaagucgca guuucgaaac cgccgcgcuc    60
gcucccaguc c                                                        71

<210> SEQ ID NO 46
<211> LENGTH: 72
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 46
gggaggagga agugccuggc gacugauacg aaaagucgca gguuucgaaa ccgccgcgcu    60
cgcucccagu cc                                                       72

<210> SEQ ID NO 47
<211> LENGTH: 69
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 47
gggaggagga agugccuugg cucagcauaa gugagcagau ugcgacaccg ccgcgcucgc    60
ucccagucc                                                           69

<210> SEQ ID NO 48
<211> LENGTH: 71
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 48
gggaggagga agugccuugg ucauuaggau gacaaacgua uacugaacac ugccgcgcuc    60
gcucccaguc c                                                        71

<210> SEQ ID NO 49
<211> LENGTH: 48
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(8)
<223> OTHER INFORMATION: 2'-O-Methyl
<221> NAME/KEY: misc_feature
<222> LOCATION: (12)..(21)
<223> OTHER INFORMATION: 2'-O-Methyl
<221> NAME/KEY: misc_feature
<222> LOCATION: (32)..(37)
<223> OTHER INFORMATION: 2'-O-Methyl
<221> NAME/KEY: misc_feature
<222> LOCATION: (44)..(48)
<223> OTHER INFORMATION: 2'-O-Methyl
<221> NAME/KEY: misc_feature
<222> LOCATION: (9)..(10)
<223> OTHER INFORMATION: 2'-deoxy-2'-amino
```

```
<221> NAME/KEY: misc_feature
<222> LOCATION: (22)..(26)
<223> OTHER INFORMATION: 2'-deoxy-2'-amino
<221> NAME/KEY: misc_feature
<222> LOCATION: (38)..(40)
<223> OTHER INFORMATION: 2'-deoxy-2'-amino

<400> SEQUENCE: 49
gugugcaacc ggaggaaacu cccuucaagg acgaaagucc gggacggg          48

<210> SEQ ID NO 50
<211> LENGTH: 16
<212> TYPE: RNA
<213> ORGANISM: Artificial Sequence
<220> FEATURE:
<223> OTHER INFORMATION: Description of Artificial Sequence:  Nucleic
      Acid Substrate

<400> SEQUENCE: 50 gccgugggu gcacac                                              16

<210> SEQ ID NO 51
<211> LENGTH: 73
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (15)..(16)
<223> OTHER INFORMATION: 2'-deoxy-2'-amino
<221> NAME/KEY: misc_feature
<222> LOCATION: (21)..(21)
<223> OTHER INFORMATION: 2'-deoxy-2'-amino
<221> NAME/KEY: misc_feature
<222> LOCATION: (32)..(33)
<223> OTHER INFORMATION: 2'-deoxy-2'-amino
<221> NAME/KEY: misc_feature
<222> LOCATION: (41)..(41)
<223> OTHER INFORMATION: 2'-deoxy-2'-amino
<221> NAME/KEY: misc_feature
<222> LOCATION: (46)..(46)
<223> OTHER INFORMATION: 2'-deoxy-2'-amino
<221> NAME/KEY: misc_feature
<222> LOCATION: (52)..(52)
<223> OTHER INFORMATION: 2'-deoxy-2'-amino
<221> NAME/KEY: misc_feature
<222> LOCATION: (55)..(56)
<223> OTHER INFORMATION: 2'-deoxy-2'-amino
<221> NAME/KEY: misc_feature
<222> LOCATION: (58)..(58)
<223> OTHER INFORMATION: 2'-deoxy-2'-amino
<221> NAME/KEY: misc_feature
<222> LOCATION: (60)..(60)
<223> OTHER INFORMATION: 2'-deoxy-2'-amino
<221> NAME/KEY: misc_feature
<222> LOCATION: (62)..(62)
<223> OTHER INFORMATION: 2'-deoxy-2'-amino
<221> NAME/KEY: misc_feature
<222> LOCATION: (64)..(64)
<223> OTHER INFORMATION: 2'-deoxy-2'-amino
<221> NAME/KEY: misc_feature
<222> LOCATION: (66)..(68)
<223> OTHER INFORMATION: 2'-deoxy-2'-amino
<221> NAME/KEY: misc_feature
<222> LOCATION: (72)..(73)
<223> OTHER INFORMATION: 2'-deoxy-2'-amino

<400> SEQUENCE: 51
gggaggagga agugccuggu cauaggauuu ccuuugugg cgagucaagg ucugccgcgc    60
ucgcucccag ucc                                                     73
```

```
<210> SEQ ID NO 52
<211> LENGTH: 73
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (15)..(16)
<223> OTHER INFORMATION: 2'-deoxy-2'-amino
<221> NAME/KEY: misc_feature
<222> LOCATION: (20)..(20)
<223> OTHER INFORMATION: 2'-deoxy-2'-amino
<221> NAME/KEY: misc_feature
<222> LOCATION: (23)..(23)
<223> OTHER INFORMATION: 2'-deoxy-2'-amino
<221> NAME/KEY: misc_feature
<222> LOCATION: (26)..(26)
<223> OTHER INFORMATION: 2'-deoxy-2'-amino
<221> NAME/KEY: misc_feature
<222> LOCATION: (30)..(31)
<223> OTHER INFORMATION: 2'-deoxy-2'-amino
<221> NAME/KEY: misc_feature
<222> LOCATION: (41)..(41)
<223> OTHER INFORMATION: 2'-deoxy-2'-amino
<221> NAME/KEY: misc_feature
<222> LOCATION: (46)..(46)
<223> OTHER INFORMATION: 2'-deoxy-2'-amino
<221> NAME/KEY: misc_feature
<222> LOCATION: (52)..(52)
<223> OTHER INFORMATION: 2'-deoxy-2'-amino
<221> NAME/KEY: misc_feature
<222> LOCATION: (55)..(56)
<223> OTHER INFORMATION: 2'-deoxy-2'-amino
<221> NAME/KEY: misc_feature
<222> LOCATION: (58)..(58)
<223> OTHER INFORMATION: 2'-deoxy-2'-amino
<221> NAME/KEY: misc_feature
<222> LOCATION: (60)..(60)
<223> OTHER INFORMATION: 2'-deoxy-2'-amino
<221> NAME/KEY: misc_feature
<222> LOCATION: (62)..(62)
<223> OTHER INFORMATION: 2'-deoxy-2'-amino
<221> NAME/KEY: misc_feature
<222> LOCATION: (64)..(64)
<223> OTHER INFORMATION: 2'-deoxy-2'-amino
<221> NAME/KEY: misc_feature
<222> LOCATION: (66)..(68)
<223> OTHER INFORMATION: 2'-deoxy-2'-amino
<221> NAME/KEY: misc_feature
<222> LOCATION: (72)..(73)
<223> OTHER INFORMATION: 2'-deoxy-2'-amino

<400> SEQUENCE: 52
gggaggagga agugccuggc uucgucaaac cgauaguaag cgagucaagg ucugccgcgc    60
ucgcucccag ucc                                                      73

<210> SEQ ID NO 53
<211> LENGTH: 33
<212> TYPE: RNA
<213> ORGANISM: Artificial Sequence
<220> FEATURE:
<223> OTHER INFORMATION: Description of Artificial Sequence: Nucleic
      Acid Substrate

<400> SEQUENCE: 53
ggacugggag cgagcgcggc gcaggcacug aag                                 33

<210> SEQ ID NO 54
<211> LENGTH: 72
<212> TYPE: RNA
<213> ORGANISM: Artificial Sequence
```

```
<220> FEATURE:
<223> OTHER INFORMATION: Description of Artificial Sequence:  Enzymatic
      Nucleic Acid
<221> NAME/KEY: misc_feature
<222> LOCATION: (15)..(16)
<223> OTHER INFORMATION: 2'-deoxy-2'-amino
<221> NAME/KEY: misc_feature
<222> LOCATION: (20)..(20)
<223> OTHER INFORMATION: 2'-deoxy-2'-amino
<221> NAME/KEY: misc_feature
<222> LOCATION: (23)..(23)
<223> OTHER INFORMATION: 2'-deoxy-2'-amino
<221> NAME/KEY: misc_feature
<222> LOCATION: (26)..(26)
<223> OTHER INFORMATION: 2'-deoxy-2'-amino
<221> NAME/KEY: misc_feature
<222> LOCATION: (30)..(31)
<223> OTHER INFORMATION: 2'-deoxy-2'-amino
<221> NAME/KEY: misc_feature
<222> LOCATION: (41)..(41)
<223> OTHER INFORMATION: 2'-deoxy-2'-amino
<221> NAME/KEY: misc_feature
<222> LOCATION: (46)..(46)
<223> OTHER INFORMATION: 2'-deoxy-2'-amino
<221> NAME/KEY: misc_feature
<222> LOCATION: (52)..(52)
<223> OTHER INFORMATION: 2'-deoxy-2'-amino
<221> NAME/KEY: misc_feature
<222> LOCATION: (55)..(56)
<223> OTHER INFORMATION: 2'-deoxy-2'-amino
<221> NAME/KEY: misc_feature
<222> LOCATION: (58)..(58)
<223> OTHER INFORMATION: 2'-deoxy-2'-amino
<221> NAME/KEY: misc_feature
<222> LOCATION: (60)..(60)
<223> OTHER INFORMATION: 2'-deoxy-2'-amino
<221> NAME/KEY: misc_feature
<222> LOCATION: (62)..(62)
<223> OTHER INFORMATION: 2'-deoxy-2'-amino
<221> NAME/KEY: misc_feature
<222> LOCATION: (64)..(64)
<223> OTHER INFORMATION: 2'-deoxy-2'-amino
<221> NAME/KEY: misc_feature
<222> LOCATION: (66)..(68)
<223> OTHER INFORMATION: 2'-deoxy-2'-amino
<221> NAME/KEY: misc_feature
<222> LOCATION: (72)..(73)
<223> OTHER INFORMATION: 2'-deoxy-2'-amino

<400> SEQUENCE: 54
gggaggagga agugccuggu ccuguaacua uacagggcag acgcggaaac cugccgcgcu     60
cgcucccagu cc                                                         72

<210> SEQ ID NO 55
<211> LENGTH: 73
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (15)..(16)
<223> OTHER INFORMATION: 2'-deoxy-2'-amino
<221> NAME/KEY: misc_feature
<222> LOCATION: (20)..(20)
<223> OTHER INFORMATION: 2'-deoxy-2'-amino
<221> NAME/KEY: misc_feature
<222> LOCATION: (23)..(23)
<223> OTHER INFORMATION: 2'-deoxy-2'-amino
<221> NAME/KEY: misc_feature
<222> LOCATION: (29)..(29)
<223> OTHER INFORMATION: 2'-deoxy-2'-amino
<221> NAME/KEY: misc_feature
<222> LOCATION: (37)..(37)
<223> OTHER INFORMATION: 2'-deoxy-2'-amino
<221> NAME/KEY: misc_feature
```

```
<222> LOCATION: (39)..(39)
<223> OTHER INFORMATION: 2'-deoxy-2'-amino
<221> NAME/KEY: misc_feature
<222> LOCATION: (46)..(46)
<223> OTHER INFORMATION: 2'-deoxy-2'-amino
<221> NAME/KEY: misc_feature
<222> LOCATION: (51)..(52)
<223> OTHER INFORMATION: 2'-deoxy-2'-amino
<221> NAME/KEY: misc_feature
<222> LOCATION: (55)..(56)
<223> OTHER INFORMATION: 2'-deoxy-2'-amino
<221> NAME/KEY: misc_feature
<222> LOCATION: (58)..(58)
<223> OTHER INFORMATION: 2'-deoxy-2'-amino
<221> NAME/KEY: misc_feature
<222> LOCATION: (60)..(60)
<223> OTHER INFORMATION: 2'-deoxy-2'-amino
<221> NAME/KEY: misc_feature
<222> LOCATION: (62)..(62)
<223> OTHER INFORMATION: 2'-deoxy-2'-amino
<221> NAME/KEY: misc_feature
<222> LOCATION: (64)..(64)
<223> OTHER INFORMATION: 2'-deoxy-2'-amino
<221> NAME/KEY: misc_feature
<222> LOCATION: (66)..(68)
<223> OTHER INFORMATION: 2'-deoxy-2'-amino
<221> NAME/KEY: misc_feature
<222> LOCATION: (72)..(73)
<223> OTHER INFORMATION: 2'-deoxy-2'-amino

<400> SEQUENCE: 55
gggaggagga agugccuggc gacugauacg aaaagucgca gauuucgaaa ccugccgcgc    60
ucgcucccag ucc                                                      73

<210> SEQ ID NO 56
<211> LENGTH: 70
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (15)..(16)
<223> OTHER INFORMATION: 2'-deoxy-2'-amino
<221> NAME/KEY: misc_feature
<222> LOCATION: (20)..(20)
<223> OTHER INFORMATION: 2'-deoxy-2'-amino
<221> NAME/KEY: misc_feature
<222> LOCATION: (22)..(22)
<223> OTHER INFORMATION: 2'-deoxy-2'-amino
<221> NAME/KEY: misc_feature
<222> LOCATION: (25)..(25)
<223> OTHER INFORMATION: 2'-deoxy-2'-amino
<221> NAME/KEY: misc_feature
<222> LOCATION: (36)..(36)
<223> OTHER INFORMATION: 2'-deoxy-2'-amino
<221> NAME/KEY: misc_feature
<222> LOCATION: (43)..(43)
<223> OTHER INFORMATION: 2'-deoxy-2'-amino
<221> NAME/KEY: misc_feature
<222> LOCATION: (46)..(46)
<223> OTHER INFORMATION: 2'-deoxy-2'-amino
<221> NAME/KEY: misc_feature
<222> LOCATION: (48)..(49)
<223> OTHER INFORMATION: 2'-deoxy-2'-amino
<221> NAME/KEY: misc_feature
<222> LOCATION: (52)..(53)
<223> OTHER INFORMATION: 2'-deoxy-2'-amino
<221> NAME/KEY: misc_feature
<222> LOCATION: (55)..(55)
<223> OTHER INFORMATION: 2'-deoxy-2'-amino
<221> NAME/KEY: misc_feature
<222> LOCATION: (57)..(57)
<223> OTHER INFORMATION: 2'-deoxy-2'-amino
<221> NAME/KEY: misc_feature
<222> LOCATION: (59)..(59)
```

```
<223> OTHER INFORMATION: 2'-deoxy-2'-amino
<221> NAME/KEY: misc_feature
<222> LOCATION: (61)..(61)
<223> OTHER INFORMATION: 2'-deoxy-2'-amino
<221> NAME/KEY: misc_feature
<222> LOCATION: (63)..(65)
<223> OTHER INFORMATION: 2'-deoxy-2'-amino
<221> NAME/KEY: misc_feature
<222> LOCATION: (69)..(70)
<223> OTHER INFORMATION: 2'-deoxy-2'-amino

<400> SEQUENCE: 56
gggaggagga agugccuggc ucagcauaaa gugagcagau ugcgacaccu gccgcgcucg     60
cucccagucc                                                            70

<210> SEQ ID NO 57
<211> LENGTH: 72
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (15)..(16)
<223> OTHER INFORMATION: 2'-deoxy-2'-amino
<221> NAME/KEY: misc_feature
<222> LOCATION: (31)..(31)
<223> OTHER INFORMATION: 2'-deoxy-2'-amino
<221> NAME/KEY: misc_feature
<222> LOCATION: (35)..(35)
<223> OTHER INFORMATION: 2'-deoxy-2'-amino
<221> NAME/KEY: misc_feature
<222> LOCATION: (38)..(38)
<223> OTHER INFORMATION: 2'-deoxy-2'-amino
<221> NAME/KEY: misc_feature
<222> LOCATION: (42)..(42)
<223> OTHER INFORMATION: 2'-deoxy-2'-amino
<221> NAME/KEY: misc_feature
<222> LOCATION: (45)..(45)
<223> OTHER INFORMATION: 2'-deoxy-2'-amino
<221> NAME/KEY: misc_feature
<222> LOCATION: (48)..(48)
<223> OTHER INFORMATION: 2'-deoxy-2'-amino
<221> NAME/KEY: misc_feature
<222> LOCATION: (50)..(50)
<223> OTHER INFORMATION: 2'-deoxy-2'-amino
<221> NAME/KEY: misc_feature
<222> LOCATION: (54)..(55)
<223> OTHER INFORMATION: 2'-deoxy-2'-amino
<221> NAME/KEY: misc_feature
<222> LOCATION: (57)..(57)
<223> OTHER INFORMATION: 2'-deoxy-2'-amino
<221> NAME/KEY: misc_feature
<222> LOCATION: (59)..(59)
<223> OTHER INFORMATION: 2'-deoxy-2'-amino
<221> NAME/KEY: misc_feature
<222> LOCATION: (61)..(61)
<223> OTHER INFORMATION: 2'-deoxy-2'-amino
<221> NAME/KEY: misc_feature
<222> LOCATION: (63)..(63)
<223> OTHER INFORMATION: 2'-deoxy-2'-amino
<221> NAME/KEY: misc_feature
<222> LOCATION: (65)..(67)
<223> OTHER INFORMATION: 2'-deoxy-2'-amino
<221> NAME/KEY: misc_feature
<222> LOCATION: (71)..(72)
<223> OTHER INFORMATION: 2'-deoxy-2'-amino

<400> SEQUENCE: 57
gggaggagga agugccuugg uaguaagaaa caugcugcaa acugcgacac uugccgcgcu     60
cgcucccagu cc                                                         72
```

```
<210> SEQ ID NO 58
<211> LENGTH: 32
<212> TYPE: RNA
<213> ORGANISM: Artificial Sequence
<220> FEATURE:
<223> OTHER INFORMATION: Description of Artificial Sequence: Nucleic
      Acid Substrate

<400> SEQUENCE: 58
ggacugggag cgagcgcggc gcggcacuga ag                                   32

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Nucleic
      Acid Primer

<400> SEQUENCE: 59
cacttagcat taaccctcac taaaggccgt                                      30

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: Nucleic
      Acid Primer

<400> SEQUENCE: 60
taatacgact cactatagga aggtgtgca acc                                   33

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Nucleic
      Acid Primer

<400> SEQUENCE: 61
accctcacta aaggccgt                                                   18

<210> SEQ ID NO 62
<211> LENGTH: 92
<212> TYPE: DNA
<213> ORGANISM: Artificial Sequence
<220> FEATURE:
<223> OTHER INFORMATION: Description of Artificial Sequence: Nucleic
      Acid Template
<221> NAME/KEY: misc_feature
<222> LOCATION: (19)..(78)
<223> OTHER INFORMATION: n stands for any a, c, g, or u

<400> SEQUENCE: 62
accctcacta aaggccgtnn nnnnnnnnnn nnnnnnnnnn nnnnnnnnnn nnnnnnnnnn      60
nnnnnnnnnn nnnnnnnngg ttgcacacct tg                                   92

<210> SEQ ID NO 63
<211> LENGTH: 73
<212> TYPE: DNA
<213> ORGANISM: Artificial Sequence
<220> FEATURE:
<223> OTHER INFORMATION: Description of Artificial Sequence: Nucleic
      Acid Template
```

```
<221> NAME/KEY: misc_feature
<222> LOCATION: (19)..(58)
<223> OTHER INFORMATION: n stands for any a, c, g, or u

<400> SEQUENCE: 63
accctcacta aaggccgtnn nnnnnnnnnn nnnnnnnnnn nnnnnnnnnn nnnnnnnngg    60
ttgcacacct ttg                                                       73

<210> SEQ ID NO 64
<211> LENGTH: 53
<212> TYPE: DNA
<213> ORGANISM: Artificial Sequence
<220> FEATURE:
<223> OTHER INFORMATION: Description of Artificial Sequence:  Nucleic
      Acid Template
<221> NAME/KEY: misc_feature
<222> LOCATION: (19)..(38)
<223> OTHER INFORMATION: n stands for any a, c, g, or u

<400> SEQUENCE: 64
accctcacta aaggccgtnn nnnnnnnnnn nnnnnnnngg ttgcacacct ttg            53

<210> SEQ ID NO 65
<211> LENGTH: 22
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 65 gccgugggu u gcacaccuuu cc                                            22

<210> SEQ ID NO 66
<211> LENGTH: 16
<212> TYPE: RNA
<213> ORGANISM: Artificial Sequence
<220> FEATURE:
<223> OTHER INFORMATION: Description of Artificial Sequence:  Nucleic
      Acid Substrate

<400> SEQUENCE: 66
gguugcacac cuuucc                                                    16

<210> SEQ ID NO 67
<211> LENGTH: 73
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (18)..(52)
<223> OTHER INFORMATION: n stands for any a, c, g, or u

<400> SEQUENCE: 67
gggaggagga agugccunnn nnnnnnnnnn nnnnnnnnnn nnnnnnnnnn nnugccgcgc    60
ucgcucccag ucc                                                       73

<210> SEQ ID NO 68
<211> LENGTH: 36
<212> TYPE: RNA
<213> ORGANISM: Artificial Sequence
<220> FEATURE:
<223> OTHER INFORMATION: Description of Artificial Sequence:  Nucleic
      Acid Substrate
<221> NAME/KEY: misc_feature
```

```
-continued

<222> LOCATION: (1)..(1)
<223> OTHER INFORMATION: n stands for biotin (Glen Research Cat. No.
      10-1953-nn)
<221> NAME/KEY: misc_feature
<222> LOCATION: (1)..(1)
<223> OTHER INFORMATION: Polethylene glycol spacer (Glenn Research
      Cat. No. 10-1918-nn)
<221> NAME/KEY: misc_feature
<222> LOCATION: (33)..(33)
<223> OTHER INFORMATION: Polethylene glycol spacer (Glenn Research
      Cat. No. 10-1918-nn)
<221> NAME/KEY: misc_feature
<222> LOCATION: (34)..(34)
<223> OTHER INFORMATION: n stands for thiol-modifier C6 S-S (Glen
      Research Cat. No. 10-1936-nn)
<221> NAME/KEY: misc_feature
<222> LOCATION: (35)..(35)
<223> OTHER INFORMATION: n stands for inverted deoxyabasic derivative

<400> SEQUENCE: 68 nggacugggag cgagcgcggc gcaggcacug aagnn                          36

<210> SEQ ID NO 69
<211> LENGTH: 16
<212> TYPE: RNA
<213> ORGANISM: Artificial Sequence
<220> FEATURE:
<223> OTHER INFORMATION: Description of Artificial Sequence:
      Biotinylated Substrate Sequence

<400> SEQUENCE: 69
gccguggguu gcacac                                                16
```